United States Patent
Brown et al.

(10) Patent No.: US 10,004,737 B2
(45) Date of Patent: Jun. 26, 2018

(54) FUSED IMIDAZOLE AND PYRAZOLE DERIVATIVES AS MODULATORS OF TNF ACTIVITY

(71) Applicant: UCB BIOPHARMA SPRL, Brussels (BE)

(72) Inventors: Julien Alistair Brown, Slough (GB); Mark Daniel Calmiano, Slough (GB); Elizabeth Pearl Jones, Slough (GB); Boris Kroeplien, Slough (GB); James Thomas Reuberson, Slough (GB); Matthew Duncan Selby, Slough (GB); Michael Alan Shaw, Slough (GB); Zhaoning Zhu, Slough (GB)

(73) Assignee: UCB BIOPHARMA SPRL, Brussels (BY)

( * ) Notice: Subject to any disclaimer, the term of this patent is extended or adjusted under 35 U.S.C. 154(b) by 0 days. days.

(21) Appl. No.: 15/039,092

(22) PCT Filed: Dec. 8, 2014

(86) PCT No.: PCT/EP2014/076853
§ 371 (c)(1),
(2) Date: May 25, 2016

(87) PCT Pub. No.: WO2015/086512
PCT Pub. Date: Jun. 18, 2015

(65) Prior Publication Data
US 2017/0128445 A1 May 11, 2017

(30) Foreign Application Priority Data
Dec. 9, 2013 (GB) .................... 1321746.8

(51) Int. Cl.
A61K 31/506 (2006.01)
A61K 31/437 (2006.01)
A61K 31/444 (2006.01)
A61K 31/5377 (2006.01)
A61K 31/4985 (2006.01)
C07D 471/04 (2006.01)
C07D 487/04 (2006.01)
C07D 519/00 (2006.01)
A61K 45/06 (2006.01)

(52) U.S. Cl.
CPC .......... *A61K 31/506* (2013.01); *A61K 31/437* (2013.01); *A61K 31/444* (2013.01); *A61K 31/5377* (2013.01); *C07D 471/04* (2013.01); *C07D 487/04* (2013.01); *C07D 519/00* (2013.01); *A61K 31/4985* (2013.01); *A61K 45/06* (2013.01)

(58) Field of Classification Search
None
See application file for complete search history.

(56) References Cited

FOREIGN PATENT DOCUMENTS

| EP | 1 262 180 A1 | 12/2002 |
|----|--------------|---------|
| WO | 07/112093 A2 | 10/2007 |
| WO | 13/186229 A1 | 12/2013 |
| WO | 14/009295 A1 | 1/2014 |
| WO | 14/009296 A1 | 1/2014 |

OTHER PUBLICATIONS

Database Registry Chemical Abstracts Service, Columbus, Ohio, Accession No. RN 132783-74-5, Entered STN: Mar. 22, 1991.*
Ito, Nobuyuki. Cancer Science 94(1), (2003) 3-8.*
You et al., "Synthesis of 3-(1H-benzo[d]imidazol-1-yl)isoindolin-1-one derivatives promoted by EtOH—AcOH solvent system", Tetrahedron Letters, 2013, vol. 54, 2972-2975.
Tansey et al., "The TNF superfamily in 2009: new pathways, new indications, and new drugs", Drug Discovery Today, 2009, 14(23/24), 1082-1088.
Carneiro et al., "Emerging Role for TNF-α in Erectile Dysfunction", J. Sexual Medicine, 2010, vol. 7, 3823-3834.
Wu et al., "Do TNF Inhibitors Reduce the Risk of Myocardial Infarction in Psoriasis Patients?", JAMA, 2013, 309(19), 2043-2044.
Hauwermeiren et al., "Safe TNF-based antitumor therapy following p55TNFR reduction in intestinal epithelium", The Journal of Clinical Investigation, 2013, 123(6), 2590-2603.
Pan et al., "Iron-Catalyzed N-Alkylation of Azoles via Oxidation of C—H Bond Adjacent to an Oxygen Atom", Organic Letters, 2010, 12(9), 1932-1935.
Shi et al., "2-[1-(3-Oxo-1,3-dihydro-2-benzofuran-1-yl)-1H-benzimidazol-2-yl]benzoic acid methanol solvate", Acta Crystallographica Section E structure Reports Online, 2010, 65(8), o2034, 10 pages.

* cited by examiner

*Primary Examiner* — Samantha L Shterengarts
(74) *Attorney, Agent, or Firm* — McDonnell Boehnen Hulbert & Berghoff LLP

(57) ABSTRACT

A series of substituted benzimidazole, imidazo[1,2-α]pyridine and pyrazolo[1,5-α]pyridine derivatives, and analogs thereof, being potent modulators of human TNFα activity, are accordingly of benefit in the treatment and/or prevention of various human ailments, including autoimmune and inflammatory disorders; neurological and neurodegenerative disorders; pain and nociceptive disorders; cardiovascular disorders; metabolic disorders; ocular disorders; and oncological disorders.

8 Claims, No Drawings

FUSED IMIDAZOLE AND PYRAZOLE DERIVATIVES AS MODULATORS OF TNF ACTIVITY

This application is the US national phase under 35 U.S.C. § 371 of international application PCT/EP2014/076853, filed Dec. 8, 2014, which claims priority to GB application 1321746.8, filed Dec. 9, 2013.

The present invention relates to a class of fused imidazole and pyrazole derivatives, and to their use in therapy. More particularly, this invention is concerned with pharmacologically active substituted benzimidazole, imidazo[1,2-a]pyridine and pyrazolo[1,5-a]pyridine derivatives, and analogues thereof. These compounds are modulators of the signalling of TNFα, and are accordingly of benefit as pharmaceutical agents, especially in the treatment of adverse inflammatory and autoimmune disorders, neurological and neurodegenerative disorders, pain and nociceptive disorders, cardiovascular disorders, metabolic disorders, ocular disorders, and oncological disorders.

TNFα is the prototypical member of the Tumour Necrosis Factor (TNF) superfamily of proteins that share a primary function of regulating cell survival and cell death. One structural feature common to all known members of the TNF superfamily is the formation of trimeric complexes that bind to, and activate, specific TNF superfamily receptors. By way of example, TNFα exists in soluble and transmembrane forms and signals through two receptors, known as TNFR1 and TNFR2, with distinct functional endpoints.

Various products capable of modulating TNFα activity are already commercially available. All are approved for the treatment of inflammatory and autoimmune disorders such as rheumatoid arthritis and Crohn's disease. All currently approved products are macromolecular and act by inhibiting the binding of human TNFα to its receptor. Typical macromolecular TNFα inhibitors include anti-TNFα antibodies; and soluble TNFα receptor fusion proteins. Examples of commercially available anti-TNFα antibodies include fully human antibodies such as adalimumab (Humira®) and golimumab (Simponi®), chimeric antibodies such as infliximab (Remicade®), and pegylated Fab' fragments such as certolizumab pegol (Cimzia®). An example of a commercially available soluble TNFα receptor fusion protein is etanercept (Enbrel®).

TNF superfamily members, including TNFα itself, are implicated in a variety of physiological and pathological functions that are believed to play a part in a range of conditions of significant medical importance (see, for example, M. G. Tansey & D. E. Szymkowski, *Drug Discovery Today*, 2009, 14, 1082-1088; and F. S. Carneiro et al., *J. Sexual Medicine*, 2010, 7, 3823-3834).

The compounds in accordance with the present invention, being potent modulators of human TNFα activity, are therefore beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

In addition, the compounds in accordance with the present invention may be beneficial as pharmacological standards for use in the development of new biological tests and in the search for new pharmacological agents. Thus, in one embodiment, the compounds of this invention may be useful as radioligands in assays for detecting pharmacologically active compounds. In an alternative embodiment, certain compounds of this invention may be useful for coupling to a fluorophore to provide fluorescent conjugates that can be utilised in assays (e.g. a fluorescence polarisation assay) for detecting pharmacologically active compounds.

Co-pending international patent applications WO 2013/186229 (published 19 Dec. 2013), WO 2014/009295 (published 16 Jan. 2014) and WO 2014/009296 (also published 16 Jan. 2014) describe fused imidazole derivatives which are modulators of human TNFα activity.

None of the prior art available to date, however, discloses or suggests the precise structural class of fused imidazole and pyrazole derivatives as provided by the present invention.

The compounds in accordance with the present invention potently inhibit the binding of a fluorescence conjugate to TNFα when tested in the fluorescence polarisation assay described herein. Indeed, when tested in that assay, the compounds of the present invention exhibit an $IC_{50}$ value of 50 µM or less, generally of 20 µM or less, usually of 5 µM or less, typically of 1 µM or less, suitably of 500 nM or less, ideally of 100 nM or less, and preferably of 20 nM or less (the skilled person will appreciate that a lower $IC_{50}$ figure denotes a more active compound).

Certain compounds in accordance with the present invention potently neutralise the activity of TNFα in a commercially available HEK-293 derived reporter cell line known as HEK-Blue™ CD40L. This is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a concentration-dependent manner by TNFα. When tested in the HEK-293 bioassay, also referred to herein as the reporter gene assay, certain compounds of the present invention exhibit an $IC_{50}$ value of 50 µM or less, generally of 20 µM or less, usually of 5 µM or less, typically of 1 µM or less, suitably of 500 nM or less, ideally of 100 nM or less, and preferably of 20 nM or less (as before, the skilled person will appreciate that a lower $IC_{50}$ figure denotes a more active compound).

The present invention provides a compound of formula (IA), (IB) or (IC) or an N-oxide thereof, or a pharmaceutically acceptable salt or solvate thereof, or a glucuronide derivative thereof, or a co-crystal thereof:

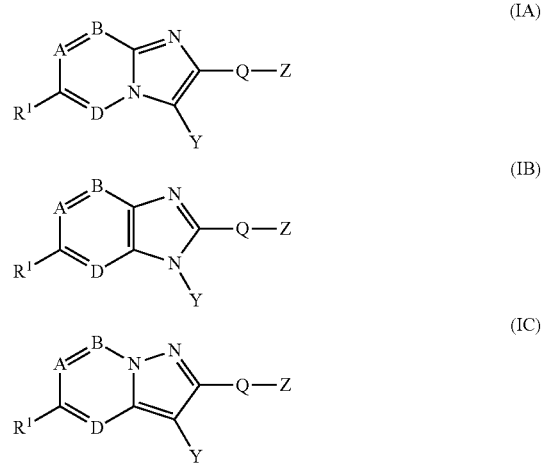

wherein
A represents C—$R^2$ or N;
B represents C—$R^3$ or N;

D represents C—R$^4$ or N;
Y represents a group of formula (Ya):

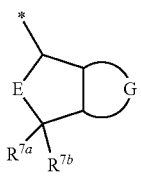
(Ya)

the asterisk (*) represents the point of attachment to the remainder of the molecule;

E represents —O—, —S—, —S(O)—, —S(O)$_2$—, —S(O)(NR$^5$)— or —N(R$^5$)—;

G represents the residue of an optionally substituted benzene ring; or an optionally substituted five-membered heteroaromatic ring selected from furyl, thienyl, pyrrolyl, pyrazolyl, oxazolyl, isoxazolyl, thiazolyl, isothiazolyl, imidazolyl, oxadiazolyl, thiadiazolyl and triazolyl; or an optionally substituted six-membered heteroaromatic ring selected from pyridinyl, pyridazinyl, pyrimidinyl, pyrazinyl and triazinyl;

Q represents a covalent bond; or Q represents —O—, —S—, —S(O)—, —S(O)$_2$—, —S(O)(NR$^6$)—, —N(R$^6$)—, —C(O)N(R$^6$)—, —N(R$^6$)C(O)—, —S(O)$_2$N(R$^6$)— or —N(R$^6$)S(O)$_2$—; or Q represents an optionally substituted straight or branched C$_{1-6}$ alkylene chain optionally comprising one, two or three heteroatom-containing linkages independently selected from —O—, —S—, —S(O)—, —S(O)$_2$—, —S(O)(NR$^6$)—, —N(R$^6$)—, —C(O)N(R$^6$)—, —N(R$^6$)C(O)—, —S(O)$_2$N(R$^6$)— and —N(R$^6$)S(O)$_2$—;

Z represents hydrogen, halogen or trifluoromethyl; or Z represents C$_{1-6}$ alkyl, C$_{3-7}$ cycloalkyl, aryl, C$_{3-7}$ heterocycloalkyl, C$_{3-7}$ heterocycloalkenyl or heteroaryl, any of which groups may be optionally substituted by one or more substituents; or Z represents —Z$^1$—Z$^2$ or —Z$^1$—C(O)—Z$^2$, either of which moieties may be optionally substituted by one or more substituents;

Z$^1$ represents a divalent radical derived from an aryl, C$_{3-7}$ heterocycloalkyl or heteroaryl group;

Z$^2$ represents aryl, C$_{3-7}$ heterocycloalkyl, C$_{3-7}$ heterocycloalkenyl or heteroaryl; R$^1$, R$^2$, R$^3$ and R$^4$ independently represent hydrogen, halogen, cyano, nitro, hydroxy, trifluoromethyl, trifluoromethoxy, —OR$^a$, —SR$^a$, —SOR$^a$, —SO$_2$R$^a$, —SF$_5$, —NR$^b$R$^c$, —NR$^c$COR$^d$, —NR$^c$CO$_2$R$^d$, —NHCONR$^b$R$^c$, —NR$^c$SO$_2$R$^e$, —N(SO$_2$R$^e$)$_2$, —NHSO$_2$NR$^b$R$^c$, —COR$^d$, —CO$_2$R$^d$, —CONR$^b$R$^c$, —CON(OR$^a$)R$^b$, —SO$_2$NR$^b$R$^c$ or —SO(NR$^b$)R$^d$; or C$_{1-6}$ alkyl, C$_{2-6}$ alkenyl, C$_{2-6}$ alkynyl, C$_{3-7}$ cycloalkyl, C$_{4-7}$ cycloalkenyl, C$_{3-7}$ cycloalkyl(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, C$_{3-7}$ heterocycloalkenyl, C$_{4-9}$ heterobicycloalkyl, heteroaryl, heteroaryl(C$_{1-6}$)alkyl, (C$_{3-7}$)heterocycloalkyl(C$_{1-6}$)alkyl-aryl-, heteroaryl(C$_{3-7}$)heterocycloalkyl-, (C$_{3-7}$)cycloalkyl-heteroaryl-, (C$_{3-7}$)cycloalkyl(C$_{1-6}$)alkyl-heteroaryl-, (C$_{4-7}$)cycloalkenyl-heteroaryl-, (C$_{4-9}$)bicycloalkyl-heteroaryl-, (C$_{3-7}$)heterocycloalkyl-heteroaryl-, (C$_{3-7}$)heterocycloalkyl(C$_{1-6}$)alkyl-heteroaryl-, (C$_{3-7}$)heterocycloalkenyl-heteroaryl-, (C$_{4-9}$)heterobicycloalkyl-heteroaryl- or (C$_{4-9}$)spiroheterocycloalkyl-heteroaryl-, any of which groups may be optionally substituted by one or more substituents;

R$^5$ represents hydrogen, C$_{1-6}$ alkyl, —SO$_2$R$^a$, —COR$^d$, —CONR$^b$R$^c$, —SO$_2$NR$^b$R$^c$ or —SO(NR$^b$)R$^d$;

R$^6$ represents hydrogen, C$_{1-6}$ alkyl;
R$^{7a}$ represents hydrogen, C$_{1-6}$ alkyl or trifluoromethyl; and
R$^{7b}$ represents hydrogen or C$_{1-6}$ alkyl; or
R$^{7a}$ and R$^{7b}$, when taken together with the carbon atom to which they are both attached, represent carbonyl (C=O); or
R$^{7a}$ and R$^{7b}$, when taken together with the carbon atom to which they are both attached, represent C$_{3-7}$ cycloalkyl or C$_{3-7}$ heterocycloalkyl, either of which groups may be optionally substituted by one or more substituents;

R$^a$ represents C$_{1-6}$ alkyl, aryl, aryl(C$_{1-6}$)alkyl, heteroaryl or heteroaryl(C$_{1-6}$)alkyl, any of which groups may be optionally substituted by one or more substituents;

R$^b$ and R$^c$ independently represent hydrogen or trifluoromethyl; or C$_{1-6}$ alkyl, C$_{3-7}$ cycloalkyl, C$_{3-7}$ cycloalkyl(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, heteroaryl or heteroaryl(C$_{1-6}$) alkyl, any of which groups may be optionally substituted by one or more substituents; or R$^b$ and R$^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents;

R$^d$ represents hydrogen; or C$_{1-6}$ alkyl, C$_{3-7}$ cycloalkyl, aryl, C$_{3-7}$ heterocycloalkyl or heteroaryl, any of which groups may be optionally substituted by one or more substituents; and R$^e$ represents C$_{1-6}$ alkyl, aryl or heteroaryl, any of which groups may be optionally substituted by one or more substituents.

The present invention also provides a compound of formula (IA), (IB) or (IC) as defined above or an N-oxide thereof, or a pharmaceutically acceptable salt or solvate thereof, or a glucuronide derivative thereof, or a co-crystal thereof, for use in therapy.

The present invention also provides a compound of formula (IA), (IB) or (IC) as defined above or an N-oxide thereof, or a pharmaceutically acceptable salt or solvate thereof, or a glucuronide derivative thereof, or a co-crystal thereof, for use in the treatment and/or prevention of disorders for which the administration of a modulator of TNFα function is indicated.

In another aspect, the present invention provides a compound of formula (IA), (IB) or (IC) as defined above or an N-oxide thereof, or a pharmaceutically acceptable salt or solvate thereof, or a glucuronide derivative thereof, or a co-crystal thereof, for use in the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides a method for the treatment and/or prevention of disorders for which the administration of a modulator of TNFα function is indicated which comprises administering to a patient in need of such treatment an effective amount of a compound of formula (IA), (IB) or (IC) as defined above or an N-oxide thereof, or a pharmaceutically acceptable salt or solvate thereof, or a glucuronide derivative thereof, or a co-crystal thereof.

In another aspect, the present invention provides a method for the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder, which comprises administering to a patient in need of such treatment an effective amount of a compound of formula (IA), (IB) or (IC) as defined above or an N-oxide thereof, or a pharmaceutically acceptable salt or solvate thereof, or a glucuronide derivative thereof, or a co-crystal thereof.

Where any of the groups in the compounds of formula (IA), (IB) or (IC) above is stated to be optionally substituted, this group may be unsubstituted, or substituted by one or more substituents. Typically, such groups will be unsubstituted, or substituted by one or two substituents.

For use in medicine, the salts of the compounds of formula (IA), (IB) or (IC) will be pharmaceutically acceptable salts. Other salts may, however, be useful in the preparation of the compounds of use in the invention or of their pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002. Suitable pharmaceutically acceptable salts of the compounds of use in this invention include acid addition salts which may, for example, be formed by mixing a solution of the compound of use in the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of use in the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; ammonium salts; and salts formed with suitable organic ligands, e.g. quaternary ammonium salts, and meglumine salts.

The present invention includes within its scope solvates of the compounds of formula (IA), (IB) or (IC) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (IA), (IB) or (IC) may be formed with water, in which case they will be hydrates.

The present invention also includes co-crystals within its scope. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012). Typical examples of co-crystal formers, which may be present in the co-crystal alongside the active pharmaceutical ingredient, include L-ascorbic acid, citric acid, glutaric acid, urea and nicotinamide.

The present invention includes within its scope prodrugs of the compounds of formula (IA), (IB) or (IC) above. In general, such prodrugs will be functional derivatives of the compounds of formula (IA), (IB) or (IC) which are readily convertible in vivo into the required compound of formula (IA), (IB) or (IC). Conventional procedures for the selection and preparation of suitable prodrug derivatives are described, for example, in *Design of Prodrugs*, ed. H. Bundgaard, Elsevier, 1985.

Suitable alkyl groups which may be present on the compounds of use in the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

The expression "$C_{1-4}$ alkylene chain" refers to a divalent straight or branched alkylene chain containing 1 to 4 carbon atoms. Typical examples include methylene, ethylene, methylmethylene, ethylmethylene and dimethylmethylene.

Suitable $C_{2-6}$ alkenyl groups include vinyl and allyl.

Suitable $C_{2-6}$ alkynyl groups include ethynyl, propargyl and butynyl.

The term "$C_{4-7}$ cycloalkyl" as used herein refers to monovalent groups of 3 to 7 carbon atoms derived from a saturated monocyclic hydrocarbon, and may comprise benzo-fused analogues thereof. Suitable $C_{3-7}$ cycloalkyl groups include cyclopropyl, cyclobutyl, benzocyclobutenyl, cyclopentyl, indanyl, cyclohexyl and cycloheptyl.

The term "$C_{4-7}$ cycloalkenyl" as used herein refers to monovalent groups of 4 to 7 carbon atoms derived from a partially unsaturated monocyclic hydrocarbon. Suitable $C_{4-7}$ cycloalkenyl groups include cyclobutenyl, cyclopentenyl, cyclohexenyl and cycloheptenyl.

The term "$C_{4-9}$ bicycloalkyl" as used herein refers to monovalent groups of 4 to 9 carbon atoms derived from a saturated bicyclic hydrocarbon. Typical bicycloalkyl groups include bicyclo[3.1.0]hexanyl, bicyclo[4.1.0]heptanyl and bicyclo[2.2.2]octanyl.

The term "aryl" as used herein refers to monovalent carbocyclic aromatic groups derived from a single aromatic ring or multiple condensed aromatic rings. Suitable aryl groups include phenyl and naphthyl, preferably phenyl.

Suitable aryl($C_{1-6}$)alkyl groups include benzyl, phenylethyl, phenylpropyl and naphthylmethyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Suitable heterocycloalkyl groups include oxetanyl, azetidinyl, tetrahydrofuranyl, dihydrobenzo-furanyl, dihydrobenzothienyl, pyrrolidinyl, indolinyl, isoindolinyl, oxazolidinyl, thiazolidinyl, isothiazolidinyl, imidazolidinyl, tetrahydropyranyl, chromanyl, tetrahydro-thiopyranyl, piperidinyl, 1,2,3,4-tetrahydroquinolinyl, 1,2,3,4-tetrahydroisoquinolinyl, piperazinyl, 1,2,3,4-tetrahydroquinoxalinyl, hexahydro-[1,2,5]thiadiazolo[2,3-a]pyrazinyl, homopiperazinyl, morpholinyl, benzoxazinyl, thiomorpholinyl, azepanyl, oxazepanyl, diazepanyl, thiadiazepanyl and azocanyl.

The term "$C_{3-7}$ heterocycloalkenyl" as used herein refers to monounsaturated or polyunsaturated monocyclic rings containing 3 to 7 carbon atoms and at least one heteroatom selected from oxygen, sulphur and nitrogen, and may comprise benzo-fused analogues thereof. Suitable heterocycloalkenyl groups include thiazolinyl, isothiazolinyl, imidazolinyl, dihydropyranyl, dihydrothiopyranyl and 1,2,3,6-tetrahydropyridinyl.

The term "$C_{4-9}$ heterobicycloalkyl" as used herein corresponds to $C_{4-9}$ bicycloalkyl wherein one or more of the carbon atoms have been replaced by one or more heteroatoms selected from oxygen, sulphur and nitrogen. Typical heterobicycloalkyl groups include 3-azabicyclo[3.1.0]hexanyl, 2-oxa-5-azabicyclo[2.2.1]heptanyl, 6-azabicyclo[3.2.0] heptanyl, 3-azabicyclo[3.1.1]heptanyl, 3-azabicyclo[4.1.0] heptanyl, 2-oxabicyclo[2.2.2]octanyl, quinuclidinyl, 2-oxa-5-azabicyclo[2.2.2]octanyl, 3-azabicyclo[3.2.1]octanyl, 8-azabicyclo-[3.2.1]octanyl, 3-oxa-8-azabicyclo[3.2.1]octanyl, 3,8-diazabicyclo[3.2.1]octanyl, 3,6-diazabicyclo[3.2.2] nonanyl, 3-oxa-7-azabicyclo[3.3.1]nonanyl and 3,9-diazabicyclo-[4.2.1]nonanyl.

The term "$C_{4-9}$ spiroheterocycloalkyl" as used herein refers to saturated bicyclic ring systems containing 4 to 9 carbon atoms and at least one heteroatom selected from oxygen, sulphur and nitrogen, in which the two rings are linked by a common atom.

Suitable spiroheterocycloalkyl groups include 5-azaspiro[2.3]hexanyl, 5-azaspiro[2.4]-heptanyl, 2-azaspiro[3.3]heptanyl, 2-oxa-6-azaspiro[3.3]heptanyl, 2-oxa-6-azaspiro[3.4]-octanyl, 2-oxa-6-azaspiro[3.5]nonanyl, 7-oxa-2-azaspiro[3.5]nonanyl, 2-oxa-7-azaspiro-[3.5]nonanyl and 2,4,8-triazaspiro[4.5]decanyl.

The term "heteroaryl" as used herein refers to monovalent aromatic groups containing at least 5 atoms derived from a single ring or multiple condensed rings, wherein one or more carbon atoms have been replaced by one or more heteroatoms selected from oxygen, sulphur and nitrogen. Suitable heteroaryl groups include furyl, benzofuryl, dibenzofuryl, thienyl, benzothienyl, thieno[2,3-c]pyrazolyl, thieno[3,4-b][1,4]dioxinyl, dibenzothienyl, pyrrolyl, indolyl, pyrrolo[2,3-b]pyridinyl, pyrrolo[3,2-c]pyridinyl, pyrrolo[3,4-b]pyridinyl, pyrazolyl, pyrazolo[1,5-a]pyridinyl, pyrazolo[3,4-d]pyrimidinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[2,1-b]thiazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, triazolyl, [1,2,4]triazolo[1,5-a]-pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (IA), (IB) or (IC) have one or more asymmetric centres, they may accordingly exist as enantiomers. Where the compounds of use in the invention possess two or more asymmetric centres, they may additionally exist as diastereomers. The invention is to be understood to extend to the use of all such enantiomers and diastereomers, and to mixtures thereof in any proportion, including racemates. Formula (IA), (IB) or (IC) and the formulae depicted hereinafter are intended to represent all individual stereoisomers and all possible mixtures thereof, unless stated or shown otherwise. In addition, compounds of formula (IA), (IB) or (IC) may exist as tautomers, for example keto ($CH_2C=O$)↔enol (CH=CHOH) tautomers or amide (NHC=O)↔hydroxyimine (N=COH) tautomers. Formula (IA), (IB) or (IC) and the formulae depicted hereinafter are intended to represent all individual tautomers and all possible mixtures thereof, unless stated or shown otherwise.

It is to be understood that each individual atom present in formula (IA), (IB) or (IC), or in the formulae depicted hereinafter, may in fact be present in the form of any of its naturally occurring isotopes, with the most abundant isotope(s) being preferred. Thus, by way of example, each individual hydrogen atom present in formula (IA), (IB) or (IC), or in the formulae depicted hereinafter, may be present as a $^1H$, $^2H$ (deuterium) or $^3H$ (tritium) atom, preferably $^1H$. Similarly, by way of example, each individual carbon atom present in formula (IA), (IB) or (IC), or in the formulae depicted hereinafter, may be present as a $^{12}C$, $^{13}C$ or $^{14}C$ atom, preferably $^{12}C$.

In one aspect, the present invention provides a compound of formula (IA), (IB) or (IC) as depicted above or an N-oxide thereof, or a pharmaceutically acceptable salt or solvate thereof, or a glucuronide derivative thereof, or a co-crystal thereof, wherein Q represents —O—, —S—, —S(O)—, —S(O)$_2$—, —S(O)(NR$^6$)—, —N(R$^6$)—, —C(O)N(R$^6$)—, —N(R$^6$)C(O)—, —S(O)$_2$N(R$^6$)— or —N(R$^6$)S(O)$_2$—; or Q represents an optionally substituted straight or branched $C_{1-6}$ alkylene chain optionally comprising one, two or three heteroatom-containing linkages independently selected from —O—, —S—, —S(O)—, —S(O)$_2$—, —S(O)(NR$^6$)—, —N(R$^6$)—, —C(O)N(R$^6$)—, —N(R$^6$)C(O)—, —S(O)$_2$N(R$^6$)— and —N(R$^6$)S(O)$_2$—;

Z represents $C_{3-7}$ cycloalkyl, aryl, $C_{3-7}$ heterocycloalkyl, $C_{3-7}$ heterocycloalkenyl or heteroaryl, any of which groups may be optionally substituted by one or more substituents; or Z represents —$Z^1$-$Z^2$ or —$Z^1$—C(O)—$Z^2$, either of which moieties may be optionally substituted by one or more substituents; and A, B, D, Y, R$^1$, R$^6$, Z$^1$ and Z$^2$ are as defined above.

In another aspect, the present invention provides a compound of formula (IA), (IB) or (IC) as depicted above or an N-oxide thereof, or a pharmaceutically acceptable salt or solvate thereof, or a glucuronide derivative thereof, or a co-crystal thereof, wherein R$^1$ represents halogen or cyano; or $C_{1-6}$ alkyl, $C_{2-6}$ alkenyl, $C_{2-6}$ alkynyl, $C_{3-7}$ cycloalkyl, $C_{4-7}$ cycloalkenyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkenyl, $C_{4-9}$ heterobicycloalkyl, heteroaryl, heteroaryl($C_{1-6}$)alkyl, ($C_{3-7}$)heterocycloalkyl($C_{1-6}$)alkyl-aryl-, heteroaryl($C_{3-7}$)heterocycloalkyl-, ($C_{3-7}$)cycloalkyl-heteroaryl-, ($C_{3-7}$)cycloalkyl-($C_{1-6}$)alkyl-heteroaryl-, ($C_{4-7}$)cycloalkenyl-heteroaryl-, ($C_{4-9}$)bicycloalkyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$) spiroheterocycloalkyl-heteroaryl-, any of which groups may be optionally substituted by one or more substituents; and A, B, D, Y, Q and Z are as defined above.

In one embodiment, A represents C—R$^2$. In another embodiment, A represents N.

In one embodiment, B represents C—R$^3$. In another embodiment, B represents N.

In one embodiment, D represents C—R$^4$. In another embodiment, D represents N.

In a first embodiment, A represents C—R$^2$, B represents C—R$^3$ and D represents C—R$^4$.

In a second embodiment, A represents C—R$^2$, B represents C—R$^3$ and D represents N.

In a third embodiment, A represents C—R$^2$, B represents N and D represents C—R$^4$.

In a fourth embodiment, A represents C—R$^2$, B represents N and D represents N.

In a fifth embodiment, A represents N, B represents C—R$^3$ and D represents C—R$^4$.

In a sixth embodiment, A represents N, B represents C—R³ and D represents N.

In a seventh embodiment, A represents N, B represents N and D represents C—R⁴.

In an eighth embodiment, A represents N, B represents N and D represents N.

Suitably, A represents C—R², and B and D are as defined above; or A represents N, B represents C—R³, and D is as defined above.

Suitably, A represents C—R² or N, B represents C—R³ and D represents C—R⁴.

Particular sub-classes of compounds in accordance with the present invention include the compounds of formula (IA-A) and (IA-B):

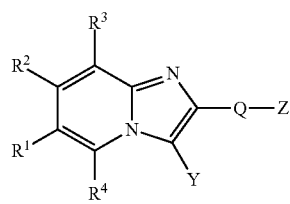

(IA-A)

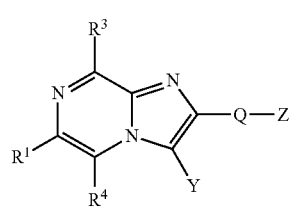

(IA-B)

wherein Y, Q, Z, R¹, R², R³ and R⁴ are as defined above.

In a first embodiment, the present invention provides a compound of formula (IA-A) as defined above.

In a second embodiment, the present invention provides a compound of formula (IA-B) as defined above.

Suitably, E represents —O— or —N(R⁵)—.

In a first embodiment, E represents —O—. In a second embodiment, E represents —S—. In a third embodiment, E represents —S(O)—. In a fourth embodiment, E represents —S(O)₂—. In a fifth embodiment, E represents —S(O)(NR⁵)—. In a sixth embodiment, E represents —N(R⁵)—.

In the compounds of the invention, the moiety G is defined as representing the residue of an optionally substituted benzene ring, or an optionally substituted five-membered or six-membered heteroaromatic ring as specified above. From this it is to be understood that the variable G, when taken together with the two carbon atoms of the five-membered ring to which the G-containing ring is fused, represents an optionally substituted benzene ring, or an optionally substituted five-membered or six-membered heteroaromatic ring as specified above.

In a first embodiment, the moiety G in the compounds of the invention represents the residue of an optionally substituted benzene ring.

In a second embodiment, the moiety G in the compounds of the invention represents the residue of an optionally substituted five-membered heteroaromatic ring selected from furyl, thienyl, pyrrolyl, pyrazolyl, oxazolyl, isoxazolyl, thiazolyl, isothiazolyl, imidazolyl, oxadiazolyl, thiadiazolyl, triazolyl and tetrazolyl.

In a third embodiment, the moiety G in the compounds of the invention represents the residue of an optionally substituted six-membered heteroaromatic ring selected from pyridinyl, pyridazinyl, pyrimidinyl, pyrazinyl and triazinyl.

The aromatic or heteroaromatic ring of which the moiety G is the residue may be unsubstituted, or may be substituted, where possible, by one or more substituents, typically by one or two substituents. In one embodiment, this ring is unsubstituted. In another embodiment, this ring is monosubstituted. In a further embodiment, this ring is disubstituted.

Typical examples of optional substituents on the aromatic or heteroaromatic ring of which the moiety G is the residue include $C_{1-6}$ alkyl, halogen, cyano, trifluoromethyl, hydroxy, $C_{1-6}$ alkoxy, difluoromethoxy, $C_{1-6}$ alkylthio, $C_{1-6}$ alkylsulphinyl, $C_{1-6}$ alkylsulphonyl, $C_{2-6}$ alkylcarbonyl, amino, $C_{1-6}$ alkylamino and di($C_{1-6}$)alkylamino.

Illustrative examples of optional substituents on the aromatic or heteroaromatic ring of which the moiety G is the residue include $C_{1-6}$ alkoxy.

Typical examples of particular substituents on the aromatic or heteroaromatic ring of which the moiety G is the residue include methyl, fluoro, chloro, bromo, cyano, trifluoromethyl, hydroxy, methoxy, difluoromethoxy, methylthio, methylsulphinyl, methylsulphonyl, acetyl, amino, methylamino and dimethylamino.

Illustrative examples of particular substituents on the aromatic or heteroaromatic ring of which the moiety G is the residue include methoxy.

Suitable values of Y include the groups of formula (Ya-1) and (Ya-2):

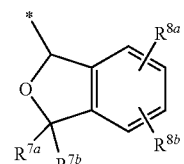

(Ya-1)

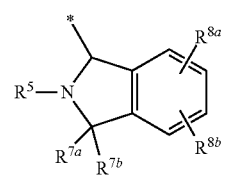

(Ya-2)

wherein the asterisk (*) represents the point of attachment to the remainder of the molecule;

$R^{8a}$ and $R^{8b}$ independently represent $C_{1-6}$ alkyl, halogen, cyano, trifluoromethyl, hydroxy, $C_{1-6}$ alkoxy, difluoromethoxy, $C_{1-6}$ alkylthio, $C_{1-6}$ alkylsulphinyl, $C_{1-6}$ alkylsulphonyl, $C_{2-6}$ alkylcarbonyl, amino, $C_{1-6}$ alkylamino or di($C_{1-6}$)alkylamino; and $R^5$, $R^{7a}$ and $R^{7b}$ are as defined above.

Suitably, $R^{8a}$ and $R^{8b}$ independently represent methyl, fluoro, chloro, bromo, cyano, trifluoromethyl, hydroxy, methoxy, difluoromethoxy, methylthio, methylsulphinyl, methylsulphonyl, acetyl, amino, methylamino and dimethylamino.

Typical values of $R^{8a}$ include hydrogen and $C_{1-6}$ alkoxy.

In a first embodiment, $R^{8a}$ represents hydrogen. In a second embodiment, $R^{8a}$ represents $C_{1-6}$ alkoxy, especially methoxy.

Typically, $R^{8a}$ represents hydrogen or methoxy.

In a particular embodiment, $R^{8b}$ represents hydrogen.

Where the compounds in accordance with the invention comprise an optionally substituted straight or branched alkylene chain, typical values thereof include methylene (—$CH_2$—), (methyl)methylene, ethylene (—$CH_2CH_2$—), (ethyl)methylene, (dimethyl)-methylene, (methyl)ethylene, propylene (—$CH_2CH_2CH_2$—), (propyl)methylene and (dimethyl)ethylene, any of which chains may be optionally substituted by one or more substituents. Suitably, such chains are unsubstituted, monosubstituted or disubstituted. Typically, such chains are unsubstituted or monosubstituted. In one embodiment, such chains are unsubstituted. In another embodiment, such chains are monosubstituted. In a further embodiment, such chains are disubstituted.

Examples of typical substituents on the alkylene chain which may be present in a compound in accordance with the invention include halogen, cyano, trifluoromethyl, oxo, hydroxy, $C_{1-6}$ alkoxy, carboxy($C_{1-6}$)alkoxy, trifluoromethoxy, amino, $C_{1-6}$ alkylamino, di($C_{1-6}$)alkylamino, $C_{2-6}$ alkylcarbonylamino, carboxy, benzyloxycarbonyl, tetrazolyl, aminocarbonyl, $C_{1-6}$ alkylaminocarbonyl and di($C_{1-6}$)alkylaminocarbonyl.

Specific examples of suitable substituents on the alkylene chain which may be present in a compound in accordance with the invention include fluoro, cyano, trifluoromethyl, hydroxy, methoxy, carboxymethoxy, amino, acetylamino, carboxy, benzyloxycarbonyl and tetrazolyl.

In a first embodiment, Q represents a covalent bond, whereby the integer Z is attached directly to the imidazole or pyrazole ring.

In a second embodiment, Q represents —O—, —S—, —S(O)—, —S(O)$_2$—, —S(O)(NR$^6$)—, —N(R$^6$)—, —C(O)N(R$^6$)—, —N(R$^6$)C(O)—, —S(O)$_2$N(R$^6$)— or —N(R$^6$)S(O)$_2$—. In a first aspect of that embodiment, Q represents —O—. In a second aspect of that embodiment, Q represents —S—. In a third aspect of that embodiment, Q represents —S(O)—. In a fourth aspect of that embodiment, Q represents —S(O)$_2$—. In a fifth aspect of that embodiment, Q represents —S(O)(NR$^6$)—. In a sixth aspect of that embodiment, Q represents —N(R$^6$)—. In a seventh aspect of that embodiment, Q represents —C(O)N(R$^6$)—. In an eighth aspect of that embodiment, Q represents —N(R$^6$)C(O)—. In a ninth aspect of that embodiment, Q represents —S(O)$_2$N(R$^6$)—. In a tenth aspect of that embodiment, Q represents —N(R$^6$)S(O)$_2$—.

In a third embodiment, Q represents an optionally substituted straight or branched $C_{1-6}$ alkylene chain optionally comprising one, two or three heteroatom-containing linkages independently selected from —O—, —S—, —S(O)—, —S(O)$_2$—, —S(O)(NR$^6$)—, —N(R$^6$)—, —C(O)N(R$^6$)—, —N(R$^6$)C(O)—, —S(O)$_2$N(R$^6$)— and —N(R$^6$)S(O)$_2$—. In a first aspect of that embodiment, Q represents an optionally substituted straight or branched $C_{1-6}$ alkylene chain. In a second aspect of that embodiment, Q represents an optionally substituted straight or branched $C_{1-6}$ alkylene chain comprising one heteroatom-containing linkage independently selected from —O—, —S—, —S(O)—, —S(O)$_2$—, —S(O)(NR$^6$)—, —N(R$^6$)—, —C(O)N(R$^6$)—, —N(R$^6$)C(O)—, —S(O)$_2$N(R$^6$)— and —N(R$^6$)S(O)$_2$—. In a third aspect of that embodiment, Q represents an optionally substituted straight or branched $C_{1-6}$ alkylene chain comprising two heteroatom-containing linkages independently selected from —O—, —S—, —S(O)—, —S(O)$_2$—, —S(O)(NR$^6$)—, —N(R$^6$)—, —C(O)N(R$^6$)—, —N(R$^6$)C(O)—, —S(O)$_2$N(R$^6$)— and —N(R$^6$)S(O)$_2$—. In a fourth aspect of that embodiment, Q represents an optionally substituted straight or branched $C_{1-6}$ alkylene chain comprising three heteroatom-containing linkages independently selected from —O—, —S—, —S(O)—, —S(O)$_2$—, —S(O)(NR$^6$)—, —N(R$^6$)—, —C(O)N(R$^6$)—, —N(R$^6$)C(O)—, —S(O)$_2$N(R$^6$)— and —N(R$^6$)S(O)$_2$—. In a fifth aspect of that embodiment, Q represents an optionally substituted straight or branched $C_{1-6}$ alkylene chain comprising one, two or three heteroatom-containing linkages independently selected from —O—, —S—, —N(R$^6$)—, —C(O)N(R$^6$)— and —N(R$^6$)C(O)—.

Typically, Q represents a covalent bond; or Q represents —S(O)— or —S(O)$_2$—; or Q represents an optionally substituted straight or branched $C_{1-6}$ alkylene chain optionally comprising one or two heteroatom-containing linkages selected from —O—, —S—, —N(R$^6$)—, —C(O)N(R$^6$)—, and —N(R$^6$)C(O)—.

Selected examples of typical substituents on the linkage represented by Q include halogen, cyano, trifluoromethyl, hydroxy, $C_{1-6}$ alkoxy and amino.

Specific examples of typical substituents on the linkage represented by Q include fluoro, cyano, trifluoromethyl, hydroxy, methoxy and amino.

Suitably, Q represents a covalent bond; or Q represents —S(O)—, —S(O)$_2$— or —N(R$^6$)—; or Q represents —$CH_2$—, —CH(F)—, —$CF_2$—, —CH(CN)—, —CH($CH_3$)—, —CH(OH)—, —CH($CH_2OH$)—, —CH($OCH_3$)—, —CH($NH_2$)—, —$CH_2CH_2$—, —CH(OH)$CH_2$—, —CH(OH)$CF_2$—, —CH($OCH_3$)$CH_2$—, —$CH_2O$—, —CH($CH_3$)O—, —C($CH_3$)$_2$O—, —CH($CH_2CH_3$)O—, —CH($CF_3$)O—, —$CH_2S$—, —$CH_2S(O)$—, —$CH_2S(O)_2$—, —$CH_2N(R^6)$—, —$CH_2CH_2CH_2$—, —CH(OH)$CH_2CH_2$—, —CH($OCH_3$)$CH_2CH_2$—, —$CH_2CH_2O$—, —$CH_2OCH_2$—, —$CH_2OCH(F)$—, —$CH_2OCF_2$—, —$CH_2OCH(CH_3)$—, —CH($CH_3$)$OCH_2$—, —$CH_2OC(CH_3)_2$—, —C($CH_3$)$_2OCH_2$—, —$CH_2SCH_2$—, —$CH_2S(O)CH_2$—, —$CH_2S(O)_2CH_2$—, —$CH_2CH_2N(R^6)$—, —$CH_2N(R^6)CH_2$—, —$CH_2N(R^6)C(O)$—, —$CH_2CH_2OCH_2$—, —$CH_2CH_2N(R^6)C(O)$—, —$CH_2OCH_2CH_2$—, —$CH_2OCH_2CF_2$—, —$CH_2OCH_2CH(CH_3)$—, —$CH_2OCH(CH_3)CH_2$—, —$CH_2OC(CH_3)_2CH_2$—, —$CH_2OCH_2CH(CH_3)CH_2$—, —$CH_2OCH_2CH_2O$—, —$CH_2OCH_2C(O)N(R^6)$— or —$CH_2OCH_2CH_2OCH_2$—.

Appositely, Q represents a covalent bond; or Q represents —$CH_2$—, —CH(CN)—, —CH(OH)—, —CH($OCH_3$)—, —$CH_2O$—, —$CH_2N(R^6)$— or —$CH_2OCH_2$—.

More suitably, Q represents a covalent bond; or Q represents —$CH_2$— or —$CH_2O$—.

Generally, Q represents a covalent bond; or Q represents —$CH_2$—.

Particular values of Q include —$CH_2$—, —CH(OH)—, —$CH_2O$—, —$CH_2S$— and —$CH_2OCH_2$—. In a first embodiment, Q represents —$CH_2$—. In a second embodiment, Q represents —CH(OH)—. In a third embodiment, Q represents —$CH_2O$—. In a fourth embodiment, Q represents —$CH_2S$—. In a fifth embodiment, Q represents —$CH_2OCH_2$—.

In one embodiment, Z represents hydrogen.

In another embodiment, Z is other than hydrogen.

In a selected embodiment, Z represents hydrogen; or Z represents $C_{1-6}$ alkyl, $C_{3-7}$ cycloalkyl, aryl, $C_{3-7}$ heterocycloalkyl, $C_{3-7}$ heterocycloalkenyl or heteroaryl, any of which groups may be optionally substituted by one or more substituents; or Z represents —$Z^1$—$Z^2$ or —$Z^1$—C(O)—$Z^2$, either of which moieties may be optionally substituted by one or more substituents.

In a further embodiment, Z represents $C_{1-6}$ alkyl, $C_{3-7}$ cycloalkyl, aryl, $C_{3-7}$ heterocycloalkyl, $C_{3-7}$ heterocycloalkenyl or heteroaryl, any of which groups may be optionally substituted by one or more substituents; or Z represents —Z¹-Z² or —Z¹—C(O)—Z², either of which moieties may be optionally substituted by one or more substituents.

Suitably, Z represents hydrogen; or Z represents $C_{1-6}$ alkyl, aryl or heteroaryl, any of which groups may be optionally substituted by one or more substituents; or Z represents —Z¹-Z², which moiety may be optionally substituted by one or more substituents.

Appositely, Z represents hydrogen; or Z represents $C_{1-6}$ alkyl, which group may be optionally substituted by one or more substituents.

Typically, Z represents hydrogen, fluoro or trifluoromethyl; or Z represents methyl, ethyl, n-propyl, isopropyl, n-butyl, sec-butyl, isobutyl, tert-butyl, cyclopropyl, cyclobutyl, cyclopentyl, cyclohexyl, phenyl, tetrahydrofuranyl, pyrrolidinyl, indolinyl, tetrahydropyranyl, piperidinyl, 1,2,3,4-tetrahydroquinolinyl, morpholinyl, azocanyl, thiazolinyl, furyl, thienyl, pyrazolyl, 4,5,6,7-tetrahydroindazolyl, benzoxazolyl, isoxazolyl, thiazolyl, benzothiazolyl, imidazolyl, benzimidazolyl, [1,2,4]triazolo[1,5-a]-pyrimidinyl, tetrazolyl, pyridinyl, quinolinyl, isoquinolinyl, phthalazinyl, pyrimidinyl or pyrazinyl, any of which groups may be optionally substituted by one or more substituents; or Z represents —Z¹-Z² or —Z¹—C(O)—Z², either of which moieties may be optionally substituted by one or more substituents.

The moiety $Z^1$ represents a divalent radical derived from an aryl, $C_{3-7}$ heterocycloalkyl or heteroaryl group, any of which groups may be optionally substituted by one or more substituents. Typically, the moiety $Z^1$ represents a divalent radical derived from a phenyl, pyrrolidinyl, piperazinyl, pyrazolyl, thiazolyl, triazolyl, tetrazolyl or pyridinyl group, any of which groups may be optionally substituted by one or more substituents. Typical values of the moiety $Z^1$ include the groups of formula (Za), (Zb), (Zc), (Zd), (Ze), (Zf), (Zg), (Zh), (Zj) and (Zk):

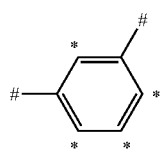

(Za)

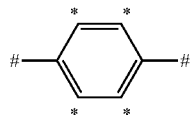

(Zb)

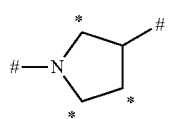

(Zc)

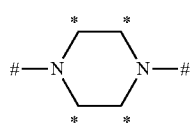

(Zd)

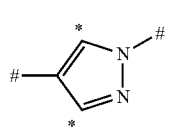

(Ze)

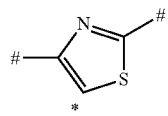

(Zf)

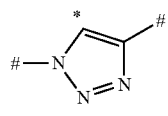

(Zg)

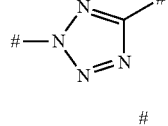

(Zh)

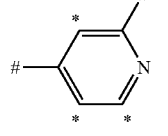

(Zj)

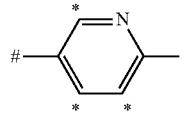

(Zk)

wherein
the symbols # represent the points of attachment of the moiety $Z^1$ to the remainder of the molecule; and
the asterisks (*) represent the site of attachment of optional substituents.

Particular values of the moiety $Z^1$ include the groups of formula (Za), (Zc), (Ze), (Zf), (Zg), (Zh) and (Zj) as depicted above.

The moiety $Z^2$ represents aryl, $C_{3-7}$ heterocycloalkyl, $C_{3-7}$ heterocycloalkenyl or heteroaryl, any of which groups may be optionally substituted by one or more substituents. Typically, $Z^2$ represents phenyl, pyrrolidinyl, oxazolidinyl, imidazolidinyl, morpholinyl, imidazolinyl, thiazolyl, imidazolyl, tetrazolyl or pyridinyl, any of which groups may be optionally substituted by one or more substituents.

Examples of optional substituents which may be present on the moiety Z, $Z^1$ or $Z^2$ include one, two or three substituents independently selected from halogen, cyano, nitro, $C_{1-6}$ alkyl, trifluoromethyl, oxo, hydroxy, hydroxy($C_{1-6}$)alkyl, $C_{1-6}$ alkoxy, difluoromethoxy, trifluoromethoxy, $C_{1-3}$ alkylenedioxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, di($C_{1-6}$)alkylamino($C_{1-6}$)alkyl, $C_{2-6}$ alkylcarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl, di($C_{1-6}$)alkylaminosulfonyl, aminocarbonylamino and hydrazinocarbonyl.

Examples of particular substituents on the moiety Z, $Z^1$ or $Z^2$ include fluoro, chloro, bromo, cyano, nitro, methyl, ethyl, isopropyl, trifluoromethyl, oxo, hydroxy, hydroxymethyl, methoxy, difluoromethoxy, trifluoromethoxy, methylenedioxy, methylthio, methylsulfinyl, methylsulfonyl, amino, methylamino, tert-butylamino, dimethylamino, dimethylaminomethyl, dimethylaminoethyl, acetylamino, methylsulfonylamino, formyl, acetyl, carboxy, methoxycarbonyl, tert-butoxycarbonyl, aminocarbonyl, methylaminocarbonyl, dimethylaminocarbonyl, aminosulfonyl, methylaminosulfonyl, dimethylaminosulfonyl, aminocarbonylamino and hydrazinocarbonyl.

Typical values of $Z^2$ include phenyl, hydroxyphenyl, oxopyrrolidinyl, dioxopyrrolidinyl, (hydroxy)(oxo)pyrrolidinyl, (amino)(oxo)pyrrolidinyl, (oxo)oxazolidinyl, oxoimidazolidinyl, morpholinyl, imidazolinyl, methylthiazolyl, formylthiazolyl, imidazolyl, tetrazolyl and pyridinyl.

Selected values of $Z^2$ include oxopyrrolidinyl and (oxo)oxazolidinyl. In one embodiment, $Z^2$ represents oxopyrrolidinyl. In another embodiment, $Z^2$ represents (oxo)oxazolidinyl.

Typical values of Z include hydrogen, fluoro, trifluoromethyl, methyl, ethyl, n-propyl, isopropyl, isobutyl, tert-butyl, cyclopropyl, cyclopentyl, cyclohexyl, oxocyclohexyl, phenyl, bromophenyl, cyanophenyl, nitrophenyl, methoxyphenyl, difluoromethoxyphenyl, trifluoromethoxyphenyl, methylenedioxyphenyl, methylsulfonylphenyl, dimethylaminophenyl, acetylaminophenyl, methylsulfonylaminophenyl, carboxyphenyl, aminocarbonylphenyl, methylaminocarbonylphenyl, dimethylaminocarbonylphenyl, aminocarbonylaminophenyl, tetrahydrofuranyl, oxopyrrolidinyl, dimethylaminopyrrolidinyl, tert-butoxycarbonylpyrrolidinyl, indolinyl, tetrahydropyranyl, piperidinyl, ethylpiperidinyl, tert-butoxycarbonylpiperidinyl, aminocarbonylpiperidinyl, 2-oxo-3,4-dihydroquinolinyl, morpholinyl, azocanyl, oxothiazolinyl, furyl, hydroxymethylfuryl, thienyl, methylpyrazolyl, dimethylpyrazolyl, 4,5,6,7-tetrahydroindazolyl, benzoxazolyl, methylisoxazolyl, dimethylisoxazolyl, methylthiazolyl, aminothiazolyl, benzothiazolyl, methylbenzothiazolyl, aminobenzothiazolyl, imidazolyl, methylimidazolyl, methylbenzimidazolyl, dimethyl[1,2,4]triazolo[1,5-a]pyrimidinyl, dimethylaminoethyltetrazolyl, pyridinyl, fluoropyridinyl, chloropyridinyl, cyanopyridinyl, methylpyridinyl, (cyano)-(methyl)pyridinyl, trifluoromethylpyridinyl, oxopyridinyl, methoxypyridinyl, methylsulfonylpyridinyl, dimethylaminomethylpyridinyl, acetylaminopyridinyl, carboxypyridinyl, methoxycarbonylpyridinyl, aminocarbonylpyridinyl, (aminocarbonyl)(fluoro)-pyridinyl, methylaminocarbonylpyridinyl, dimethylaminocarbonylpyridinyl, hydrazinocarbonylpyridinyl, quinolinyl, isoquinolinyl, (methyl)(oxo)phthalazinyl, pyrimidinyl, pyrazinyl, oxopyrrolidinylphenyl, dioxopyrrolidinylphenyl, (hydroxy)(oxo)pyrrolidinylphenyl, (amino)(oxo)pyrrolidinylphenyl, (oxo)oxazolidinylphenyl, oxoimidazolidinylphenyl, imidazolinylphenyl, methylthiazolylphenyl, formylthiazolylphenyl, imidazolylphenyl, tetrazolylphenyl, phenylpyrrolidinyl, hydroxyphenylpiperazinyl, (methyl)-(phenyl)pyrazolyl, oxoimidazolidinylthiazolyl, hydroxyphenyltriazolyl, morpholinyltetrazolyl, oxopyrrolidinylpyridinyl, (oxo)oxazolidinylpyridinyl, oxoimidazolidinylpyridinyl, pyridinylthiazolyl, pyridinyltetrazolyl and morpholinylcarbonylphenyl.

Particular values of Z include hydrogen, methyl, methylsulfonylphenyl, pyridinyl, methylsulfonylpyridinyl, oxopyrrolidinylphenyl, (hydroxy)(oxo)pyrrolidinylphenyl and (oxo)oxazolidinylphenyl. In a first embodiment, Z represents hydrogen. In a second embodiment, Z represents methyl. In a third embodiment, Z represents methylsulfonylphenyl. In one aspect of that embodiment, Z represents 3-(methylsulfonyl)phenyl. In another aspect of that embodiment, Z represents 4-(methylsulfonyl)phenyl. In a fourth embodiment, Z represents pyridinyl. In one aspect of that embodiment, Z represents pyridin-4-yl. In a fifth embodiment, Z represents oxopyrrolidinylphenyl. In one aspect of that embodiment, Z represents 3-(2-oxo-pyrrolidin-1-yl)phenyl. In a sixth embodiment, Z represents (hydroxy)(oxo)pyrrolidinylphenyl. In one aspect of that embodiment, Z represents 3-(3-hydroxy-2-oxopyrrolidin-1-yl)phenyl. In another aspect of that embodiment, Z represents 3-(4-hydroxy-2-oxo-pyrrolidin-1-yl)phenyl. In a seventh embodiment, Z represents (oxo)oxazolidinylphenyl. In one aspect of that embodiment, Z represents 3-(2-oxooxazolidinyl-3-yl)phenyl. In an eighth embodiment, Z represents methylsulfonylpyridinyl.

Selected values of Z include hydrogen and methyl.

Suitably, $R^1$, $R^2$, $R^3$ and $R^4$ independently represent hydrogen, halogen, cyano, trifluoromethyl or —$CO_2R^d$; or $C_{1-6}$ alkyl, $C_{2-6}$ alkynyl, aryl, $C_{3-7}$ heterocycloalkyl, $C_{3-7}$ heterocycloalkenyl, heteroaryl, ($C_{3-7}$)heterocycloalkyl($C_{1-6}$)alkyl-aryl-, heteroaryl-($C_{3-7}$)heterocycloalkyl-, ($C_{3-7}$)cycloalkyl-heteroaryl-, ($C_{3-7}$)cycloalkyl($C_{1-6}$)alkyl-heteroaryl-, ($C_{4-7}$)cycloalkenyl-heteroaryl-, ($C_{4-9}$)bicycloalkyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents.

Examples of optional substituents which may be present on $R^1$, $R^2$, $R^3$ or $R^4$ include one, two or three substituents independently selected from halogen, halo-($C_{1-6}$)alkyl, cyano, cyano($C_{1-6}$)alkyl, nitro, nitro($C_{1-6}$)alkyl, $C_{1-6}$ alkyl, difluoromethyl, trifluoromethyl, difluoroethyl, trifluoroethyl, $C_{2-6}$ alkenyl, hydroxy, hydroxy($C_{1-6}$)alkyl, $C_{1-6}$ alkoxy, difluoromethoxy, trifluoromethoxy, trifluoroethoxy, carboxy($C_{3-7}$)cycloalkyloxy, $C_{1-3}$ alkylenedioxy, $C_{1-6}$ alkoxy($C_{1-6}$)alkyl, $C_{1-6}$ alkylthio, $C_{1-6}$ alkylsulphinyl, $C_{1-6}$ alkylsulphonyl, ($C_{1-6}$)alkylsulphonyl($C_{1-6}$)alkyl, oxo, amino, amino($C_{1-6}$)alkyl, $C_{1-6}$ alkylamino, di($C_{1-6}$)alkylamino, hydroxy($C_{1-6}$)alkylamino, $C_{1-6}$ alkoxyamino, ($C_{1-6}$) alkoxy-($C_{1-6}$)alkylamino, [($C_{1-6}$)alkoxy](hydroxy)($C_{1-6}$) alkylamino, [($C_{1-6}$)alkylthio](hydroxy)-($C_{1-6}$)alkylamino, N—[($C_{1-6}$)alkyl]-N-[hydroxy($C_{1-6}$)alkyl]amino, di($C_{1-6}$) alkylamino-($C_{1-6}$)alkylamino, N-[di($C_{1-6}$)alkylamino($C_{1-6}$) alkyl]-N-[hydroxy($C_{1-6}$)alkyl]amino, hydroxy($C_{1-6}$)alkyl ($C_{3-7}$)cycloalkylamino, (hydroxy) [($C_{3-7}$)cycloalkyl($C_{1-6}$) alkyl]amino, ($C_{3-7}$)heterocycloalkyl($C_{1-6}$)alkylamino, oxo ($C_{3-7}$)heterocycloalkyl($C_{1-6}$)alkylamino, ($C_{1-6}$) alkylheteroarylamino, heteroaryl($C_{1-6}$)alkylamino, ($C_{1-6}$) alkylheteroaryl($C_{1-6}$)alkylamino, $C_{2-6}$ alkylcarbonylamino, N—[($C_{1-6}$)alkyl]-N—[($C_{2-6}$)alkylcarbonyl]amino, ($C_{2-6}$) alkylcarbonylamino($C_{1-6}$)alkyl, $C_{3-6}$ alkenylcarbonylamino, bis[($C_{3-6}$)alkenylcarbonyl]amino, N—[($C_{1-6}$)alkyl]-N—[($C_{3-7}$)cycloalkylcarbonyl]amino, $C_{2-6}$ alkoxycarbonylamino, $C_{2-6}$ alkoxycarbonyl($C_{1-6}$)alkylamino, $C_{1-6}$ alkylaminocarbonylamino, $C_{1-6}$ alkylsulphonylamino, N—[($C_{1-6}$)alkyl]-N—[($C_{1-6}$)alkylsulphonyl]amino, bis[($C_{1-6}$) alkylsulphonyl]amino, N—[($C_{1-6}$)alkyl]-N-[carboxy($C_{1-6}$) alkyl]amino, carboxy($C_{3-7}$)cycloalkylamino, carboxy-($C_{3-7}$) cycloalkyl($C_{1-6}$)alkylamino, formyl, $C_{2-6}$ alkylcarbonyl, ($C_{3-7}$)cycloalkylcarbonyl, phenylcarbonyl, ($C_{2-6}$)alkylcarbonyloxy($C_{1-6}$)alkyl, carboxy, carboxy($C_{1-6}$)alkyl, $C_{2-6}$ alkoxycarbonyl, $C_{2-6}$ alkoxycarbonyl($C_{1-6}$)alkyl, morpholinyl($C_{1-6}$)alkoxycarbonyl, $C_{2-6}$ alkoxycarbonylmethylidenyl, a carboxylic acid isostere or prodrug moiety Ω, —($C_{1-6}$) alkyl-Ω, aminocarbonyl, $C_{1-6}$ alkylaminocarbonyl, hydroxy ($C_{1-6}$)alkylaminocarbonyl, di($C_{1-6}$)alkylaminocarbonyl, aminocarbonyl($C_{1-6}$)alkyl, aminosulphonyl, di($C_{1-6}$)alkylaminosulphonyl, ($C_{1-6}$)alkylsulphoximinyl and [($C_{1-6}$) alkyl][N—($C_{1-6}$)alkyl]-sulphoximinyl.

By the expression "carboxylic acid isostere or prodrug moiety" is meant any functional group, structurally distinct from a carboxylic acid moiety, that will be recognised by a biological system as being similar to, and thus capable of mimicking, a carboxylic acid moiety, or will be readily convertible by a biological system in vivo into a carboxylic acid moiety. A synopsis of some common carboxylic acid isosteres is presented by N. A. Meanwell in *J. Med. Chem.*, 2011, 54, 2529-2591 (cf. in particular FIGS. 25 and 26). An alternative carboxylic acid isostere is described by N Pemberton et al. in *ACS Med. Chem. Lett.*, 2012, 3, 574-578. Typical examples of suitable carboxylic acid isostere or prodrug moieties represented by Q include the functional groups of formula (i) to (xliii):

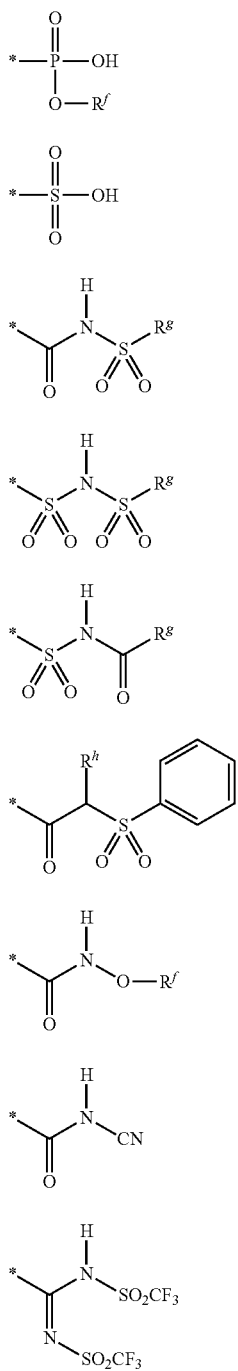
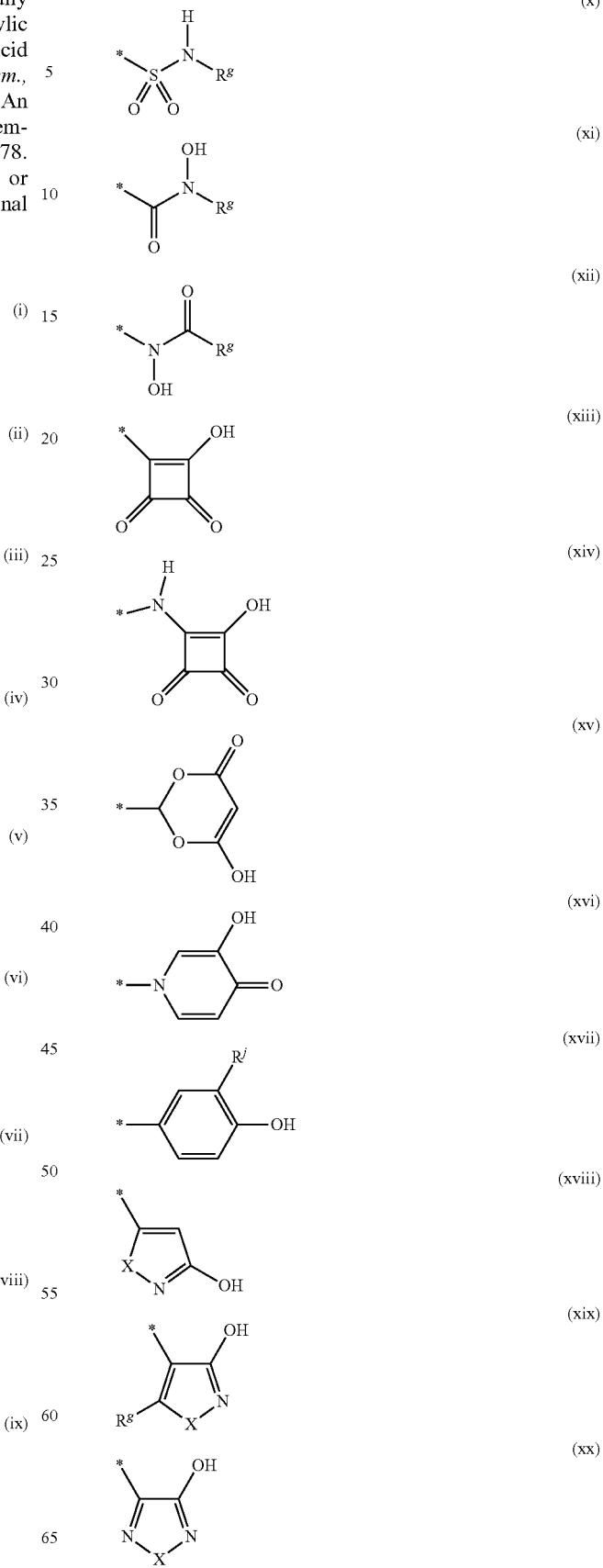

-continued
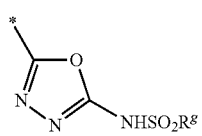 (xxi)
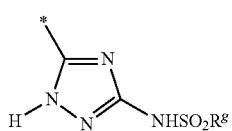 (xxii)
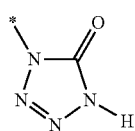 (xxiii)
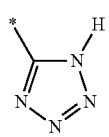 (xxiv)
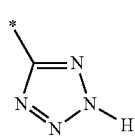 (xxv)
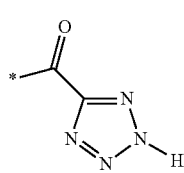 (xxvi)
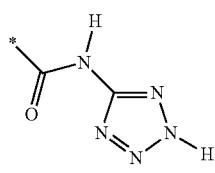 (xxvii)
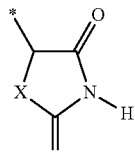 (xxviii)
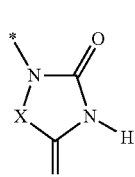 (xxix)
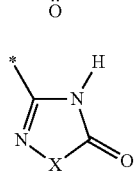 (xxx)
-continued
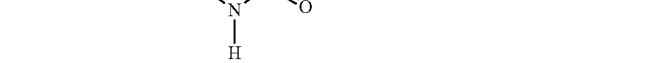 (xxxi)
 (xxxii)
 (xxxiii)
 (xxxiv)
 (xxxv)
 (xxxvi)
 (xxxvii)
 (xxxviii)
 (xxxix)
 (xl)

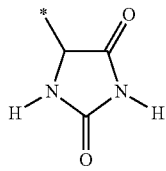

(xli)

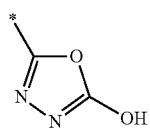

(xlii)

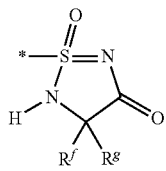

(xliii)

wherein the asterisk (*) represents the site of attachment to the remainder of the molecule;

n is zero, 1 or 2;

X represents oxygen or sulphur;

$R^f$ represents hydrogen, $C_{1-6}$ alkyl or —$CH_2CH(OH)CH_2OH$;

$R^g$ represents $C_{1-6}$ alkyl, trifluoromethyl, —$CH_2CH_2F$, —$CH_2CHF_2$, —$CH_2CF_3$ or —$CF_2CF_3$;

$R^h$ represents hydrogen, cyano or —$CO_2R^d$, in which $R^d$ is as defined above; and $R^j$ represents hydrogen or halogen.

In one embodiment, n is zero. In another embodiment, n is 1. In a further embodiment, n is 2.

In one embodiment, X represents oxygen. In another embodiment, X represents sulphur.

In one embodiment, $R^f$ represents hydrogen. In another embodiment, $R^f$ represents $C_{1-6}$ alkyl, especially methyl. In a further embodiment, $R^f$ is —$CH_2CH(OH)CH_2OH$.

In one embodiment, $R^g$ represents $C_{1-6}$ alkyl, especially methyl. In another embodiment, $R^g$ represents trifluoromethyl, —$CH_2CH_2F$, —$CH_2CHF_2$, —$CH_2CF_3$ or —$CF_2CF_3$. In a first aspect of that embodiment, $R^g$ represents trifluoromethyl. In a second aspect of that embodiment, $R^g$ represents —$CH_2CH_2F$. In a third aspect of that embodiment, $R^g$ represents —$CH_2CHF_2$. In a fourth aspect of that embodiment, $R^g$ represents —$CH_2CF_3$. In a fifth aspect of that embodiment, $R^g$ represents —$CF_2CF_3$.

In one embodiment, $R^h$ is hydrogen. In another embodiment, $R^h$ represents cyano. In a further embodiment, $R^h$ represents —$CO_2R^d$, especially methoxycarbonyl.

In one embodiment, $R^j$ represents hydrogen. In another embodiment, $R^j$ represents halogen, especially chloro.

In a selected embodiment, Ω represents tetrazolyl, especially a C-linked tetrazolyl moiety of formula (xxiv) or (xxv) as depicted above, in particular a group of formula (xxiv) as depicted above.

In another embodiment, Ω represents $C_{1-6}$ alkylsulphonylaminocarbonyl, i.e. a moiety of formula (iii) as depicted above wherein $R^g$ represents $C_{1-6}$ alkyl.

In another embodiment, Ω represents $C_{1-6}$ alkylaminosulphonyl, i.e. a moiety of formula (x) as depicted above wherein $R^g$ represents $C_{1-6}$ alkyl.

In a further embodiment, Ω represents $(C_{1-6})$alkylcarbonylaminosulphonyl, i.e. a moiety of formula (v) as depicted above wherein $R^g$ represents $C_{1-6}$ alkyl.

Typical examples of optional substituents which may be present on $R^1$, $R^2$, $R^3$ or $R^4$ include one, two or three substituents independently selected from $C_{1-6}$ alkyl, hydroxy$(C_{1-6})$alkyl, $C_{1-6}$ alkylsulphonyl, oxo, carboxy and $C_{2-6}$ alkoxycarbonyl.

Examples of particular substituents on $R^1$, $R^2$, $R^3$ or $R^4$ include fluoro, chloro, bromo, fluoromethyl, fluoroisopropyl, cyano, cyanoethyl, nitro, nitromethyl, methyl, ethyl, isopropyl, isobutyl, tert-butyl, difluoromethyl, trifluoromethyl, difluoroethyl, trifluoroethyl, ethenyl, hydroxy, hydroxymethyl, hydroxyisopropyl, methoxy, isopropoxy, difluoromethoxy, trifluoromethoxy, trifluoroethoxy, carboxycyclobutyloxy, methylenedioxy, ethylenedioxy, methoxymethyl, methoxyethyl, methylthio, methylsulphinyl, methylsulphonyl, methylsulphonylethyl, oxo, amino, aminomethyl, aminoisopropyl, methylamino, ethylamino, dimethylamino, hydroxyethylamino, hydroxypropylamino, (hydroxy)(methyl)propylamino, methoxyamino, methoxyethylamino, (hydroxy)-(methoxy)(methyl)propylamino, (hydroxy)(methylthio)butylamino, N-(hydroxyethyl)-N-(methyl)amino, dimethylaminoethylamino, (dimethylamino)(methyl)propylamino, N-(dimethylaminoethyl)-N-(hydroxyethyl)amino, hydroxymethylcyclopentylamino, hydroxycyclobutylmethylamino, (cyclopropyl)(hydroxy)propylamino, morpholinylethylamino, oxopyrrolidinylmethylamino, ethyloxadiazolylamino, methylthiadiazolylamino, thiazolylmethylamino, thiazolylethylamino, pyrimidinylmethylamino, methylpyrazolylmethylamino, acetylamino, N-acetyl-N-methylamino, N-isopropylcarbonyl-N-methylamino, acetylaminomethyl, ethenylcarbonylamino, bis(ethenylcarbonyl)amino, N-cyclopropylcarbonyl-N-methylamino, methoxycarbonylamino, ethoxycarbonylamino, tert-butoxycarbonylamino, methoxycarbonylethylamino, ethylaminocarbonylamino, butylaminocarbonylamino, methylsulphonylamino, N-methyl-N-(methylsulphonyl)amino, bis(methylsulphonyl)amino, N-(carboxymethyl)-N-methylamino, N-(carboxyethyl)-N-methylamino, carboxycyclopentylamino, carboxycyclopropylmethylamino, formyl, acetyl, isopropylcarbonyl, cyclobutylcarbonyl, phenylcarbonyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxycarbonylmethyl, ethoxycarbonylethyl, morpholinylethoxycarbonyl, ethoxycarbonylmethylidenyl, methylsulphonylaminocarbonyl, acetylaminosulphonyl, methoxyaminocarbonyl, tetrazolyl, tetrazolylmethyl, hydroxyoxadiazolyl, aminocarbonyl, methylaminocarbonyl, hydroxyethylaminocarbonyl, dimethylaminocarbonyl, aminocarbonylmethyl, aminosulphonyl, methylaminosulphonyl, dimethylaminosulphonyl, methylsulphoximinyl and (methyl)(N-methyl)sulphoximinyl.

Typical examples of particular substituents on $R^1$, $R^2$, $R^3$ or $R^4$ include methyl, hydroxyisopropyl, methylsulphonyl, oxo, carboxy, methoxycarbonyl and ethoxycarbonyl.

Typically, $R^1$ represents hydrogen, halogen, cyano or —$CO_2R^d$; or $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl$(C_{3-7})$heterocycloalkyl-, $(C_{3-7})$cycloalkyl-heteroaryl-, $(C_{3-7})$cycloalkyl$(C_{1-6})$alkyl-heteroaryl-, $(C_{4-7})$cycloalkenyl-heteroaryl-, $(C_{4-9})$bicycloalkyl-heteroaryl-, $(C_{3-7})$heterocycloalkyl-heteroaryl-, $(C_{3-7})$heterocycloalkyl$(C_{1-6})$alkyl-heteroaryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents.

Suitably, $R^1$ represents halogen, cyano or —$CO_2R^d$; or $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl($C_{1-6}$)alkyl-aryl-, heteroaryl($C_{3-7}$)heterocycloalkyl-, $(C_{3-7})$cycloalkyl-heteroaryl-, $(C_{3-7})$cycloalkyl($C_{1-6}$)alkyl-heteroaryl-, $(C_{4-7})$cycloalkenyl-heteroaryl-, $(C_{4-9})$bicycloalkyl-heteroaryl-, $(C_{3-7})$heterocycloalkyl-heteroaryl-, $(C_{3-7})$heterocycloalkyl($C_{1-6}$)alkyl-heteroaryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents.

Generally, $R^1$ represents halogen or cyano; or $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl($C_{1-6}$)alkyl-aryl-, heteroaryl($C_{3-7}$)heterocycloalkyl-, $(C_{3-7})$cycloalkyl-heteroaryl-, $(C_{3-7})$cycloalkyl-($C_{1-6}$)alkyl-heteroaryl-, $(C_{4-7})$cycloalkenyl-heteroaryl-, $(C_{4-9})$bicycloalkyl-heteroaryl-, $(C_{3-7})$heterocycloalkyl-heteroaryl-, $(C_{3-7})$heterocycloalkyl($C_{1-6}$)alkyl-heteroaryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents.

More generally, $R^1$ represents halogen; or $R^1$ represents aryl, heteroaryl, $(C_{3-7})$cycloalkyl-heteroaryl-, $(C_{4-9})$bicycloalkyl-heteroaryl-, $(C_{3-7})$heterocycloalkyl-heteroaryl- or $(C_{4-9})$heterobicycloalkyl-heteroaryl-, any of which groups may be optionally substituted by one or more substituents.

Still more generally, $R^1$ represents halogen; or $R^1$ represents aryl, heteroaryl, $(C_{4-9})$bicycloalkyl-heteroaryl-, $(C_{3-7})$heterocycloalkyl-heteroaryl- or $(C_{4-9})$heterobicycloalkyl-heteroaryl-, any of which groups may be optionally substituted by one or more substituents.

In a first embodiment, $R^1$ represents hydrogen.

In a second embodiment, $R^1$ represents halogen. In one aspect of that embodiment, $R^1$ represents bromo. In another aspect of that embodiment, $R^1$ represents iodo.

In a third embodiment, $R^1$ represents cyano.

In a fourth embodiment, $R^1$ represents —$CO_2R^d$.

In a fifth embodiment, $R^1$ represents optionally substituted $C_{1-6}$ alkyl. In one aspect of that embodiment, $R^1$ represents optionally substituted ethyl.

In a sixth embodiment, $R^1$ represents optionally substituted $C_{2-6}$ alkynyl. In one aspect of that embodiment, $R^1$ represents optionally substituted butynyl.

In a seventh embodiment, $R^1$ represents optionally substituted aryl. In one aspect of that embodiment, $R^1$ represents optionally substituted phenyl.

In an eighth embodiment, $R^1$ represents optionally substituted $C_{3-7}$ heterocycloalkyl.

In a ninth embodiment, $R^1$ represents optionally substituted $C_{3-7}$ heterocycloalkenyl.

In a tenth embodiment, $R^1$ represents optionally substituted heteroaryl. In selected aspects of that embodiment, $R^1$ represents benzofuryl, thienyl, indolyl, pyrazolyl, indazolyl, isoxazolyl, thiazolyl, imidazolyl, pyridinyl, quinolinyl, pyridazinyl, pyrimidinyl or pyrazinyl, any of which groups may be optionally substituted by one or more substituents.

In an eleventh embodiment, $R^1$ represents optionally substituted $(C_{3-7})$-heterocycloalkyl($C_{1-6}$)alkyl-aryl-. In a first aspect of that embodiment, $R^1$ represents optionally substituted pyrrolidinylmethylphenyl-. In a second aspect of that embodiment, $R^1$ represents optionally substituted piperazinylmethylphenyl-.

In a twelfth embodiment, $R^1$ represents optionally substituted heteroaryl($C_{3-7}$)-heterocycloalkyl-. In one aspect of that embodiment, $R^1$ represents optionally substituted pyridinylpiperazinyl-.

In a thirteenth embodiment, $R^1$ represents optionally substituted $(C_{3-7})$cycloalkyl-heteroaryl-. In a first aspect of that embodiment, $R^1$ represents optionally substituted cyclohexylpyrazolyl-. In a second aspect of that embodiment, $R^1$ represents optionally substituted cyclohexylpyridinyl-. In a third aspect of that embodiment, $R^1$ represents optionally substituted cyclopropylpyrimidinyl-. In a fourth aspect of that embodiment, $R^1$ represents optionally substituted cyclobutylpyrimidinyl-. In a fifth aspect of that embodiment, $R^1$ represents optionally substituted cyclopentylpyrimidinyl-. In a sixth aspect of that embodiment, $R^1$ represents optionally substituted cyclohexylpyrimidinyl-. In a seventh aspect of that embodiment, $R^1$ represents optionally substituted cyclohexylpyrazinyl-.

In a fourteenth embodiment, $R^1$ represents optionally substituted $(C_{4-7})$-cycloalkenyl-heteroaryl-.

In a fifteenth embodiment, $R^1$ represents optionally substituted $(C_{3-7})$-heterocycloalkyl-heteroaryl-. In a first aspect of that embodiment, $R^1$ represents optionally substituted pyrrolidinylpyridinyl-. In a second aspect of that embodiment, $R^1$ represents optionally substituted tetrahydropyranylpyridinyl-. In a third aspect of that embodiment, $R^1$ represents optionally substituted piperidinylpyridinyl-. In a fourth aspect of that embodiment, $R^1$ represents optionally substituted piperazinylpyridinyl-. In a fifth aspect of that embodiment, $R^1$ represents optionally substituted morpholinylpyridinyl-. In a sixth aspect of that embodiment, $R^1$ represents optionally substituted thiomorpholinylpyridinyl-. In a seventh aspect of that embodiment, $R^1$ represents optionally substituted diazepanylpyridinyl-. In an eighth aspect of that embodiment, $R^1$ represents optionally substituted oxetanylpyrimidinyl-. In a ninth aspect of that embodiment, $R^1$ represents optionally substituted azetidinylpyrimidinyl-. In a tenth aspect of that embodiment, $R^1$ represents optionally substituted tetrahydrofuranylpyrimidinyl-. In an eleventh aspect of that embodiment, $R^1$ represents optionally substituted pyrrolidinylpyrimidinyl-. In a twelfth aspect of that embodiment, $R^1$ represents optionally substituted tetrahydropyranylpyrimidinyl-. In a thirteenth aspect of that embodiment, $R^1$ represents optionally substituted piperidinylpyrimidinyl-. In a fourteenth aspect of that embodiment, $R^1$ represents optionally substituted piperazinylpyrimidinyl-. In a fifteenth aspect of that embodiment, $R^1$ represents optionally substituted morpholinylpyrimidinyl-. In a sixteenth aspect of that embodiment, $R^1$ represents optionally substituted thiomorpholinylpyrimidinyl-. In a seventeenth aspect of that embodiment, $R^1$ represents optionally substituted azepanylpyrimidinyl-. In an eighteenth aspect of that embodiment, $R^1$ represents optionally substituted oxazepanylpyrimidinyl-. In a nineteenth aspect of that embodiment, $R^1$ represents optionally substituted diazepanylpyrimidinyl-. In a twentieth aspect of that embodiment, $R^1$ represents optionally substituted thiadiazepanylpyrimidinyl-. In a twenty-first aspect of that embodiment, $R^1$ represents optionally substituted oxetanylpyrazinyl-. In a twenty-second aspect of that embodiment, $R^1$ represents optionally substituted piperidinylpyrazinyl-.

In a sixteenth embodiment, $R^1$ represents optionally substituted $(C_{3-7})$-heterocycloalkyl($C_{1-6}$)alkyl-heteroaryl-. In a first aspect of that embodiment, $R^1$ represents optionally substituted morpholinylmethylthienyl-. In a second aspect of that embodiment, $R^1$ represents optionally substituted morpholinylethylpyrazolyl-.

In a seventeenth embodiment, $R^1$ represents optionally substituted $(C_{3-7})$-heterocycloalkenyl-heteroaryl-.

In an eighteenth embodiment, $R^1$ represents optionally substituted $(C_{4-9})$-heterobicycloalkyl-heteroaryl-.

In a nineteenth embodiment, $R^1$ represents optionally substituted $(C_{4-9})$-spiroheterocycloalkyl-heteroaryl-.

In a twentieth embodiment, $R^1$ represents optionally substituted $(C_{3-7})$cycloalkyl-$(C_{1-6})$alkyl-heteroaryl-. In one aspect of that embodiment, $R^1$ represents optionally substituted cyclohexylmethylpyrimidinyl-.

In a twenty-first embodiment, $R^1$ represents optionally substituted $(C_{4-9})$-bicycloalkyl-heteroaryl-.

Appositely, $R^1$ represents hydrogen, bromo, iodo or —$CO_2R^d$; or ethyl, butynyl, phenyl, pyrrolidinyl, piperidinyl, piperazinyl, morpholinyl, 1,2,3,6-tetrahydropyridinyl, benzofuryl, thienyl, indolyl, pyrazolyl, indazolyl, isoxazolyl, thiazolyl, imidazolyl, pyridinyl, quinolinyl, pyridazinyl, pyrimidinyl, pyrazinyl, pyrrolidinylmethylphenyl, piperazinylmethylphenyl, pyridinylpiperazinyl, cyclohexylpyrazolyl, cyclohexylpyridinyl, cyclopropylpyrimidinyl, cyclobutylpyrimidinyl, cyclopentylpyrimidinyl, cyclohexylpyrimidinyl, cyclohexylpyrazinyl, cyclohexylmethylpyrimidinyl, cyclohexenylpyridinyl, cyclohexenylpyrimidinyl, bicyclo[3.1.0]hexanylpyridinyl, bicyclo[3.1.0]hexanylpyrimidinyl, bicyclo[4.1.0]heptanylpyrimidinyl, bicyclo[2.2.2]octanylpyrimidinyl, pyrrolidinylpyridinyl, tetrahydropyranylpyridinyl, piperidinylpyridinyl, piperazinylpyridinyl, morpholinylpyridinyl, thiomorpholinylpyridinyl, diazepanylpyridinyl, oxetanylpyrimidinyl, azetidinylpyrimidinyl, tetrahydrofuranylpyrimidinyl, pyrrolidinylpyrimidinyl, tetrahydropyranylpyrimidinyl, piperidinylpyrimidinyl, piperazinylpyrimidinyl, hexahydro-[1,2,5]thiadiazolo[2,3-a]pyrazinylpyrimidinyl, morpholinylpyrimidinyl, thiomorpholinylpyrimidinyl, azepanylpyrimidinyl, oxazepanylpyrimidinyl, diazepanylpyrimidinyl, thiadiazepanylpyrimidinyl, oxetanylpyrazinyl, piperidinylpyrazinyl, morpholinylmethylthienyl, morpholinylethylpyrazolyl, 3-azabicyclo[3.1.0]-hexanylpyridinyl, 3-azabicyclo[3.1.0]hexanylpyridazinyl, 3-azabicyclo[3.1.0]hexanylpyrimidinyl, 2-oxa-5-azabicyclo[2.2.1]heptanylpyrimidinyl, 3-azabicyclo[3.1.1]heptanylpyrimidinyl, 3-azabicyclo[4.1.0]heptanylpyrimidinyl, 3-azabicyclo[4.1.0]heptanylpyrimidinyl, 2-oxabicyclo[2.2.2]octanylpyrimidinyl, 3-azabicyclo[3.2.1]octanylpyrimidinyl, 8-azabicyclo[3.2.1]octanylpyrimidinyl, 3-oxa-8-azabicyclo[3.2.1]octanylpyrimidinyl, 3,6-diazabicyclo[3.2.2]nonanylpyrimidinyl, 3-oxa-7-azabicyclo[3.3.1]-nonanylpyrimidinyl, 5-azaspiro[2.3]hexanylpyrimidinyl, 5-azaspiro[2.4]heptanylpyrimidinyl, 2-azaspiro[3.3]heptanylpyrimidinyl, 2-oxa-6-azaspiro[3.3]heptanylpyrimidinyl, 2-oxa-6-azaspiro[3.4]octanylpyrimidinyl, 2-oxa-6-azaspiro[3.5]nonanylpyrimidinyl, 2-oxa-7-azaspiro[3.5]nonanylpyrimidinyl or 2,4,8-triazaspiro[4.5]decanylpyrimidinyl, any of which groups may be optionally substituted by one or more substituents.

More suitably, $R^1$ represents bromo or iodo; or $R^1$ represents phenyl, pyridinyl, pyrimidinyl, cyclohexylpyrimidinyl, bicyclo[3.1.0]hexanylpyridinyl, piperazinylpyridinyl, piperidinylpyridinyl, piperazinylpyrimidinyl, morpholinylpyrimidinyl, diazepanylpyrimidinyl or 3-azabicyclo[3.2.1]octanylpyrimidinyl, any of which groups may be optionally substituted by one or more substituents.

Illustratively, $R^1$ represents bromo or iodo; or $R^1$ represents phenyl, pyridinyl, pyrimidinyl, bicyclo[3.1.0]hexanylpyrimidinyl, piperazinylpyridinyl, piperidinylpyrimidinyl, piperazinylpyrimidinyl, morpholinylpyrimidinyl, diazepanylpyrimidinyl or 3-azabicyclo[3.2.1]octanylpyrimidinyl, any of which groups may be optionally substituted by one or more substituents.

Typical examples of optional substituents on $R^1$ include one, two or three substituents independently selected from halogen, halo$(C_{1-6})$alkyl, cyano, cyano$(C_{1-6})$alkyl, nitro$(C_{1-6})$alkyl, $C_{1-6}$ alkyl, trifluoromethyl, trifluoroethyl, $C_{2-6}$ alkenyl, hydroxy, hydroxy$(C_{1-6})$alkyl, $C_{1-6}$ alkoxy, trifluoroethoxy, carboxy$(C_{3-7})$cycloalkyloxy, $C_{1-6}$ alkylthio, $C_{1-6}$ alkylsulphonyl, $(C_{1-6})$alkylsulphonyl$(C_{1-6})$alkyl, oxo, amino, amino-$(C_{1-6})$alkyl, $C_{1-6}$ alkylamino, di$(C_{1-6})$alkylamino, $(C_{1-6})$alkoxy$(C_{1-6})$alkylamino, N—[$(C_{1-6})$alkyl]-N-[hydroxy$(C_{1-6})$alkyl]amino, $(C_{2-6})$alkylcarbonylamino$(C_{1-6})$alkyl, $C_{1-6}$ alkylsulphonylamino, N—[$(C_{1-6})$alkyl]-N—[$(C_{1-6})$alkylsulphonyl]amino, bis[$(C_{1-6})$alkylsulphonyl]amino, N—[$(C_{1-6})$alkyl]-N-[carboxy$(C_{1-6})$alkyl]amino, carboxy$(C_{3-7})$cycloalkylamino, carboxy$(C_{3-7})$cycloalkyl$(C_{1-6})$alkylamino, formyl, $C_{2-6}$ alkylcarbonyl, $(C_{2-6})$alkylcarbonyloxy$(C_{1-6})$alkyl, carboxy, carboxy$(C_{1-6})$alkyl, $C_{2-6}$ alkoxycarbonyl, $C_{2-6}$ alkoxycarbonyl$(C_{1-6})$alkyl, morpholinyl$(C_{1-6})$alkoxycarbonyl, $C_{2-6}$ alkoxycarbonylmethylidenyl, a carboxylic acid isostere or prodrug moiety Ω as defined herein, —$(C_{1-6})$alkyl-Ω, aminocarbonyl, aminosulphonyl, $(C_{1-6})$alkylsulphoximinyl and [$(C_{1-6})$alkyl][N—$(C_{1-6})$alkyl]sulphoximinyl.

Suitable examples of optional substituents on $R^1$ include one, two or three substituents independently selected from $C_{1-6}$ alkyl, hydroxy$(C_{1-6})$alkyl, $C_{1-6}$ alkylsulphonyl, oxo, carboxy and $C_{2-6}$ alkoxycarbonyl.

Typical examples of particular substituents on $R^1$ include one, two or three substituents independently selected from fluoro, chloro, fluoromethyl, fluoroisopropyl, cyano, cyanoethyl, nitromethyl, methyl, ethyl, isopropyl, trifluoromethyl, trifluoroethyl, ethenyl, hydroxy, hydroxymethyl, hydroxyisopropyl, methoxy, isopropoxy, trifluoroethoxy, carboxycyclobutyloxy, methylthio, methylsulphonyl, methylsulphonylethyl, oxo, amino, aminomethyl, aminoisopropyl, methylamino, dimethylamino, methoxyethylamino, N-(hydroxyethyl)-N-(methyl)amino, acetylaminomethyl, methylsulphonylamino, N-methyl-N-(methylsulphonyl)amino, bis(methylsulphonyl)amino, N-(carboxyethyl)-N-(methyl)amino, carboxycyclopentylamino, carboxycyclopropylmethylamino, formyl, acetyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxycarbonylmethyl, ethoxycarbonylethyl, morpholinylethoxycarbonyl, ethoxycarbonylmethylidenyl, methylsulphonylaminocarbonyl, acetylaminosulphonyl, methoxyaminocarbonyl, tetrazolyl, tetrazolylmethyl, hydroxyoxadiazolyl, aminocarbonyl, aminosulphonyl, methylsulphoximinyl and (methyl)(N-methyl)sulphoximinyl.

Suitable examples of particular substituents on $R^1$ include one, two or three substituents independently selected from methyl, hydroxyisopropyl, methylsulphonyl, oxo, carboxy, methoxycarbonyl and ethoxycarbonyl.

In a particular embodiment, $R^1$ is substituted by hydroxy$(C_{1-6})$alkyl. In one aspect of that embodiment, $R^1$ is substituted by hydroxyisopropyl, especially 2-hydroxyprop-2-yl.

Selected values of $R^1$ include hydrogen, bromo, iodo, —$CO_2R^d$, methoxycarbonylethyl, ethoxycarbonylethyl, hydroxybutynyl, chlorophenyl, hydroxyphenyl, methylsulphonylphenyl, aminomethylphenyl, aminoisopropylphenyl, acetylaminomethylphenyl, acetylphenyl, methoxycarbonylphenyl, aminocarbonylphenyl, aminosulphonylphenyl, acetylaminosulphonylphenyl, (methoxycarbonyl)(methyl)pyrrolidinyl, oxopiperidinyl, ethoxycarbonylpiperidinyl, methylsulphonylpiperazinyl, morpholinyl, methylsulphonyl-1,2,3,6-tetrahydropyridinyl, acetyl-1,2,3,6-tetrahydropyridinyl, tert-butoxycarbonyl-1,2,3,6-tetrahydropyridinyl, methoxycarbonylmethyl-1,2,3,6-tetrahydropyridinyl, benzofuryl, thienyl, indolyl, pyrazolyl, methylpyrazolyl, dimethylpyrazolyl, (methyl)[N-methyl-N-(methylsulfonyl) amino]pyrazolyl, methylindazolyl, dimethylisoxazolyl, hydroxyisopropylthiazolyl, methylimidazolyl, dimethylimidazolyl, pyridinyl, fluoropyridinyl, cyanopyridinyl, methylpyridinyl, (cyano)(methyl)pyridinyl, dimethylpyridinyl, trifluoromethylpyridinyl, ethenylpyridinyl, hydroxyisopropylpyridinyl, methoxypyridinyl, (methoxy)(methyl)pyridinyl, isopropoxypyridinyl, trifluoroethoxypyridinyl, (methyl)-(trifluoroethoxy)pyridinyl, methylsulphonylpyridinyl, oxopyridinyl, (methyl)(oxo)-pyridinyl, (dimethyl)(oxo)pyridinyl, aminopyridinyl, methylaminopyridinyl, dimethylaminopyridinyl, methoxyethylaminopyridinyl, N-(hydroxyethyl)-N-(methyl)aminopyridinyl, methylsulphonylaminopyridinyl, [bis(methylsulphonyl)amino]pyridinyl, carboxypyridinyl, quinolinyl, hydroxypyridazinyl, pyrimidinyl, fluoroisopropylpyrimidinyl, hydroxyisopropylpyrimidinyl, methoxypyrimidinyl, carboxycyclobutyloxypyrimidinyl, methylthiopyrimidinyl, methylsulphonylpyrimidinyl, oxopyrimidinyl, aminopyrimidinyl, dimethylaminopyrimidinyl, methoxyethylaminopyrimidinyl, N-(carboxyethyl)-N-(methyl)aminopyrimidinyl, carboxycyclopentylaminopyrimidinyl, carboxycyclopropylmethylaminopyrimidinyl, acetoxyisopropylpyrimidinyl, ethoxycarbonylethylpyrimidinyl, hydroxypyrazinyl, hydroxyisopropylpyrazinyl, pyrrolidinylmethylphenyl, piperazinylmethylphenyl, pyridinylpiperazinyl, carboxycyclohexylpyrazolyl, carboxycyclohexylpyridinyl, fluoromethylcyclopropylpyrimidinyl, acetylaminomethylcyclopropylpyrimidinyl, hydroxycyclobutylpyrimidinyl, carboxycyclopentylpyrimidinyl, carboxycyclohexylpyrimidinyl, (carboxy)(methyl)cyclohexylpyrimidinyl, (carboxy)(hydroxy)cyclohexylpyrimidinyl, carboxymethylcyclohexylpyrimidinyl, ethoxycarbonylcyclohexylpyrimidinyl, (methoxycarbonyl)(methyl)-cyclohexylpyrimidinyl, (ethoxycarbonyl)(methyl)cyclohexylpyrimidinyl, carboxycyclohexylpyrazinyl, carboxycyclohexylmethylpyrimidinyl, carboxycyclohexenylpyridinyl, carboxycyclohexenylpyrimidinyl, ethoxycarbonylcyclohexenylpyrimidinyl, carboxybicyclo[3.1.0]hexanylpyridinyl, carboxybicyclo[3.1.0]hexanylpyrimidinyl, ethoxycarbonylbicyclo[3.1.0]hexanylpyrimidinyl, carboxybicyclo[4.1.0]heptanylpyrimidinyl, carboxybicyclo[2.2.2]octanylpyrimidinyl, pyrrolidinylpyridinyl, hydroxypyrrolidinylpyridinyl, hydroxytetrahydropyranylpyridinyl, piperidinylpyridinyl, acetylpiperidinylpyridinyl, (carboxy)(methyl)piperidinylpyridinyl, [(carboxy)(methyl)-piperidinyl](fluoro)pyridinyl, [(carboxy)(methyl)piperidinyl](chloro)pyridinyl, piperazinylpyridinyl, (methyl)(piperazinyl)pyridinyl, cyanoethylpiperazinylpyridinyl, trifluoroethylpiperazinylpyridinyl, methylsulphonylpiperazinylpyridinyl, methylsulphonylethylpiperazinylpyridinyl, oxopiperazinylpyridinyl, acetylpiperazinylpyridinyl, (tert-butoxycarbonylpiperazinyl)(methyl)pyridinyl, carboxymethylpiperazinylpyridinyl, carboxyethylpiperazinylpyridinyl, ethoxycarbonylmethylpiperazinylpyridinyl, ethoxycarbonylethylpiperazinylpyridinyl, morpholinylpyridinyl, thiomorpholinylpyridinyl, oxothiomorpholinylpyridinyl, dioxothiomorpholinylpyridinyl, oxodiazepanylpyridinyl, fluorooxetanylpyrimidinyl, hydroxyoxetanylpyrimidinyl, hydroxyazetidinylpyrimidinyl, (hydroxy)(methyl)azetidinylpyrimidinyl, carboxyazetidinylpyrimidinyl, (tert-butoxycarbonyl)(hydroxy)azetidinylpyrimidinyl, tetrazolylazetidinylpyrimidinyl, hydroxytetrahydrofuranylpyrimidinyl, hydroxypyrrolidinylpyrimidinyl, carboxypyrrolidinylpyrimidinyl, (carboxy)(methyl)pyrrolidinylpyrimidinyl, carboxymethylpyrrolidinylpyrimidinyl, ethoxycarbonylpyrrolidinylpyrimidinyl, fluorotetrahydropyranylpyrimidinyl, hydroxytetrahydropyranylpyrimidinyl, difluoropiperidinylpyrimidinyl, (cyano)(methyl)piperidinylpyrimidinyl, (hydroxy)(nitromethyl)piperidinylpyrimidinyl, (hydroxy)(methyl)piperidinylpyrimidinyl, (hydroxy)(trifluoromethyl)-piperidinylpyrimidinyl, (hydroxymethyl)(methyl)piperidinylpyrimidinyl, methylsulphonylpiperidinylpyrimidinyl, oxopiperidinylpyrimidinyl, (formyl)(methyl)-piperidinylpyrimidinyl, carboxypiperidinylpyrimidinyl, (carboxy)(fluoro)piperidinylpyrimidinyl, (carboxy)(methyl)piperidinylpyrimidinyl, (carboxy)(ethyl)piperidinylpyrimidinyl, (carboxy)(trifluoromethyl)piperidinylpyrimidinyl, (carboxy)(hydroxy)-piperidinylpyrimidinyl, (carboxy)(hydroxymethyl)piperidinylpyrimidinyl, (carboxy)-(methoxy)piperidinylpyrimidinyl, (amino)(carboxy)piperidinylpyrimidinyl, carboxymethylpiperidinylpyrimidinyl, methoxycarbonylpiperidinylpyrimidinyl, ethoxycarbonylpiperidinylpyrimidinyl, (ethoxycarbonyl)(fluoro)piperidinylpyrimidinyl, (methoxycarbonyl)(methyl)piperidinylpyrimidinyl, (ethyl)(methoxycarbonyl)piperidinylpyrimidinyl, (isopropyl)(methoxycarbonyl)piperidinylpyrimidinyl, (ethoxycarbonyl)-(methyl)piperidinylpyrimidinyl, (n-butoxycarbonyl)(methyl)piperidinylpyrimidinyl, (ethoxycarbonyl)(trifluoromethyl)piperidinylpyrimidinyl, (ethoxycarbonyl)-(hydroxymethyl)piperidinylpyrimidinyl, (methoxy)(methoxycarbonyl)piperidinylpyrimidinyl, (carboxy)(methoxycarbonyl)piperidinylpyrimidinyl, (methyl)-(morpholinylethoxycarbonyl)piperidinylpyrimidinyl, ethoxycarbonylmethylpiperidinylpyrimidinyl, methylsulphonylaminocarbonylpiperidinylpyrimidinyl, acetylaminosulphonylpiperidinylpyrimidinyl, methoxyaminocarbonylpiperidinylpyrimidinyl, tetrazolylpiperidinylpyrimidinyl, hydroxyoxadiazolylpiperidinylpyrimidinyl, aminosulphonylpiperidinylpyrimidinyl, piperazinylpyrimidinyl, methylsulphonylpiperazinylpyrimidinyl, oxopiperazinylpyrimidinyl, carboxypiperazinylpyrimidinyl, carboxyethylpiperazinylpyrimidinyl, tert-butoxycarbonylpiperazinylpyrimidinyl, tetrazolylmethylpiperazinylpyrimidinyl, trioxohexahydro-[1,2,5]thiadiazolo[2,3-a]pyrazinylpyrimidinyl, morpholinylpyrimidinyl, dimethylmorpholinylpyrimidinyl, hydroxymethylmorpholinylpyrimidinyl, carboxymorpholinylpyrimidinyl, (carboxy)(methyl)morpholinylpyrimidinyl, carboxymethylmorpholinylpyrimidinyl, thiomorpholinylpyrimidinyl, dioxothiomorpholinylpyrimidinyl, carboxyazepanylpyrimidinyl, carboxyoxazepanylpyrimidinyl, oxodiazepanylpyrimidinyl, (oxodiazepanyl)(trifluoromethyl)pyrimidinyl, (oxodiazepanyl)(methoxy)pyrimidinyl, (methyl)(oxo)diazepanylpyrimidinyl, dioxothiadiazepanylpyrimidinyl, hydroxyoxetanylpyrazinyl, (carboxy)(methyl)piperidinylpyrazinyl, (ethoxycarbonyl)(methyl)piperidinylpyrazinyl, morpholinylmethylthienyl, morpholinylethylpyrazolyl, carboxy-3-azabicyclo[3.1.0]hexanylpyridinyl, carboxy-3-azabicyclo[3.1.0]hexanylpyridazinyl, carboxy-3-azabicyclo[3.1.0]hexanylpyrimidinyl, (carboxy)(methyl)-3-azabicyclo[3.1.0]hexanylpyrimidinyl, methoxycarbonyl-3-azabicyclo[3.1.0]hexanylpyrimidinyl, ethoxycarbonyl-3-azabicyclo[3.1.0]hexanylpyrimidinyl, 2-oxa-5-azabicyclo[2.2.1]heptanylpyrimidinyl, carboxy-2-oxa-5-azabicyclo-[2.2.1]heptanylpyrimidinyl, carboxy-3-azabicyclo[3.1.1]

heptanylpyrimidinyl, carboxy-3-azabicyclo[4.1.0]heptanylpyridinyl, carboxy-3-azabicyclo[4.1.0]heptanylpyrimidinyl, methoxycarbonyl-3-azabicyclo[4.1.0]heptanylpyrimidinyl, ethoxycarbonyl-3-azabicyclo-[4.1.0]heptanylpyrimidinyl, (hydroxy)(methyl)(oxo)-2-oxabicyclo[2.2.2]octanylpyrimidinyl, carboxy-3-azabicyclo[3.2.1]octanylpyrimidinyl, methoxycarbonyl-3-azabicyclo[3.2.1]octanylpyrimidinyl, oxo-8-azabicyclo[3.2.1]octanylpyrimidinyl, ethoxycarbonylmethylidenyl-8-azabicyclo[3.2.1]octanylpyrimidinyl, 3-oxa-8-azabicyclo-[3.2.1]octanylpyrimidinyl, oxo-3,6-diazabicyclo[3.2.2]nonanylpyrimidinyl, carboxy-3-oxa-7-azabicyclo[3.3.1]nonanylpyrimidinyl, carboxy-5-azaspiro[2.3]hexanylpyrimidinyl, (carboxy)(methyl)-5-azaspiro[2.3]hexanylpyrimidinyl, carboxy-5-azaspiro[2.4]heptanylpyrimidinyl, carboxy-2-azaspiro[3.3]heptanylpyrimidinyl, 2-oxa-6-azaspiro[3.3]heptanylpyrimidinyl, 2-oxa-6-azaspiro[3.4]octanylpyrimidinyl, 2-oxa-6-azaspiro[3.5]nonanylpyrimidinyl, 2-oxa-7-azaspiro[3.5]nonanylpyrimidinyl and (dioxo)(methyl)-2,4,8-triazaspiro[4.5]decanylpyrimidinyl.

Suitable values of $R^1$ include bromo, iodo, methylsulphonylphenyl, hydroxyisopropylpyridinyl, hydroxyisopropylpyrimidinyl, carboxycyclohexylpyrimidinyl, carboxybicyclo[3.1.0]hexanylpyrimidinyl, piperazinylpyridinyl, (carboxy)-(methyl)piperidinylpyrimidinyl, (ethoxycarbonyl)(methyl)piperidinylpyrimidinyl, piperazinylpyrimidinyl, oxopiperazinylpyrimidinyl, morpholinylpyrimidinyl, oxodiazepanylpyrimidinyl, carboxy-3-azabicyclo[3.2.1]octanylpyrimidinyl and methoxycarbonyl-3-azabicyclo[3.2.1]octanylpyrimidinyl.

Illustrative values of $R^1$ include bromo, iodo, methylsulphonylphenyl, hydroxyisopropylpyridinyl, hydroxyisopropylpyrimidinyl, carboxybicyclo[3.1.0]hexanylpyrimidinyl, piperazinylpyridinyl, (carboxy)(methyl)piperidinylpyrimidinyl, (ethoxycarbonyl)(methyl)piperidinylpyrimidinyl, piperazinylpyrimidinyl, morpholinylpyrimidinyl, oxodiazepanylpyrimidinyl, carboxy-3-azabicyclo[3.2.1]octanylpyrimidinyl and methoxycarbonyl-3-azabicyclo[3.2.1]octanylpyrimidinyl.

Typically, $R^2$ represents hydrogen, halogen, trifluoromethyl or —$OR^a$; or $R^2$ represents optionally substituted $C_{1-6}$ alkyl.

Suitably, $R^2$ represents hydrogen or halogen.

Typical examples of optional substituents on $R^2$ include $C_{2-6}$ alkoxycarbonyl.

Typical examples of particular substituents on $R^2$ include ethoxycarbonyl.

In a first embodiment, $R^2$ represents hydrogen. In a second embodiment, $R^2$ represents halogen. In one aspect of that embodiment, $R^2$ represents fluoro. In another aspect of that embodiment, $R^2$ represents chloro. In a third embodiment, $R^2$ represents trifluoromethyl. In a fourth embodiment, $R^2$ represents —$OR^a$. In a fifth embodiment, $R^2$ represents optionally substituted $C_{1-6}$ alkyl. In one aspect of that embodiment, $R^2$ represents unsubstituted methyl. In another aspect of that embodiment, $R^2$ represents unsubstituted ethyl. In a further aspect of that embodiment, $R^2$ represents monosubstituted methyl or monosubstituted ethyl.

Typical values of $R^2$ include hydrogen, fluoro, chloro, trifluoromethyl, —$OR^a$, methyl and ethoxycarbonylethyl.

Suitable values of $R^2$ include hydrogen and fluoro.

Typically, $R^3$ represents hydrogen, halogen or $C_{1-6}$ alkyl.

In a first embodiment, $R^3$ represents hydrogen. In a second embodiment, $R^3$ represents halogen. In one aspect of that embodiment, $R^3$ represents fluoro. In a third embodiment, $R^3$ represents $C_{1-6}$ alkyl. In one aspect of that embodiment, $R^3$ represents methyl. In another aspect of that embodiment, $R^3$ represents ethyl.

In a particular embodiment, $R^4$ represents hydrogen.

Suitably, $R^5$ represents hydrogen or $C_{1-6}$ alkyl.

In a first embodiment, $R^5$ represents hydrogen. In a second embodiment, $R^5$ represents $C_{1-6}$ alkyl, especially methyl. In a third embodiment, $R^5$ represents —$SO_2R^a$. In a fourth embodiment, $R^5$ represents —$COR^d$. In a fifth embodiment, $R^5$ represents —$CONR^bR^c$. In a sixth embodiment, $R^5$ represents —$SO_2NR^bR^c$. In a seventh embodiment, $R^5$ represents —$SO(NR^b)R^d$.

Typical values of $R^5$ include hydrogen and methyl.

Suitably, $R^6$ represents hydrogen, methyl or ethyl.

In a first embodiment, $R^6$ represents hydrogen. In a second embodiment, $R^6$ represents $C_{1-6}$ alkyl, especially methyl or ethyl. In one aspect of that embodiment, $R^6$ represents methyl. In another aspect of that embodiment, $R^6$ represents ethyl.

Suitably, $R^{7a}$ represents hydrogen, methyl, ethyl or trifluoromethyl.

In a first embodiment, $R^{7a}$ represents hydrogen. In a second embodiment, $R^{7a}$ represents $C_{1-6}$ alkyl, especially methyl or ethyl. In one aspect of that embodiment, $R^{7a}$ represents methyl. In another aspect of that embodiment, $R^{7a}$ represents ethyl. In a third embodiment, $R^{7a}$ represents trifluoromethyl.

Suitably, $R^{7b}$ represents hydrogen or methyl.

In a first embodiment, $R^{7b}$ represents hydrogen. In a second embodiment, $R^{7b}$ represents $C_{1-6}$ alkyl. In one aspect of that embodiment, $R^{7b}$ represents methyl.

Alternatively, $R^{7a}$ and $R^{7b}$ may together represent oxo. Thus, $R^{7a}$ and $R^{7b}$, when taken together with the carbon atom to which they are both attached, may represent carbonyl (C=O).

Alternatively, $R^{7a}$ and $R^{7b}$ may together form an optionally substituted spiro linkage. Thus, $R^{7a}$ and $R^{7b}$, when taken together with the carbon atom to which they are both attached, may represent $C_{3-7}$ cycloalkyl or $C_{3-7}$ heterocycloalkyl, either of which groups may be unsubstituted, or substituted by one or more substituents, typically by one or two substituents. In one embodiment, $R^{7a}$ and $R^{7b}$, when taken together with the carbon atom to which they are both attached, may suitably represent an optionally substituted cyclopropyl ring. In another embodiment, $R^{7a}$ and $R^{7b}$, when taken together with the carbon atom to which they are both attached, may suitably represent an optionally substituted oxetanyl or azetidinyl ring.

Typical examples of optional substituents on the spirocycle formed by $R^{7a}$ and $R^{7b}$ include $C_{1-6}$ alkyl, halogen, cyano, trifluoromethyl, hydroxy, $C_{1-6}$ alkoxy, $C_{1-6}$ alkylthio, $C_{1-6}$ alkylsulphinyl, $C_{1-6}$ alkylsulphonyl, $C_{2-6}$ alkylcarbonyl, amino, $C_{1-6}$ alkylamino and di($C_{1-6}$)alkylamino.

Typical examples of particular substituents on the spirocycle formed by $R^{7a}$ and $R^{7b}$ include methyl, fluoro, chloro, bromo, cyano, trifluoromethyl, hydroxy, methoxy, methylthio, methylsulphinyl, methylsulphonyl, acetyl, amino, methylamino and dimethylamino.

Typical examples of suitable substituents on $R^a$, $R^b$, $R^c$, $R^d$ or $R^e$, or on the heterocyclic moiety —$NR^bR^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$)alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di($C_{1-6}$)alkylamino, phenylamino, pyridinylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino, aminocarbonyl, $C_{1-6}$ alkylaminocarbonyl and di($C_{1-6}$)alkylaminocarbonyl.

Typical examples of specific substituents on $R^a$, $R^b$, $R^c$, $R^d$ or $R^e$, or on the heterocyclic moiety —$NR^bR^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, tert-butoxycarbonylamino, acetylaminomethyl, methylsulphonylamino, aminocarbonyl, methylaminocarbonyl and dimethylaminocarbonyl.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

Selected values of $R^a$ include methyl, ethyl, benzyl and isoindolylpropyl, any of which groups may be optionally substituted by one or more substituents.

Selected examples of suitable substituents on $R^a$ include $C_{1-6}$ alkoxy and oxo.

Selected examples of specific substituents on $R^a$ include methoxy and oxo.

In one embodiment, $R^a$ represents optionally substituted $C_{1-6}$ alkyl. In one aspect of that embodiment, $R^a$ ideally represents unsubstituted $C_{1-6}$ alkyl, especially methyl. In another aspect of that embodiment, $R^a$ ideally represents substituted $C_{1-6}$ alkyl, e.g. methoxyethyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl. In another embodiment, $R^a$ represents optionally substituted aryl($C_{1-6}$)alkyl, ideally unsubstituted aryl($C_{1-6}$)alkyl, especially benzyl. In a further embodiment, $R^a$ represents optionally substituted heteroaryl. In a further embodiment, $R^a$ represents optionally substituted heteroaryl($C_{1-6}$)alkyl, e.g. dioxoisoindolylpropyl.

Specific values of $R^a$ include methyl, methoxyethyl, benzyl and dioxoisoindolylpropyl.

In a particular aspect, $R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents.

Selected values of $R^b$ include hydrogen; or $C_{1-6}$ alkyl, aryl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Representative values of $R^b$ include hydrogen; or methyl, ethyl, n-propyl, benzyl, pyrrolidinyl or morpholinylpropyl, any of which groups may be optionally substituted by one or more substituents.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-($C_{1-6}$) alkylamino and $C_{2-6}$ alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

Specific values of $R^b$ include hydrogen, methyl, methoxyethyl, methylthioethyl, methylsulphinylethyl, methylsulphonylethyl, hydroxyethyl, cyanoethyl, dimethylaminoethyl, tert-butoxycarbonylaminoethyl, dihydroxypropyl, benzyl, pyrrolidinyl, tert-butoxycarbonylpyrrolidinyl and morpholinylpropyl.

In one embodiment, $R^b$ represents hydrogen. In another embodiment, $R^b$ represents $C_{1-6}$ alkyl, especially methyl.

Selected values of $R^c$ include hydrogen; or $C_{1-6}$ alkyl, $C_{3-7}$ cycloalkyl or $C_{3-7}$ heterocycloalkyl, any of which groups may be optionally substituted by one or more substituents.

In a particular aspect, $R^c$ represents hydrogen, $C_{1-6}$ alkyl or $C_{3-7}$ cycloalkyl.

Representative values of $R^c$ include hydrogen; or methyl, cyclobutyl, cyclopentyl, cyclohexyl, tetrahydropyranyl and piperidinyl, any of which groups may be optionally substituted by one or more substituents.

Selected examples of suitable substituents on $R^c$ include $C_{2-6}$ alkylcarbonyl and $C_{2-6}$ alkoxycarbonyl.

Selected examples of specific substituents on $R^c$ include acetyl and tert-butoxycarbonyl.

Specific values of $R^c$ include hydrogen, methyl, cyclobutyl, cyclopentyl, cyclohexyl, tetrahydropyranyl, acetylpiperidinyl and tert-butoxycarbonylpiperidinyl, Suitably, $R^c$ represents hydrogen or $C_{1-6}$ alkyl. In one embodiment, $R^c$ is hydrogen. In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents.

Selected examples of suitable substituents on the heterocyclic moiety —$NR^bR^c$ include $C_{1-6}$ alkyl, $C_{1-6}$ alkylsulphonyl, hydroxy, hydroxy($C_{1-6}$)alkyl, amino($C_{1-6}$)alkyl, cyano, oxo, $C_{2-6}$ alkylcarbonyl, carboxy, $C_{2-6}$ alkoxycarbonyl, amino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino and aminocarbonyl.

Selected examples of specific substituents on the heterocyclic moiety —$NR^bR^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxycarbonylamino, methylsulphonylamino and aminocarbonyl.

Specific values of the moiety —$NR^bR^c$ include azetidin-1-yl, hydroxyazetidin-1-yl, hydroxymethylazetidin-1-yl, (hydroxy)(hydroxymethyl)azetidin-1-yl, aminomethylazetidin-1-yl, cyanoazetidin-1-yl, carboxyazetidin-1-yl, aminoazetidin-1-yl, aminocarbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxooxazolidin-3-yl, hydroxyisoxazolidin-2-yl, thiazolidin-3-yl, oxothiazolidin-3-yl, dioxoisothiazolidin-2-yl, piperidin-1-yl, hydroxypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl and oxohomopiperazin-1-yl.

Suitably, $R^d$ represents hydrogen; or $C_{1-6}$ alkyl, aryl or heteroaryl, any of which groups may be optionally substituted by one or more substituents.

Selected examples of suitable values for $R^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$ alkylcarbonyloxy and di($C_{1-6}$)alkylamino.

Selected examples of particular substituents on $R^d$ include fluoro, methyl, methoxy, oxo, acetoxy and dimethylamino.

In one embodiment, $R^d$ represents hydrogen. In another embodiment, $R^d$ represents optionally substituted $C_{1-6}$ alkyl. In one aspect of that embodiment, $R^d$ ideally represents unsubstituted $C_{1-6}$ alkyl, e.g. methyl, ethyl, isopropyl, 2-methylpropyl or tert-butyl, especially methyl. In another aspect of that embodiment, $R^d$ ideally represents substituted $C_{1-6}$ alkyl, e.g. substituted methyl or substituted ethyl, including acetoxymethyl, dimethylaminomethyl and trifluoroethyl. In another embodiment, $R^d$ represents optionally substituted aryl. In one aspect of that embodiment, $R^d$ represents unsubstituted aryl, especially phenyl. In another aspect of that embodiment, $R^d$ represents monosubstituted aryl, especially methylphenyl. In a further aspect of that embodiment, $R^d$ represents disubstituted aryl, e.g. dimethoxyphenyl. In a further embodiment, $R^d$ represents optionally substituted heteroaryl, e.g. thienyl, chlorothienyl, methylthienyl, methylimidazolyl or thiazolyl. In another embodiment, $R^d$ represents optionally substituted $C_{3-7}$ cycloalkyl, e.g. cyclopropyl or cyclobutyl. In a further embodiment, $R^d$ represents optionally substituted $C_{3-7}$ heterocycloalkyl, e.g. thiazolidinyl or oxothiazolidinyl.

Selected examples of specific values for $R^d$ include hydrogen, methyl, acetoxymethyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Suitably, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In one embodiment, $R^e$ represents optionally substituted $C_{1-6}$ alkyl, ideally unsubstituted $C_{1-6}$ alkyl, e.g. methyl or propyl, especially methyl. In another embodiment, $R^e$ represents optionally substituted aryl. In one aspect of that embodiment, $R^e$ represents unsubstituted aryl, especially phenyl. In another aspect of that embodiment, $R^e$ represents monosubstituted aryl, especially methylphenyl. In a further embodiment, $R^e$ represents optionally substituted heteroaryl.

Selected values of $R^e$ include methyl, propyl and methylphenyl.

Illustrative sub-classes of compounds according to the invention are represented by the compounds of formula (IIA-A), (IIA-B) and (IIA-C) and N-oxides thereof, and pharmaceutically acceptable salts and solvates thereof, and glucuronide derivatives thereof, and co-crystals thereof:

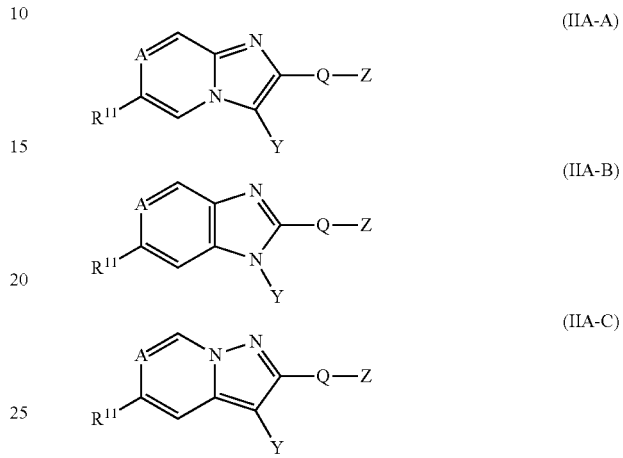

wherein
$R^{11}$ represents halogen or cyano; or $R^{11}$ represents $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl-$(C_{1-6})$alkyl-aryl-, heteroaryl$(C_{3-7})$heterocycloalkyl-, $(C_{3-7})$cycloalkyl-heteroaryl-, $(C_{3-7})$cycloalkyl$(C_{1-6})$alkyl-heteroaryl-, $(C_{4-7})$cycloalkenyl-heteroaryl-, $(C_{4-9})$bicycloalkyl-heteroaryl-, $(C_{3-7})$heterocycloalkyl-heteroaryl-, $(C_{3-7})$heterocycloalkyl$(C_{1-6})$alkyl-heteroaryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents; and A, Y, Q and Z are as defined above.

Examples of optional substituents which may be present on $R^{11}$ include one, two or three substituents independently selected from halogen, halo($C_{1-6}$)alkyl, cyano, cyano($C_{1-6}$)alkyl, nitro, nitro($C_{1-6}$)alkyl, $C_{1-6}$ alkyl, difluoromethyl, trifluoromethyl, difluoroethyl, trifluoroethyl, $C_{2-6}$ alkenyl, hydroxy, hydroxy($C_{1-6}$)alkyl, $C_{1-6}$ alkoxy, difluoromethoxy, trifluoromethoxy, trifluoroethoxy, carboxy($C_{3-7}$)cycloalkyloxy, $C_{1-3}$ alkylenedioxy, $C_{1-6}$ alkoxy($C_{1-6}$)alkyl, $C_{1-6}$ alkylthio, $C_{1-6}$ alkylsulphinyl, $C_{1-6}$ alkylsulphonyl, $(C_{1-6})$alkylsulphonyl($C_{1-6}$)alkyl, oxo, amino, amino($C_{1-6}$)alkyl, $C_{1-6}$ alkylamino, di($C_{1-6}$)alkylamino, hydroxy($C_{1-6}$)alkylamino, $C_{1-6}$ alkoxyamino, $(C_{1-6})$alkoxy($C_{1-6}$)alkylamino, [($C_{1-6}$)alkoxy](hydroxy)($C_{1-6}$)alkylamino, [($C_{1-6}$)alkylthio](hydroxy)($C_{1-6}$)alkylamino, N—[($C_{1-6}$)alkyl]-N-[hydroxy($C_{1-6}$)alkyl]amino, di($C_{1-6}$)alkylamino($C_{1-6}$)alkylamino, N-[di($C_{1-6}$)alkylamino($C_{1-6}$)alkyl]-N-[hydroxy($C_{1-6}$)alkyl]amino, hydroxy($C_{1-6}$)alkyl-($C_{3-7}$)cycloalkylamino, (hydroxy) [($C_{3-7}$)cycloalkyl($C_{1-6}$)alkyl]amino, $(C_{3-7})$heterocycloalkyl($C_{1-6}$)alkylamino, oxo($C_{3-7}$)heterocycloalkyl($C_{1-6}$)alkylamino, $(C_{1-6})$alkylheteroarylamino, heteroaryl($C_{1-6}$)alkylamino, $(C_{1-6})$alkylheteroaryl($C_{1-6}$)alkylamino, $C_{2-6}$ alkylcarbonylamino, N—[($C_{1-6}$)alkyl]-N—[($C_{2-6}$)alkylcarbonyl]amino, $(C_{2-6})$alkylcarbonylamino($C_{1-6}$)alkyl, $C_{3-6}$ alkenylcarbonylamino, bis[($C_{3-6}$)alkenylcarbonyl]amino, N—[($C_{1-6}$)alkyl]-N—[($C_{3-7}$)cycloalkylcarbonyl]amino, $C_{2-6}$ alkoxycarbonylamino, $C_{2-6}$ alkoxycarbonyl($C_{1-6}$)alkylamino, $C_{1-6}$ alkylaminocarbonylamino, $C_{1-6}$ alkylsulphonylamino, N—[($C_{1-6}$)alkyl]-N—[($C_{1-6}$)alkylsulphonyl]amino, bis[($C_{1-6}$)alkylsulphonyl]amino, N—[($C_{1-6}$)alkyl]-N-[carboxy($C_{1-6}$)alkyl]amino, carboxy($C_{3-7}$)cycloalkylamino, carboxy-($C_{3-7}$)cycloalkyl($C_{1-6}$)alkylamino, formyl, $C_{2-6}$ alkylcarbonyl, ($C_{3-7}$)cycloalkylcarbonyl, phenylcarbonyl, ($C_{2-6}$)alkylcarbonyloxy($C_{1-6}$)alkyl, carboxy, carboxy($C_{1-6}$)alkyl, $C_{2-6}$ alkoxycarbonyl, $C_{2-6}$ alkoxycarbonyl($C_{1-6}$)alkyl, morpholinyl($C_{1-6}$)alkoxycarbonyl, $C_{2-6}$ alkoxycarbonylmethylidenyl, a carboxylic acid isostere or prodrug moiety Ω as defined herein, —($C_{1-6}$)alkyl-Ω, aminocarbonyl, $C_{1-6}$ alkylaminocarbonyl, hydroxy($C_{1-6}$)alkylaminocarbonyl, di($C_{1-6}$)alkylaminocarbonyl, aminocarbonyl($C_{1-6}$)alkyl, aminosulphonyl, di($C_{1-6}$)alkylaminosulphonyl, ($C_{1-6}$)alkylsulphoximinyl and [($C_{1-6}$)alkyl][N—($C_{1-6}$)alkyl]-sulphoximinyl.

Examples of particular substituents on $R^{11}$ include fluoro, chloro, bromo, fluoromethyl, fluoroisopropyl, cyano, cyanoethyl, nitro, nitromethyl, methyl, ethyl, isopropyl, isobutyl, tert-butyl, difluoromethyl, trifluoromethyl, difluoroethyl, trifluoroethyl, ethenyl, hydroxy, hydroxymethyl, hydroxyisopropyl, methoxy, isopropoxy, difluoromethoxy, trifluoromethoxy, trifluoroethoxy, carboxycyclobutyloxy, methylenedioxy, ethylenedioxy, methoxymethyl, methoxyethyl, methylthio, methylsulphinyl, methylsulphonyl, methylsulphonylethyl, oxo, amino, aminomethyl, aminoisopropyl, methylamino, ethylamino, dimethylamino, hydroxyethylamino, hydroxypropylamino, (hydroxy)(methyl)propylamino, methoxyamino, methoxyethylamino, (hydroxy)(methoxy)(methyl)propylamino, (hydroxy)(methylthio)butylamino, N-(hydroxyethyl)-N-(methyl)amino, dimethylaminoethylamino, (dimethylamino)(methyl)propylamino, N-(dimethylaminoethyl)-N-(hydroxyethyl)amino, hydroxymethylcyclopentylamino, hydroxycyclobutylmethylamino, (cyclopropyl)(hydroxy)propylamino, morpholinylethylamino, oxopyrrolidinylmethylamino, ethyloxadiazolylamino, methylthiadiazolylamino, thiazolylmethylamino, thiazolylethylamino, pyrimidinylmethylamino, methylpyrazolylmethylamino, acetylamino, N-acetyl-N-methylamino, N-isopropylcarbonyl-N-methylamino, acetylaminomethyl, ethenylcarbonylamino, bis(ethenylcarbonyl)amino, N-cyclopropylcarbonyl-N-methylamino, methoxycarbonylamino, ethoxycarbonylamino, tert-butoxycarbonylamino, methoxycarbonylethylamino, ethylaminocarbonylamino, butylaminocarbonylamino, methylsulphonylamino, N-methyl-N-(methylsulphonyl)amino, bis(methylsulphonyl)amino, N-(carboxymethyl)-N-methylamino, N-(carboxyethyl)-N-methylamino, carboxycyclopentylamino, carboxycyclopropylmethylamino, formyl, acetyl, isopropylcarbonyl, cyclobutylcarbonyl, phenylcarbonyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxycarbonylmethyl, ethoxycarbonylethyl, morpholinylethoxycarbonyl, ethoxycarbonylmethylidenyl, methylsulphonylaminocarbonyl, acetylaminosulphonyl, methoxyaminocarbonyl, tetrazolyl, tetrazolylmethyl, hydroxyoxadiazolyl, aminocarbonyl, methylaminocarbonyl, hydroxyethylaminocarbonyl, dimethylaminocarbonyl, aminocarbonylmethyl, aminosulphonyl, methylaminosulphonyl, dimethylaminosulphonyl, methylsulphoximinyl and (methyl)(N-methyl)sulphoximinyl.

Generally, $R^{11}$ represents $C_{1-6}$ alkyl, $C_{2-6}$ alkynyl, aryl, $C_{3-7}$ heterocycloalkyl, $C_{3-7}$ heterocycloalkenyl, heteroaryl, ($C_{3-7}$)heterocycloalkyl($C_{1-6}$)alkyl-aryl-, heteroaryl-($C_{3-7}$)heterocycloalkyl-, ($C_{3-7}$)cycloalkyl-heteroaryl-, ($C_{3-7}$)cycloalkyl($C_{1-6}$)alkyl-heteroaryl-, ($C_{4-7}$)cycloalkenyl-heteroaryl-, ($C_{4-9}$) bicycloalkyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents.

More generally, $R^{11}$ represents halogen; or $R^{11}$ represents aryl, heteroaryl, ($C_{3-7}$)cycloalkyl-heteroaryl-, ($C_{4-9}$)bicycloalkyl-heteroaryl-, ($C_{3-7}$)heterocycloalkyl-heteroaryl- or ($C_{4-9}$)heterobicycloalkyl-heteroaryl-, any of which groups may be optionally substituted by one or more substituents.

Still more generally, $R^{11}$ represents halogen; or $R^{11}$ represents aryl, heteroaryl, ($C_{4-9}$)bicycloalkyl-heteroaryl-, ($C_{3-7}$)heterocycloalkyl-heteroaryl- or ($C_{4-9}$)heterobicycloalkyl-heteroaryl-, any of which groups may be optionally substituted by one or more substituents.

In a first embodiment, $R^{11}$ represents halogen. In one aspect of that embodiment, $R^{11}$ represents bromo. In another aspect of that embodiment, $R^{11}$ represents iodo.

In a second embodiment, $R^{11}$ represents cyano.

In a third embodiment, $R^{11}$ represents optionally substituted $C_{1-6}$ alkyl. In one aspect of that embodiment, $R^{11}$ represents optionally substituted ethyl.

In a fourth embodiment, $R^{11}$ represents optionally substituted $C_{2-6}$ alkynyl. In one aspect of that embodiment, $R^{11}$ represents optionally substituted butynyl.

In a fifth embodiment, $R^{11}$ represents optionally substituted aryl. In one aspect of that embodiment, $R^{11}$ represents optionally substituted phenyl.

In a sixth embodiment, $R^{11}$ represents optionally substituted $C_{3-7}$ heterocycloalkyl.

In a seventh embodiment, $R^{11}$ represents optionally substituted $C_{3-7}$ heterocycloalkenyl.

In an eighth embodiment, $R^{11}$ represents optionally substituted heteroaryl. In selected aspects of that embodiment, $R^{11}$ represents benzofuryl, thienyl, indolyl, pyrazolyl, indazolyl, isoxazolyl, thiazolyl, imidazolyl, pyridinyl, quinolinyl, pyridazinyl, pyrimidinyl or pyrazinyl, any of which groups may be optionally substituted by one or more substituents.

In a ninth embodiment, $R^{11}$ represents optionally substituted ($C_{3-7}$)-heterocycloalkyl($C_{1-6}$)alkyl-aryl-. In a first aspect of that embodiment, $R^{11}$ represents optionally substituted pyrrolidinylmethylphenyl-. In a second aspect of that embodiment, $R^{11}$ represents optionally substituted piperazinylmethylphenyl-.

In a tenth embodiment, $R^{11}$ represents optionally substituted heteroaryl($C_{3-7}$)-heterocycloalkyl-. In one aspect of that embodiment, $R^{11}$ represents optionally substituted pyridinylpiperazinyl-.

In an eleventh embodiment, $R^{11}$ represents optionally substituted ($C_{3-7}$)cycloalkyl-heteroaryl-. In a first aspect of that embodiment, $R^{11}$ represents optionally substituted cyclohexylpyrazolyl-. In a second aspect of that embodiment, $R^{11}$ represents optionally substituted cyclohexylpyridinyl-. In a third aspect of that embodiment, $R^{11}$ represents optionally substituted cyclopropylpyrimidinyl-. In a fourth aspect of that embodiment, $R^{11}$ represents optionally substituted cyclobutylpyrimidinyl-. In a fifth aspect of that embodiment, $R^{11}$ represents optionally substituted cyclopentylpyrimidinyl-. In a sixth aspect of that embodiment, $R^{11}$ represents optionally substituted cyclohexylpyrimidinyl-. In a seventh aspect of that embodiment, $R^{11}$ represents optionally substituted cyclohexylpyrazinyl-.

In a twelfth embodiment, $R^{11}$ represents optionally substituted $(C_{4-7})$cycloalkenyl-heteroaryl-.

In a thirteenth embodiment, $R^{11}$ represents optionally substituted $(C_{3-7})$-heterocycloalkyl-heteroaryl-. In a first aspect of that embodiment, $R^{11}$ represents optionally substituted pyrrolidinylpyridinyl-. In a second aspect of that embodiment, $R^{11}$ represents optionally substituted tetrahydropyranylpyridinyl-. In a third aspect of that embodiment, $R^{11}$ represents optionally substituted piperidinylpyridinyl-. In a fourth aspect of that embodiment, $R^{11}$ represents optionally substituted piperazinylpyridinyl-. In a fifth aspect of that embodiment, $R^{11}$ represents optionally substituted morpholinylpyridinyl-. In a sixth aspect of that embodiment, $R^{11}$ represents optionally substituted thiomorpholinylpyridinyl-. In a seventh aspect of that embodiment, $R^{11}$ represents optionally substituted diazepanylpyridinyl-. In an eighth aspect of that embodiment, $R^{11}$ represents optionally substituted oxetanylpyrimidinyl-. In a ninth aspect of that embodiment, $R^{11}$ represents optionally substituted azetidinylpyrimidinyl-. In a tenth aspect of that embodiment, $R^{11}$ represents optionally substituted tetrahydrofuranylpyrimidinyl-. In an eleventh aspect of that embodiment, $R^{11}$ represents optionally substituted pyrrolidinylpyrimidinyl-. In a twelfth aspect of that embodiment, $R^{11}$ represents optionally substituted tetrahydropyranylpyrimidinyl-. In a thirteenth aspect of that embodiment, $R^{11}$ represents optionally substituted piperidinylpyrimidinyl-. In a fourteenth aspect of that embodiment, $R^{11}$ represents optionally substituted piperazinylpyrimidinyl-. In a fifteenth aspect of that embodiment, $R^{11}$ represents optionally substituted morpholinylpyrimidinyl-. In a sixteenth aspect of that embodiment, $R^{11}$ represents optionally substituted thiomorpholinylpyrimidinyl-. In a seventeenth aspect of that embodiment, $R^{11}$ represents optionally substituted azepanylpyrimidinyl-. In an eighteenth aspect of that embodiment, $R^{11}$ represents optionally substituted oxazepanylpyrimidinyl-. In a nineteenth aspect of that embodiment, $R^{11}$ represents optionally substituted diazepanylpyrimidinyl-. In a twentieth aspect of that embodiment, $R^{11}$ represents optionally substituted thiadiazepanylpyrimidinyl-. In a twenty-first aspect of that embodiment, $R^{11}$ represents optionally substituted oxetanylpyrazinyl-. In a twenty-second aspect of that embodiment, $R^{11}$ represents optionally substituted piperidinylpyrazinyl-.

In a fourteenth embodiment, $R^{11}$ represents optionally substituted $(C_{3-7})$-heterocycloalkyl$(C_{1-6})$alkyl-heteroaryl-. In a first aspect of that embodiment, $R^{11}$ represents optionally substituted morpholinylmethylthienyl-. In a second aspect of that embodiment, $R^{11}$ represents optionally substituted morpholinylethylpyrazolyl-.

In a fifteenth embodiment, $R^{11}$ represents optionally substituted $(C_{3-7})$-heterocycloalkenyl-heteroaryl-.

In a sixteenth embodiment, $R^{11}$ represents optionally substituted $(C_{4-9})$-heterobicycloalkyl-heteroaryl-.

In a seventeenth embodiment, $R^{11}$ represents optionally substituted $(C_{4-9})$-spiroheterocycloalkyl-heteroaryl-.

In an eighteenth embodiment, $R^{11}$ represents optionally substituted $(C_{3-7})$-cycloalkyl$(C_{1-6})$alkyl-heteroaryl-. In one aspect of that embodiment, $R^{11}$ represents optionally substituted cyclohexylmethylpyrimidinyl-.

In a nineteenth embodiment, $R^{11}$ represents optionally substituted $(C_{4-9})$-bicycloalkyl-heteroaryl-.

Appositely, $R^{11}$ represents bromo or iodo; or $R^{11}$ represents ethyl, butynyl, phenyl, pyrrolidinyl, piperidinyl, piperazinyl, morpholinyl, 1,2,3,6-tetrahydropyridinyl, benzofuryl, thienyl, indolyl, pyrazolyl, indazolyl, isoxazolyl, thiazolyl, imidazolyl, pyridinyl, quinolinyl, pyridazinyl, pyrimidinyl, pyrazinyl, pyrrolidinylmethylphenyl, piperazinylmethylphenyl, pyridinylpiperazinyl, cyclohexylpyrazolyl, cyclohexylpyridinyl, cyclopropylpyrimidinyl, cyclobutylpyrimidinyl, cyclopentylpyrimidinyl, cyclohexylpyrimidinyl, cyclohexylpyrazinyl, cyclohexylmethylpyrimidinyl, cyclohexenylpyridinyl, cyclohexenylpyrimidinyl, bicyclo[3.1.0]hexanylpyridinyl, bicyclo[3.1.0]hexanylpyrimidinyl, bicyclo[4.1.0]heptanylpyrimidinyl, bicyclo[2.2.2]octanylpyrimidinyl, pyrrolidinylpyridinyl, tetrahydropyranylpyridinyl, piperidinylpyridinyl, piperazinylpyridinyl, morpholinylpyridinyl, thiomorpholinylpyridinyl, diazepanylpyridinyl, oxetanylpyrimidinyl, azetidinylpyrimidinyl, tetrahydrofuranylpyrimidinyl, pyrrolidinylpyrimidinyl, tetrahydropyranylpyrimidinyl, piperidinylpyrimidinyl, piperazinylpyrimidinyl, hexahydro-[1,2,5]thiadiazolo[2,3-a]pyrazinylpyrimidinyl, morpholinylpyrimidinyl, thiomorpholinylpyrimidinyl, azepanylpyrimidinyl, oxazepanylpyrimidinyl, diazepanylpyrimidinyl, thiadiazepanylpyrimidinyl, oxetanylpyrazinyl, piperidinylpyrazinyl, morpholinylmethylthienyl, morpholinylethylpyrazolyl, 3-azabicyclo[3.1.0]-hexanylpyridinyl, 3-azabicyclo[3.1.0]hexanylpyridazinyl, 3-azabicyclo[3.1.0]hexanylpyrimidinyl, 2-oxa-5-azabicyclo[2.2.1]heptanylpyrimidinyl, 3-azabicyclo[3.1.1]heptanylpyrimidinyl, 3-azabicyclo[4.1.0]heptanylpyrimidinyl, 3-azabicyclo[4.1.0]heptanylpyrimidinyl, 2-oxabicyclo[2.2.2]octanylpyrimidinyl, 3-azabicyclo[3.2.1]octanylpyrimidinyl, 8-azabicyclo[3.2.1]octanylpyrimidinyl, 3-oxa-8-azabicyclo[3.2.1]octanylpyrimidinyl, 3,6-diazabicyclo[3.2.2]nonanylpyrimidinyl, 3-oxa-7-azabicyclo[3.3.1]-nonanylpyrimidinyl, 5-azaspiro[2.3]hexanylpyrimidinyl, 5-azaspiro[2.4]heptanylpyrimidinyl, 2-azaspiro[3.3]heptanylpyrimidinyl, 2-oxa-6-azaspiro[3.3]heptanylpyrimidinyl, 2-oxa-6-azaspiro[3.4]octanylpyrimidinyl, 2-oxa-6-azaspiro[3.5]nonanylpyrimidinyl, 2-oxa-7-azaspiro[3.5]nonanylpyrimidinyl or 2,4,8-triazaspiro[4.5]decanylpyrimidinyl, any of which groups may be optionally substituted by one or more substituents.

Suitably, $R^{11}$ represents bromo or iodo; or $R^{11}$ represents phenyl, pyridinyl, pyrimidinyl, cyclohexylpyrimidinyl, bicyclo[3.1.0]hexanylpyrimidinyl, piperazinylpyridinyl, piperidinylpyrimidinyl, piperazinylpyrimidinyl, morpholinylpyrimidinyl, diazepanylpyrimidinyl or 3-azabicyclo[3.2.1]octanylpyrimidinyl, any of which groups may be optionally substituted by one or more substituents.

Illustratively, $R^{11}$ represents bromo or iodo; or $R^{11}$ represents phenyl, pyridinyl, pyrimidinyl, bicyclo[3.1.0]hexanylpyrimidinyl, piperazinylpyridinyl, piperidinylpyrimidinyl, piperazinylpyrimidinyl, morpholinylpyrimidinyl, diazepanylpyrimidinyl or 3-azabicyclo[3.2.1]octanylpyrimidinyl, any of which groups may be optionally substituted by one or more substituents.

Typical examples of optional substituents on $R^{11}$ include one, two or three substituents independently selected from halogen, halo$(C_{1-6})$alkyl, cyano, cyano$(C_{1-6})$alkyl, nitro$(C_{1-6})$alkyl, $C_{1-6}$ alkyl, trifluoromethyl, trifluoroethyl, $C_{2-6}$ alkenyl, hydroxy, hydroxy$(C_{1-6})$alkyl, $C_{1-6}$ alkoxy, trifluoroethoxy, carboxy$(C_{3-7})$cycloalkyloxy, $C_{1-6}$ alkylthio, $C_{1-6}$ alkylsulphonyl, $(C_{1-6})$alkylsulphonyl$(C_{1-6})$alkyl, oxo, amino, amino-$(C_{1-6})$alkyl, $C_{1-6}$ alkylamino, di$(C_{1-6})$alkylamino, $(C_{1-6})$alkoxy$(C_{1-6})$alkylamino, N—[$(C_{1-6})$alkyl]-N-[hydroxy$(C_{1-6})$alkyl]amino, $(C_{2-6})$alkylcarbonylamino$(C_{1-6})$alkyl, $C_{1-6}$ alkylsulphonylamino, N—[$(C_{1-6})$alkyl]-N—[$(C_{1-6})$alkylsulphonyl]amino, bis[$(C_{1-6})$alkylsulphonyl]amino, N—[$(C_{1-6})$alkyl]-N-[carboxy$(C_{1-6})$alkyl]amino, carboxy$(C_{3-7})$cycloalkylamino, carboxy$(C_{3-7})$cycloalkyl$(C_{1-6})$ alkylamino, formyl, $C_{2-6}$ alkylcarbonyl, $(C_{2-6})$alkylcarbonyloxy$(C_{1-6})$alkyl, carboxy, carboxy$(C_{1-6})$alkyl, $C_{2-6}$ alkoxycarbonyl, $C_{2-6}$ alkoxycarbonyl$(C_{1-6})$alkyl, morpholinyl$(C_{1-6})$alkoxycarbonyl, $C_{2-6}$ alkoxycarbonylmethylidenyl, a carboxylic acid isostere or prodrug moiety Ω as defined herein, —$(C_{1-6})$alkyl-Ω, aminocarbonyl, aminosulphonyl, $(C_{1-6})$alkylsulphoximinyl and $[(C_{1-6})alkyl][N—(C_{1-6})alkyl]$ sulphoximinyl.

Suitable examples of optional substituents on $R^{11}$ include one, two or three substituents independently selected from $C_{1-6}$ alkyl, hydroxy$(C_{1-6})$alkyl, $C_{1-6}$ alkylsulphonyl, oxo, carboxy and $C_{2-6}$ alkoxycarbonyl.

Typical examples of particular substituents on $R^{11}$ include one, two or three substituents independently selected from fluoro, chloro, fluoromethyl, fluoroisopropyl, cyano, cyanoethyl, nitromethyl, methyl, ethyl, isopropyl, trifluoromethyl, trifluoroethyl, ethenyl, hydroxy, hydroxymethyl, hydroxyisopropyl, methoxy, isopropoxy, trifluoroethoxy, carboxycyclobutyloxy, methylthio, methylsulphonyl, methylsulphonylethyl, oxo, amino, aminomethyl, aminoisopropyl, methylamino, dimethylamino, methoxyethylamino, N-(hydroxyethyl)-N-(methyl)amino, acetylaminomethyl, methylsulphonylamino, N-methyl-N-(methylsulphonyl)amino, bis(methylsulphonyl)amino, N-(carboxyethyl)-N-(methyl)amino, carboxycyclopentylamino, carboxycyclopropylmethylamino, formyl, acetyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxycarbonylmethyl, ethoxycarbonylethyl, morpholinylethoxycarbonyl, ethoxycarbonylmethylidenyl, methylsulphonylaminocarbonyl, acetylaminosulphonyl, methoxyaminocarbonyl, tetrazolyl, tetrazolylmethyl, hydroxyoxadiazolyl, aminocarbonyl, aminosulphonyl, methylsulphoximinyl and (methyl)(N-methyl)sulphoximinyl.

Suitable examples of particular substituents on $R^{11}$ include one, two or three substituents independently selected from methyl, hydroxyisopropyl, methylsulphonyl, oxo, carboxy, methoxycarbonyl and ethoxycarbonyl.

In a particular embodiment, $R^{11}$ is substituted by hydroxy $(C_{1-6})$alkyl. In one aspect of that embodiment, $R^{11}$ is substituted by hydroxyisopropyl, especially 2-hydroxyprop-2-yl.

Selected values of $R^{11}$ include bromo, iodo, methoxycarbonylethyl, ethoxycarbonylethyl, hydroxybutynyl, chlorophenyl, hydroxyphenyl, methylsulphonylphenyl, aminomethylphenyl, aminoisopropylphenyl, acetylaminomethylphenyl, acetylphenyl, methoxycarbonylphenyl, aminocarbonylphenyl, aminosulphonylphenyl, acetylaminosulphonylphenyl, (methoxycarbonyl)(methyl) pyrrolidinyl, oxopiperidinyl, ethoxycarbonylpiperidinyl, methylsulphonylpiperazinyl, morpholinyl, methylsulphonyl-1,2,3,6-tetrahydropyridinyl, acetyl-1,2,3,6-tetrahydropyridinyl, tert-butoxycarbonyl-1,2,3,6-tetrahydropyridinyl, methoxycarbonylmethyl-1,2,3,6-tetrahydropyridinyl, benzofuryl, thienyl, indolyl, pyrazolyl, methylpyrazolyl, dimethylpyrazolyl, (methyl)[N-methyl-N-(methylsulfonyl)amino]pyrazolyl, methylindazolyl, dimethylisoxazolyl, hydroxyisopropylthiazolyl, methylimidazolyl, dimethylimidazolyl, pyridinyl, fluoropyridinyl, cyanopyridinyl, methylpyridinyl, (cyano)(methyl)pyridinyl, dimethylpyridinyl, trifluoromethylpyridinyl, ethenylpyridinyl, hydroxyisopropylpyridinyl, methoxypyridinyl, (methoxy)(methyl)pyridinyl, isopropoxypyridinyl, trifluoromethoxypyridinyl, (methyl)-(trifluoroethoxy)pyridinyl, methylsulphonylpyridinyl, oxopyridinyl, (methyl)(oxo)-pyridinyl, (dimethyl)(oxo)pyridinyl, aminopyridinyl, methylaminopyridinyl, dimethylaminopyridinyl, methoxyethylaminopyridinyl, N-(hydroxyethyl)-N-(methyl)aminopyridinyl, methylsulphonylaminopyridinyl, [bis(methylsulphonyl)amino]pyridinyl, carboxypyridinyl, quinolinyl, hydroxypyridazinyl, pyrimidinyl, fluoroisopropylpyrimidinyl, hydroxyisopropylpyrimidinyl, methoxypyrimidinyl, carboxycyclobutyloxypyrimidinyl, methylthiopyrimidinyl, methylsulphonylpyrimidinyl, oxopyrimidinyl, aminopyrimidinyl, dimethylaminopyrimidinyl, methoxyethylaminopyrimidinyl, N-(carboxyethyl)-N-(methyl)aminopyrimidinyl, carboxycyclopentylaminopyrimidinyl, carboxycyclopropylmethylaminopyrimidinyl, acetoxyisopropylpyrimidinyl, ethoxycarbonylethylpyrimidinyl, hydroxypyrazinyl, hydroxyisopropylpyrazinyl, pyrrolidinylmethylphenyl, piperazinylmethylphenyl, pyridinylpiperazinyl, carboxycyclohexylpyrazolyl, carboxycyclohexylpyridinyl, fluoromethylcyclopropylpyrimidinyl, acetylaminomethylcyclopropylpyrimidinyl, hydroxycyclobutylpyrimidinyl, carboxycyclopentylpyrimidinyl, carboxycyclohexylpyrimidinyl, (carboxy)(methyl)cyclohexylpyrimidinyl, (carboxy)(hydroxy)cyclohexylpyrimidinyl, carboxymethylcyclohexylpyrimidinyl, ethoxycarbonylcyclohexylpyrimidinyl, (methoxycarbonyl)(methyl)-cyclohexylpyrimidinyl, (ethoxycarbonyl)(methyl)cyclohexylpyrimidinyl, carboxycyclohexylpyrazinyl, carboxycyclohexylmethylpyrimidinyl, carboxycyclohexenylpyridinyl, carboxycyclohexenylpyrimidinyl, ethoxycarbonylcyclohexenylpyrimidinyl, carboxybicyclo[3.1.0]hexanylpyridinyl, carboxybicyclo[3.1.0]hexanylpyrimidinyl, ethoxycarbonylbicyclo[3.1.0]hexanylpyrimidinyl, carboxybicyclo[4.1.0]heptanylpyrimidinyl, carboxybicyclo[2.2.2]octanylpyrimidinyl, pyrrolidinylpyridinyl, hydroxypyrrolidinylpyridinyl, hydroxytetrahydropyranylpyridinyl, piperidinylpyridinyl, acetylpiperidinylpyridinyl, (carboxy)(methyl)piperidinylpyridinyl, [(carboxy)(methyl)-piperidinyl](fluoro)pyridinyl, [(carboxy)(methyl)piperidinyl](chloro)pyridinyl, piperazinylpyridinyl, (methyl)(piperazinyl)pyridinyl, cyanoethylpiperazinylpyridinyl, trifluoroethylpiperazinylpyridinyl, methylsulphonylpiperazinylpyridinyl, methylsulphonylethylpiperazinylpyridinyl, oxopiperazinylpyridinyl, acetylpiperazinylpyridinyl, (tert-butoxycarbonylpiperazinyl)(methyl)pyridinyl, carboxymethylpiperazinylpyridinyl, carboxyethylpiperazinylpyridinyl, ethoxycarbonylmethylpiperazinylpyridinyl, ethoxycarbonylethylpiperazinylpyridinyl, morpholinylpyridinyl, thiomorpholinylpyridinyl, oxothiomorpholinylpyridinyl, dioxothiomorpholinylpyridinyl, oxodiazepanylpyridinyl, fluorooxetanylpyrimidinyl, hydroxyoxetanylpyrimidinyl, hydroxyazetidinylpyrimidinyl, (hydroxy)(methyl)azetidinylpyrimidinyl, carboxyazetidinylpyrimidinyl, (tert-butoxycarbonyl)(hydroxy)azetidinylpyrimidinyl, tetrazolylazetidinylpyrimidinyl, hydroxytetrahydrofuranylpyrimidinyl, hydroxypyrrolidinylpyrimidinyl, carboxypyrrolidinylpyrimidinyl, (carboxy)(methyl)pyrrolidinylpyrimidinyl, carboxymethylpyrrolidinylpyrimidinyl, ethoxycarbonylpyrrolidinylpyrimidinyl, fluorotetrahydropyranylpyrimidinyl, hydroxytetrahydropyranylpyrimidinyl, difluoropiperidinylpyrimidinyl, (cyano)(methyl)piperidinylpyrimidinyl, (hydroxy)(nitromethyl)piperidinylpyrimidinyl, (hydroxy)(methyl)piperidinylpyrimidinyl, (hydroxy)(trifluoromethyl)-piperidinylpyrimidinyl, (hydroxymethyl)(methyl) piperidinylpyrimidinyl, methylsulphonylpiperidinylpyrimidinyl, oxopiperidinylpyrimidinyl, (formyl)(methyl)-piperidinylpyrimidinyl, carboxypiperidinylpyrimidinyl, (carboxy)(fluoro)piperidinylpyrimidinyl, (carboxy)(methyl)piperidinylpyrimidinyl, (carboxy)(ethyl)piperidinylpyrimidinyl, (carboxy)(trifluoromethyl)piperidinylpyrimidinyl, (carboxy)(hydroxy)-piperidinylpyrimidinyl, (carboxy)(hydroxymethyl)piperidinylpyrimidinyl, (carboxy)-(methoxy)piperidinylpyrimidinyl, (amino)(carboxy)piperidinylpyrimidinyl, carboxymethylpiperidinylpyrimidinyl, methoxycarbonylpiperidinylpyrimidinyl, ethoxycarbonylpiperidinylpyrimidinyl, (ethoxycarbonyl)(fluoro)piperidinylpyrimidinyl, (methoxycarbonyl)(methyl)piperidinylpyrimidinyl, (ethyl)(methoxycarbonyl)piperidinylpyrimidinyl, (isopropyl)(methoxycarbonyl)piperidinylpyrimidinyl, (ethoxycarbonyl)-(methyl)piperidinylpyrimidinyl, (n-butoxycarbonyl)(methyl)piperidinylpyrimidinyl, (ethoxycarbonyl)(trifluoromethyl)piperidinylpyrimidinyl, (ethoxycarbonyl)-(hydroxymethyl)piperidinylpyrimidinyl, (methoxy)(methoxycarbonyl)piperidinylpyrimidinyl, (carboxy)(methoxycarbonyl)piperidinylpyrimidinyl, (methyl)-(morpholinylethoxycarbonyl)piperidinylpyrimidinyl, ethoxycarbonylmethylpiperidinylpyrimidinyl, methylsulphonylaminocarbonylpiperidinylpyrimidinyl, acetylaminosulphonylpiperidinylpyrimidinyl, methoxyaminocarbonylpiperidinylpyrimidinyl, tetrazolylpiperidinylpyrimidinyl, hydroxyoxadiazolylpiperidinylpyrimidinyl, aminosulphonylpiperidinylpyrimidinyl, piperazinylpyrimidinyl, methylsulphonylpiperazinylpyrimidinyl, oxopiperazinylpyrimidinyl, carboxypiperazinylpyrimidinyl, carboxyethylpiperazinylpyrimidinyl, tert-butoxycarbonylpiperazinylpyrimidinyl, tetrazolylmethylpiperazinylpyrimidinyl, trioxohexahydro-[1,2,5]thiadiazolo[2,3-a]pyrazinylpyrimidinyl, morpholinylpyrimidinyl, dimethylmorpholinylpyrimidinyl, hydroxymethylmorpholinylpyrimidinyl, carboxymorpholinylpyrimidinyl, (carboxy)(methyl)morpholinylpyrimidinyl, carboxymethylmorpholinylpyrimidinyl, thiomorpholinylpyrimidinyl, dioxothiomorpholinylpyrimidinyl, carboxyazepanylpyrimidinyl, carboxyoxazepanylpyrimidinyl, oxodiazepanylpyrimidinyl, (oxodiazepanyl)(trifluoromethyl)pyrimidinyl, (oxodiazepanyl)(methoxy)pyrimidinyl, (methyl)(oxo)diazepanylpyrimidinyl, dioxothiadiazepanylpyrimidinyl, hydroxyoxetanylpyrazinyl, (carboxy)(methyl)piperidinylpyrazinyl, (ethoxycarbonyl)(methyl)piperidinylpyrazinyl, morpholinylmethylthienyl, morpholinylethylpyrazolyl, carboxy-3-azabicyclo[3.1.0]hexanylpyridinyl, carboxy-3-azabicyclo[3.1.0]hexanylpyridazinyl, carboxy-3-azabicyclo[3.1.0]hexanylpyrimidinyl, (carboxy)(methyl)-3-azabicyclo[3.1.0]hexanylpyrimidinyl, methoxycarbonyl-3-azabicyclo[3.1.0]hexanylpyrimidinyl, ethoxycarbonyl-3-azabicyclo[3.1.0]hexanylpyrimidinyl, 2-oxa-5-azabicyclo[2.2.1]heptanylpyrimidinyl, carboxy-2-oxa-5-azabicyclo-[2.2.1]heptanylpyrimidinyl, carboxy-3-azabicyclo[3.1.1]heptanylpyrimidinyl, carboxy-3-azabicyclo[4.1.0]heptanylpyridinyl, carboxy-3-azabicyclo[4.1.0]heptanylpyrimidinyl, methoxycarbonyl-3-azabicyclo[4.1.0]heptanylpyrimidinyl, ethoxycarbonyl-3-azabicyclo-[4.1.0]heptanylpyrimidinyl, (hydroxy)(methyl)(oxo)-2-oxabicyclo[2.2.2]octanylpyrimidinyl, carboxy-3-azabicyclo[3.2.1]octanylpyrimidinyl, methoxycarbonyl-3-azabicyclo[3.2.1]octanylpyrimidinyl, oxo-8-azabicyclo[3.2.1]octanylpyrimidinyl, ethoxycarbonylmethylidenyl-8-azabicyclo[3.2.1]octanylpyrimidinyl, 3-oxa-8-azabicyclo-[3.2.1]octanylpyrimidinyl, oxo-3,6-diazabicyclo[3.2.2]nonanylpyrimidinyl, carboxy-3-oxa-7-azabicyclo[3.3.1]nonanylpyrimidinyl, carboxy-5-azaspiro[2.3]hexanylpyrimidinyl, (carboxy)(methyl)-5-azaspiro[2.3]hexanylpyrimidinyl, carboxy-5-azaspiro[2.4]heptanylpyrimidinyl, carboxy-2-azaspiro[3.3]heptanylpyrimidinyl, 2-oxa-6-azaspiro[3.3]heptanylpyrimidinyl, 2-oxa-6-azaspiro[3.4]octanylpyrimidinyl, 2-oxa-6-azaspiro[3.5]nonanylpyrimidinyl, 2-oxa-7-azaspiro[3.5]nonanylpyrimidinyl and (dioxo)(methyl)-2,4,8-triazaspiro[4.5]decanylpyrimidinyl.

Suitable values of $R^{11}$ include bromo, iodo, methylsulphonylphenyl, hydroxyisopropylpyridinyl, hydroxyisopropylpyrimidinyl, carboxycyclohexylpyrimidinyl, carboxybicyclo[3.1.0]hexanylpyrimidinyl, piperazinylpyridinyl, (carboxy)-(methyl)piperidinylpyrimidinyl, (ethoxycarbonyl)(methyl)piperidinylpyrimidinyl, piperazinylpyrimidinyl, oxopiperazinylpyrimidinyl, morpholinylpyrimidinyl, oxodiazepanylpyrimidinyl, carboxy-3-azabicyclo[3.2.1]octanylpyrimidinyl and methoxycarbonyl-3-azabicyclo[3.2.1]octanylpyrimidinyl.

Illustrative values of $R^{11}$ include bromo, iodo, methylsulphonylphenyl, hydroxyisopropylpyridinyl, hydroxyisopropylpyrimidinyl, carboxybicyclo[3.1.0]hexanylpyrimidinyl, piperazinylpyridinyl, (carboxy)(methyl)piperidinylpyrimidinyl, (ethoxycarbonyl)(methyl)piperidinylpyrimidinyl, piperazinylpyrimidinyl, morpholinylpyrimidinyl, oxodiazepanylpyrimidinyl, carboxy-3-azabicyclo[3.2.1]octanylpyrimidinyl and methoxycarbonyl-3-azabicyclo[3.2.1]octanylpyrimidinyl.

A particular sub-group of the compounds of formula (IIA-A) above is represented by the compounds of formula (IIB-A) and N-oxides thereof, and pharmaceutically acceptable salts and solvates thereof, and glucuronide derivatives thereof, and co-crystals thereof:

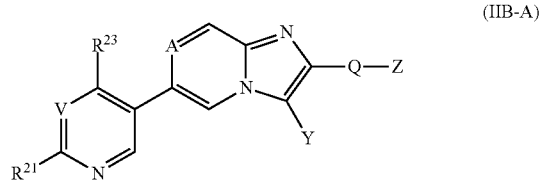

(IIB-A)

wherein

V represents C—$R^{22}$ or N;

$R^{21}$ represents hydrogen, halogen, halo($C_{1-6}$)alkyl, cyano, $C_{1-6}$ alkyl, trifluoromethyl, $C_{2-6}$ alkenyl, $C_{2-6}$ alkynyl, hydroxy, hydroxy($C_{1-6}$)alkyl, $C_{1-6}$ alkoxy, ($C_{1-6}$)alkoxy-($C_{1-6}$)alkyl, difluoromethoxy, trifluoromethoxy, trifluoroethoxy, carboxy($C_{3-7}$)cycloalkyloxy, $C_{1-6}$ alkylthio, $C_{1-6}$ alkylsulphonyl, ($C_{1-6}$)alkylsulphonyl($C_{1-6}$)alkyl, amino, amino-($C_{1-6}$)alkyl, $C_{1-6}$ alkylamino, di($C_{1-6}$)alkylamino, ($C_{1-6}$)alkoxy($C_{1-6}$)alkylamino, N—[($C_{1-6}$)-alkyl]-N-[hydroxy($C_{1-6}$)alkyl]amino, $C_{2-6}$ alkylcarbonylamino, ($C_{2-6}$)alkylcarbonylamino-($C_{1-6}$)alkyl, $C_{2-6}$ alkoxycarbonylamino, N—[($C_{1-6}$)alkyl]-N-[carboxy($C_{1-6}$)alkyl]amino, carboxy($C_{3-7}$)cycloalkylamino, carboxy($C_{3-7}$)cycloalkyl($C_{1-6}$)alkylamino, $C_{1-6}$ alkylsulphonylamino, $C_{1-6}$ alkylsulphonylamino($C_{1-6}$)alkyl, formyl, $C_{2-6}$ alkylcarbonyl, ($C_{2-6}$)alkylcarbonyloxy($C_{1-6}$)alkyl, carboxy, carboxy($C_{1-6}$)alkyl, $C_{2-6}$ alkoxycarbonyl, morpholinyl($C_{1-6}$)alkoxycarbonyl, $C_{2-6}$ alkoxycarbonyl($C_{1-6}$)alkyl, $C_{2-6}$ alkoxycarbonylmethylidenyl, aminocarbonyl, $C_{1-6}$ alkylaminocarbonyl, di($C_{1-6}$)alkylaminocarbonyl, aminosulphonyl, $C_{1-6}$ alkylaminosulphonyl, di($C_{1-6}$)alkylaminosulphonyl, ($C_{1-6}$)alkylsulphoximinyl or [($C_{1-6}$)alkyl][N—($C_{1-6}$)alkyl]sulphoximinyl; or $R^{21}$ represents ($C_{3-7}$)cycloalkyl, ($C_{3-7}$)cycloalkyl($C_{1-6}$)alkyl, ($C_{4-7}$)cycloalkenyl, ($C_{4-9}$)bicycloalkyl, ($C_{3-7}$)heterocycloalkyl, ($C_{3-7}$)heterocycloalkenyl, ($C_{4-9}$)heterobicycloalkyl or ($C_{4-9}$)

spiroheterocycloalkyl, any of which groups may be optionally substituted by one or more substituents;

$R^{22}$ represents hydrogen, halogen or $C_{1-6}$ alkyl;

$R^{23}$ represents hydrogen, $C_{1-6}$ alkyl, trifluoromethyl or $C_{1-6}$ alkoxy; and A, Y, Q and Z are as defined above.

In one embodiment, V represents C—$R^{22}$. In another embodiment, V represents N.

Typically, $R^{21}$ represents hydrogen, halogen, halo($C_{1-6}$) alkyl, cyano, $C_{1-6}$ alkyl, trifluoromethyl, $C_{2-6}$ alkenyl, hydroxy, hydroxy($C_{1-6}$)alkyl, $C_{1-6}$ alkoxy, trifluoroethoxy, carboxy($C_{3-7}$)cycloalkyloxy, $C_{1-6}$ alkylthio, $C_{1-6}$ alkylsulphonyl, amino, $C_{1-6}$ alkylamino, di($C_{1-6}$)alkylamino, ($C_{1-6}$) alkoxy($C_{1-6}$)alkylamino, N—[($C_{1-6}$)alkyl]-N-[hydroxy ($C_{1-6}$)alkyl]-amino, N—[($C_{1-6}$)alkyl]-N-[carboxy($C_{1-6}$) alkyl]amino, carboxy($C_{3-7}$)cycloalkylamino, carboxy($C_{3-7}$) cycloalkyl($C_{1-6}$)alkylamino, $C_{1-6}$ alkylsulphonylamino, ($C_{2-6}$)alkylcarbonyl-oxy($C_{1-6}$)alkyl, carboxy, morpholinyl ($C_{1-6}$)alkoxycarbonyl, $C_{2-6}$ alkoxycarbonyl($C_{1-6}$)alkyl or $C_{2-6}$ alkoxycarbonylmethylidenyl; or $R^{21}$ represents ($C_{3-7}$) cycloalkyl, ($C_{3-7}$)cycloalkyl-($C_{1-6}$)alkyl, ($C_{4-7}$)cycloalkenyl, ($C_{4-9}$)bicycloalkyl, ($C_{3-7}$)heterocycloalkyl, ($C_{4-9}$)heterobicycloalkyl or ($C_{4-9}$)spiroheterocycloalkyl, any of which groups may be optionally substituted by one or more substituents.

Generally, $R^{21}$ represents hydroxy($C_{1-6}$)alkyl; or $R^{21}$ represents ($C_{3-7}$)cycloalkyl, ($C_{4-9}$)bicycloalkyl, ($C_{3-7}$)heterocycloalkyl or ($C_{4-9}$)heterobicycloalkyl, any of which groups may be optionally substituted by one or more substituents.

Suitably, $R^{21}$ represents hydroxy($C_{1-6}$)alkyl; or $R^{21}$ represents ($C_{4-9}$)bicycloalkyl, ($C_{3-7}$)heterocycloalkyl or ($C_{4-9}$) heterobicycloalkyl, any of which groups may be optionally substituted by one or more substituents.

Where $R^{21}$ represents an optionally substituted ($C_{3-7}$) cycloalkyl group, typical values include cyclopropyl, cyclobutyl, cyclopentyl, cyclohexyl and cycloheptyl, any of which groups may be optionally substituted by one or more substituents.

Where $R^{21}$ represents an optionally substituted ($C_{3-7}$) cycloalkyl($C_{1-6}$)alkyl group, a typical value is cyclohexylmethyl, which group may be optionally substituted by one or more substituents.

Where $R^{21}$ represents an optionally substituted ($C_{4-7}$) cycloalkenyl group, typical values include cyclobutenyl, cyclopentenyl, cyclohexenyl and cycloheptenyl, any of which groups may be optionally substituted by one or more substituents.

Where $R^{21}$ represents an optionally substituted ($C_{4-9}$) bicycloalkyl group, typical values include bicyclo[3.1.0] hexanyl, bicyclo[4.1.0]heptanyl and bicyclo[2.2.2]octanyl, any of which groups may be optionally substituted by one or more substituents.

Where $R^{21}$ represents an optionally substituted ($C_{3-7}$) heterocycloalkyl group, typical values include oxetanyl, azetidinyl, tetrahydrofuranyl, pyrrolidinyl, tetrahydropyranyl, piperidinyl, piperazinyl, hexahydro-[1,2,5]thiadiazolo [2,3-a]pyrazinyl, morpholinyl, thiomorpholinyl, azepanyl, oxazepanyl, diazepanyl and thiadiazepanyl, any of which groups may be optionally substituted by one or more substituents.

Where $R^{21}$ represents an optionally substituted ($C_{3-7}$) heterocycloalkenyl group, a typical value is optionally substituted 1,2,3,6-tetrahydropyridinyl.

Where $R^{21}$ represents an optionally substituted ($C_{4-9}$) heterobicycloalkyl, typical values include 3-azabicyclo[3.1.0]hexanyl, 2-oxa-5-azabicyclo[2.2.1]heptanyl, 3-azabicyclo[3.1.1]heptanyl, 3-azabicyclo[4.1.0]heptanyl, 2-oxabicyclo[2.2.2]octanyl, quinuclidinyl, 2-oxa-5-azabicyclo[2.2.2]octanyl, 3-azabicyclo[3.2.1]octanyl, 8-azabicyclo-[3.2.1]octanyl, 3-oxa-8-azabicyclo[3.2.1]octanyl, 3,8-diazabicyclo[3.2.1]octanyl, 3,6-diazabicyclo[3.2.2]nonanyl, 3-oxa-7-azabicyclo[3.3.1]nonanyl and 3,9-diazabicyclo-[4.2.1]nonanyl, any of which groups may be optionally substituted by one or more substituents.

Where $R^{21}$ represents an optionally substituted ($C_{4-9}$) spiroheterocycloalkyl group, typical values include 5-azaspiro[2.3]hexanyl, 5-azaspiro[2.4]heptanyl, 2-azaspiro [3.3]-heptanyl, 2-oxa-6-azaspiro[3.3]heptanyl, 2-oxa-6-azaspiro[3.4]octanyl, 2-oxa-6-azaspiro-[3.5]nonanyl, 2-oxa-7-azaspiro[3.5]nonanyl and 2,4,8-triazaspiro[4.5]-decanyl, any of which groups may be optionally substituted by one or more substituents.

Illustratively, $R^{21}$ represents hydroxy, hydroxy($C_{1-6}$) alkyl, methoxy, carboxycyclobutyloxy, methylthio, methylsulphonyl, methylamino, N-[carboxyethyl]-N-methylamino, carboxycyclopentylamino, carboxycyclopropylmethylamino or ethoxycarbonylethyl; or $R^{21}$ represents cyclopropyl, cyclobutyl, cyclopentyl, cyclohexyl, cyclohexylmethyl, cyclohexenyl, bicyclo[3.1.0]hexanyl, bicyclo[4.1.0]heptanyl, bicyclo[2.2.2]-octanyl, oxetanyl, azetidinyl, tetrahydrofuranyl, pyrrolidinyl, tetrahydropyranyl, piperidinyl, piperazinyl, hexahydro-[1,2,5]thiadiazolo[2,3-a]pyrazinyl, morpholinyl, thiomorpholinyl, azepanyl, oxazepanyl, diazepanyl, thiadiazepanyl, 3-azabicyclo[3.1.0]-hexanyl, 2-oxa-5-azabicyclo[2.2.1]heptanyl, 3-azabicyclo[3.1.1]heptanyl, 3-azabicyclo-[4.1.0]heptanyl, 2-oxabicyclo[2.2.2]octanyl, 3-azabicyclo[3.2.1]octanyl, 8-azabicyclo-[3.2.1]octanyl, 3-oxa-8-azabicyclo[3.2.1]octanyl, 3,6-diazabicyclo[3.2.2] nonanyl, 3-oxa-7-azabicyclo[3.3.1]nonanyl, 5-azaspiro[2.3] hexanyl, 5-azaspiro[2.4]heptanyl or 2-azaspiro-[3.3]heptanyl, any of which groups may be optionally substituted by one or more substituents.

More generally, $R^{21}$ represents hydroxy($C_{1-6}$)alkyl; or $R^{21}$ represents cyclohexyl, bicyclo[3.1.0]hexanyl, piperidinyl, piperazinyl, morpholinyl, diazepanyl or 3-azabicyclo- [3.2.1]octanyl, any of which groups may be optionally substituted by one or more substituents.

Appositely, $R^{21}$ represents hydroxy($C_{1-6}$)alkyl; or $R^{21}$ represents bicyclo[3.1.0]-hexanyl, piperidinyl, piperazinyl, morpholinyl, diazepanyl or 3-azabicyclo[3.2.1]octanyl, any of which groups may be optionally substituted by one or more substituents.

Examples of optional substituents which may be present on $R^{21}$ include one, two or three substituents independently selected from halogen, halo($C_{1-6}$)alkyl, cyano, cyano-($C_{1-6}$) alkyl, nitro, nitro($C_{1-6}$)alkyl, $C_{1-6}$ alkyl, trifluoromethyl, trifluoroethyl, $C_{2-6}$ alkenyl, hydroxy, hydroxy($C_{1-6}$)alkyl, $C_{1-6}$ alkoxy, difluoromethoxy, trifluoromethoxy, trifluoroethoxy, $C_{1-6}$ alkylthio, $C_{1-6}$ alkylsulphonyl, ($C_{1-6}$)alkylsulphonyl($C_{1-6}$)alkyl, oxo, amino, $C_{1-6}$ alkylamino, di($C_{1-6}$) alkylamino, $C_{2-6}$ alkylcarbonylamino, ($C_{2-6}$) alkylcarbonylamino-($C_{1-6}$)alkyl, $C_{2-6}$ alkoxycarbonylamino, $C_{1-6}$ alkylsulphonylamino, formyl, $C_{2-6}$ alkylcarbonyl, carboxy, carboxy($C_{1-6}$)alkyl, $C_{2-6}$ alkoxycarbonyl, morpholinyl-($C_{1-6}$)alkoxycarbonyl, $C_{2-6}$ alkoxycarbonyl($C_{1-6}$)alkyl, $C_{2-6}$ alkoxycarbonylmethylidenyl, a carboxylic acid isostere or prodrug moiety Ω as defined herein, —($C_{1-6}$)alkyl-Ω, aminocarbonyl, $C_{1-6}$ alkylaminocarbonyl, di($C_{1-6}$)alkylaminocarbonyl, aminosulphonyl, di($C_{1-6}$)alkylaminosulphonyl, ($C_{1-6}$)alkylsulphoximinyl and [($C_{1-6}$)alkyl][N—($C_{1-6}$) alkyl]-sulphoximinyl.

Selected examples of optional substituents on $R^{21}$ include one, two or three substituents independently selected from $C_{1-6}$ alkyl, oxo, carboxy and $C_{2-6}$ alkoxycarbonyl.

Suitable examples of particular substituents on $R^{21}$ include one, two or three substituents independently selected from fluoro, fluoromethyl, chloro, bromo, cyano, cyanomethyl, cyanoethyl, nitro, nitromethyl, methyl, ethyl, isopropyl, trifluoromethyl, trifluoroethyl, ethenyl, hydroxy, hydroxymethyl, methoxy, ethoxy, difluoromethoxy, trifluoromethoxy, trifluoroethoxy, methylthio, methylsulphonyl, methylsulphonylmethyl, methylsulphonylethyl, oxo, amino, methylamino, dimethylamino, acetylamino, acetylaminomethyl, methoxycarbonylamino, ethoxycarbonylamino, tert-butoxycarbonylamino, methylsulphonylamino, formyl, acetyl, carboxy, carboxymethyl, carboxyethyl, methoxycarbonyl, ethoxycarbonyl, n-butoxycarbonyl, tert-butoxycarbonyl, morpholinylethoxycarbonyl, methoxycarbonylmethyl, ethoxycarbonylmethyl, ethoxycarbonylethyl, ethoxycarbonylmethylidenyl, acetylaminosulphonyl, methoxyaminocarbonyl, tetrazolyl, tetrazolylmethyl, hydroxyoxadiazolyl, aminocarbonyl, methylaminocarbonyl, dimethylaminocarbonyl, methylsulphonylaminocarbonyl, aminosulphonyl, methylaminosulphonyl, dimethylaminosulphonyl, methylsulphoximinyl and (methyl)(N-methyl)sulphoximinyl.

Selected examples of particular substituents on $R^{21}$ include one, two or three substituents independently selected from methyl, oxo, carboxy, methoxycarbonyl and ethoxycarbonyl.

Typically, $R^{21}$ represents hydrogen, fluoro, fluoroisopropyl, cyano, methyl, trifluoromethyl, ethenyl, hydroxy, hydroxyisopropyl, methoxy, isopropoxy, trifluoroethoxy, carboxycyclobutyloxy, methylthio, methylsulphonyl, amino, methylamino, dimethylamino, methoxyethylamino, N-(hydroxyethyl)-N-(methyl)amino, N-[carboxyethyl]-N-methylamino, carboxycyclopentylamino, carboxycyclopropylmethylamino, methylsulphonylamino, acetoxyisopropyl, carboxy, ethoxycarbonylethyl, fluoromethyl-cyclopropyl, acetylaminomethylcyclopropyl, hydroxycyclobutyl, carboxycyclopentyl, carboxycyclohexyl, (carboxy)(methyl)cyclohexyl, (carboxy)(hydroxy)cyclohexyl, carboxymethylcyclohexyl, ethoxycarbonylcyclohexyl, (methoxycarbonyl)(methyl)-cyclohexyl, (ethoxycarbonyl)(methyl)cyclohexyl, carboxycyclohexylmethyl, carboxycyclohexenyl, ethoxycarbonylcyclohexenyl, carboxybicyclo[3.1.0]hexanyl, ethoxycarbonylbicyclo[3.1.0]hexanyl, carboxybicyclo[4.1.0]heptanyl, carboxybicyclo-[2.2.2]octanyl, fluorooxetanyl, hydroxyoxetanyl, hydroxyazetidinyl, (hydroxy)(methyl)-azetidinyl, carboxyazetidinyl, (tert-butoxycarbonyl)(hydroxy)azetidinyl, tetrazolyl-azetidinyl, hydroxytetrahydrofuranyl, pyrrolidinyl, hydroxypyrrolidinyl, carboxypyrrolidinyl, (carboxy)(methyl)pyrrolidinyl, carboxymethylpyrrolidinyl, ethoxycarbonyl-pyrrolidinyl, fluorotetrahydropyranyl, hydroxytetrahydropyranyl, piperidinyl, difluoro-piperidinyl, (cyano)(methyl)piperidinyl, (hydroxy)(nitromethyl)piperidinyl, (hydroxy)-(methyl)piperidinyl, (hydroxy)(trifluoromethyl)piperidinyl, (hydroxymethyl)(methyl)-piperidinyl, methylsulphonylpiperidinyl, oxopiperidinyl, (formyl)(methyl)piperidinyl, acetylpiperidinyl, carboxypiperidinyl, (carboxy)(fluoro)piperidinyl, (carboxy)(methyl)-piperidinyl, (carboxy)(ethyl)piperidinyl, (carboxy)(trifluoromethyl)piperidinyl, (carboxy)-(hydroxy)piperidinyl, (carboxy)(hydroxymethyl)piperidinyl, (carboxy)(methoxy)-piperidinyl, (amino)(carboxy)piperidinyl, carboxymethylpiperidinyl, methoxycarbonyl-piperidinyl, (methoxycarbonyl)(methyl)piperidinyl, (ethyl)(methoxycarbonyl)piperidinyl, (isopropyl)(methoxycarbonyl)piperidinyl, (methoxy)(methoxycarbonyl)piperidinyl, (carboxy)(methoxycarbonyl)piperidinyl, ethoxycarbonylpiperidinyl, (ethoxycarbonyl)-(fluoro)piperidinyl, (ethoxycarbonyl)(methyl)piperidinyl, (ethoxycarbonyl)(trifluoromethyl)piperidinyl, (ethoxycarbonyl)(hydroxymethyl)piperidinyl, (n-butoxycarbonyl)-(methyl)piperidinyl, (methyl)(morpholinylethoxycarbonyl)piperidinyl, ethoxycarbonyl-methylpiperidinyl, methylsulphonylaminocarbonylpiperidinyl, acetylaminosulphonyl-piperidinyl, methoxyaminocarbonylpiperidinyl, tetrazolylpiperidinyl, hydroxyoxadiazolyl-piperidinyl, aminosulphonylpiperidinyl, piperazinyl, cyanoethylpiperazinyl, trifluoroethyl-piperazinyl, methylsulphonylpiperazinyl, methylsulphonylethylpiperazinyl, oxopiperazinyl, acetylpiperazinyl, carboxypiperazinyl, tert-butoxycarbonylpiperazinyl, carboxymethylpiperazinyl, carboxyethylpiperazinyl, ethoxycarbonylmethylpiperazinyl, ethoxycarbonylethylpiperazinyl, tetrazolylmethylpiperazinyl, trioxohexahydro-[1,2,5]thiadiazolo[2,3-a]pyrazinyl, morpholinyl, dimethylmorpholinyl, hydroxymethyl-morpholinyl, carboxymorpholinyl, (carboxy)(methyl)morpholinyl, carboxymethyl-morpholinyl, thiomorpholinyl, oxothiomorpholinyl, dioxothiomorpholinyl, carboxy-azepanyl, carboxyoxazepanyl, oxodiazepanyl, (methyl)(oxo)diazepanyl, dioxo-thiadiazepanyl, carboxy-3-azabicyclo[3.1.0]hexanyl, (carboxy)(methyl)-3-azabicyclo-[3.1.0]hexanyl, methoxycarbonyl-3-azabicyclo[3.1.0]hexanyl, ethoxycarbonyl-3-azabicyclo[3.1.0]hexanyl, 2-oxa-5-azabicyclo[2.2.1]heptanyl, carboxy-2-oxa-5-azabicyclo[2.2.1]heptanyl, carboxy-3-azabicyclo[3.1.1]heptanyl, carboxy-3-azabicyclo-[4.1.0]heptanyl, methoxycarbonyl-3-azabicyclo[4.1.0]heptanyl, ethoxycarbonyl-3-azabicyclo[4.1.0]heptanyl, (hydroxy)(methyl)(oxo)-2-oxabicyclo[2.2.2]octanyl, carboxy-3-azabicyclo[3.2.1]octanyl, methoxycarbonyl-3-azabicyclo[3.2.1]octanyl, oxo-8-azabicyclo[3.2.1]octanyl, ethoxycarbonylmethylidenyl-8-azabicyclo[3.2.1]octanyl, 3-oxa-8-azabicyclo[3.2.1]octanyl, oxo-3,6-diazabicyclo[3.2.2]nonanyl, carboxy-3-oxa-7-azabicyclo[3.3.1]nonanyl, carboxy-5-azaspiro[2.3]hexanyl, (carboxy)(methyl)-5-azaspiro-[2.3]hexanyl, carboxy-5-azaspiro[2.4]heptanyl, carboxy-2-azaspiro[3.3]heptanyl, 2-oxa-6-azaspiro[3.3]heptanyl, 2-oxa-6-azaspiro[3.4]octanyl, 2-oxa-6-azaspiro[3.5]nonanyl, 2-oxa-7-azaspiro[3.5]nonanyl or (dioxo)(methyl)-2,4,8-triazaspiro[4.5]decanyl.

Selected values of $R^{21}$ include hydroxyisopropyl, carboxycyclohexyl, carboxybicyclo[3.1.0]hexanyl, (carboxy)(methyl)piperidinyl, (ethoxycarbonyl)(methyl)piperidinyl, piperazinyl, oxopiperazinyl, morpholinyl, oxodiazepanyl, carboxy-3-azabicyclo[3.2.1]-octanyl and methoxycarbonyl-3-azabicyclo[3.2.1]octanyl.

Illustrative values of $R^{21}$ include hydroxyisopropyl, carboxybicyclo[3.1.0]hexanyl, (carboxy)(methyl)piperidinyl, (ethoxycarbonyl)(methyl)piperidinyl, piperazinyl, morpholinyl, oxodiazepanyl, carboxy-3-azabicyclo[3.2.1]octanyl and methoxycarbonyl-3-azabicyclo[3.2.1]octanyl.

In a particular embodiment, $R^{21}$ represents hydroxy $C_{1-6}$alkyl. In one aspect of that embodiment, $R^{21}$ represents hydroxyisopropyl, especially 2-hydroxyprop-2-yl.

Generally, $R^{22}$ represents hydrogen or $C_{1-6}$ alkyl.

Suitably, $R^{22}$ represents hydrogen, chloro or methyl.

Typically, $R^{22}$ represents hydrogen or methyl.

In one embodiment, $R^{22}$ represents hydrogen. In another embodiment, $R^{22}$ represents $C_{1-6}$ alkyl, especially methyl. In a further embodiment, $R^{22}$ represents halogen. In one aspect of that embodiment, $R^{22}$ represents fluoro. In another aspect of that embodiment, $R^{22}$ represents chloro.

Generally, $R^{23}$ represents hydrogen or $C_{1-6}$ alkyl.

Suitably, $R^{23}$ represents hydrogen, methyl, trifluoromethyl or methoxy.

Typically, $R^{23}$ represents hydrogen or methyl.

In one embodiment, $R^{23}$ represents hydrogen. In another embodiment, $R^{23}$ represents $C_{1-6}$ alkyl, especially methyl. In a further embodiment, $R^{23}$ represents trifluoromethyl. In an additional embodiment, $R^{23}$ represents $C_{1-6}$ alkoxy, especially methoxy.

A particular sub-group of the compounds of formula (IIA-B) above is represented by the compounds of formula (IIB-B) and N-oxides thereof, and pharmaceutically acceptable salts and solvates thereof, and glucuronide derivatives thereof, and co-crystals thereof:

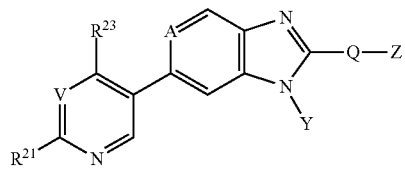

(IIB-B)

wherein A, Y, Q, Z, V, $R^{21}$ and $R^{23}$ are as defined above.

A particular sub-group of the compounds of formula (IIA-C) above is represented by the compounds of formula (IIB-C) and N-oxides thereof, and pharmaceutically acceptable salts and solvates thereof, and glucuronide derivatives thereof, and co-crystals thereof:

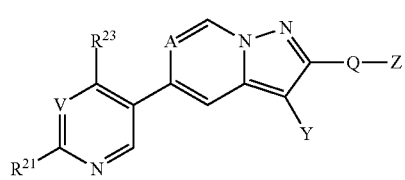

(IIB-C)

wherein A, Y, Q, Z, V, $R^{21}$ and $R^{23}$ are as defined above.

Particular sub-groups of the compounds of formula (IIB-A) above are represented by the compounds of formula (IIC-A), (IID-A), (IIE-A), (IIF-A), (IIG-A), (IIH-A), (IIJ-A), (IIK-A) and (IIL-A), and N-oxides thereof, and pharmaceutically acceptable salts and solvates thereof, and glucuronide derivatives thereof, and co-crystals thereof:

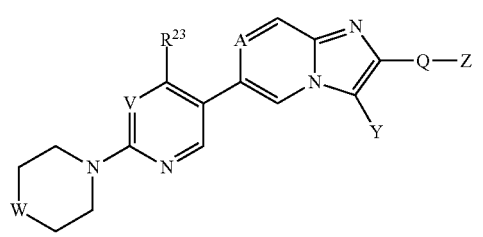

(IIC-A)

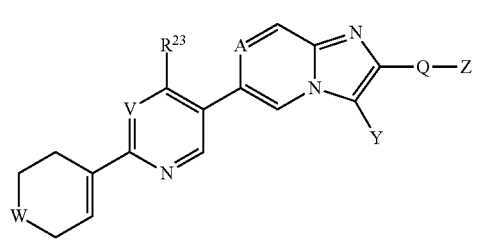

(IID-A)

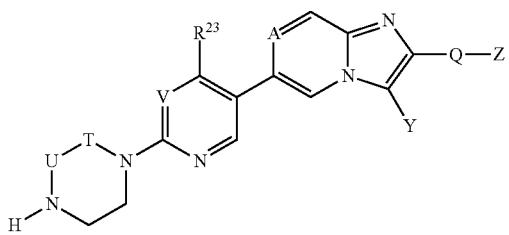

(IIE-A)

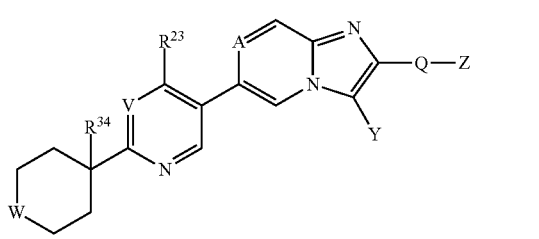

(IIF-A)

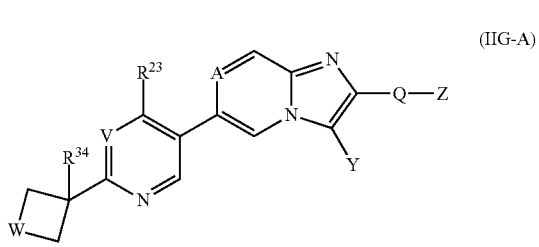

(IIG-A)

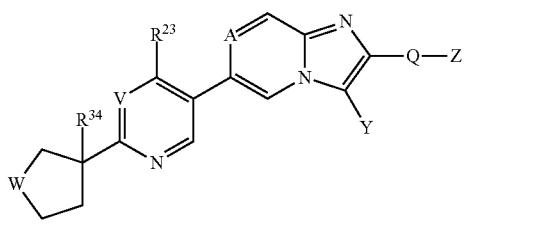

(IIH-A)

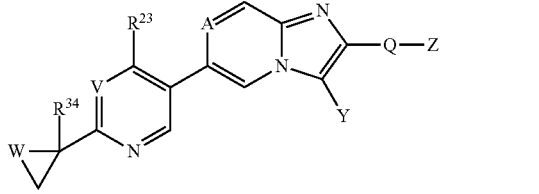

(IIJ-A)

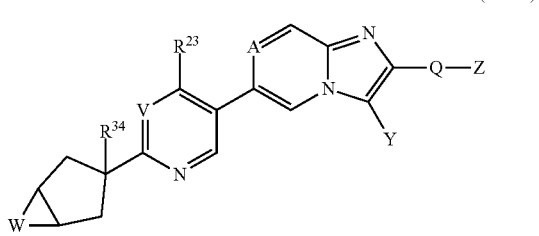

(IIK-A)

-continued

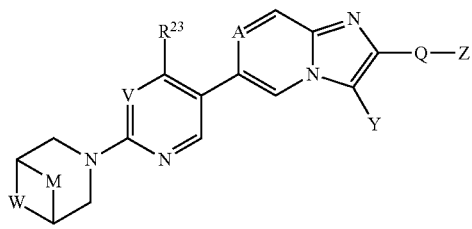

(III-A)

wherein

T represents —CH$_2$— or —CH$_2$CH$_2$—;

U represents C(O) or S(O)$_2$;

W represents O, S, S(O), S(O)$_2$, S(O)(NR$^6$), N(R$^{31}$) or C(R$^{32}$)(R$^{33}$);

-M- represents —CH$_2$— or —CH$_2$CH$_2$—;

R$^{31}$ represents hydrogen, cyano(C$_{1-6}$)alkyl, C$_{1-6}$ alkyl, trifluoromethyl, trifluoroethyl, C$_{1-6}$ alkylsulphonyl, (C$_{1-6}$)alkylsulphonyl(C$_{1-6}$)alkyl, formyl, C$_{2-6}$ alkylcarbonyl, carboxy, carboxy(C$_{1-6}$)alkyl, C$_{2-6}$ alkoxycarbonyl, C$_{2-6}$ alkoxycarbonyl(C$_{1-6}$)alkyl, a carboxylic acid isostere or prodrug moiety Ω, —(C$_{1-6}$)alkyl-Ω, aminocarbonyl, C$_{1-6}$ alkylaminocarbonyl, di(C$_{1-6}$)alkylaminocarbonyl, aminosulphonyl or di(C$_{1-6}$)alkylaminosulphonyl;

R$^{32}$ represents hydrogen, halogen, cyano, hydroxy, hydroxy(C$_{1-6}$)alkyl, C$_{1-6}$ alkylsulphonyl, formyl, C$_{2-6}$ alkylcarbonyl, carboxy, carboxy(C$_{1-6}$)alkyl, C$_{2-6}$ alkoxycarbonyl, C$_{2-6}$ alkoxycarbonyl(C$_{1-6}$)alkyl, aminosulphonyl, (C$_{1-6}$)alkylsulphoximinyl, [(C$_{1-6}$)alkyl][N—(C$_{1-6}$)alkyl]sulphoximinyl, a carboxylic acid isostere or prodrug moiety Ω, or —(C$_{1-6}$)alkyl-Ω;

R$^{33}$ represents hydrogen, halogen, C$_{1-6}$ alkyl, trifluoromethyl, hydroxy, hydroxy-(C$_{1-6}$)alkyl, C$_{1-6}$ alkoxy, amino or carboxy;

R$^{34}$ represents hydrogen, halogen, halo(C$_{1-6}$)alkyl, hydroxy, C$_{1-6}$ alkoxy, C$_{1-6}$ alkylthio, C$_{1-6}$ alkylsulphinyl, C$_{1-6}$ alkylsulphonyl, amino, C$_{1-6}$ alkylamino, di(C$_{1-6}$)alkylamino, (C$_{2-6}$)alkylcarbonylamino, (C$_{2-6}$)alkylcarbonylamino(C$_{1-6}$)alkyl, (C$_{1-6}$)alkylsulphonylamino or (C$_{1-6}$)alkylsulphonylamino(C$_{1-6}$)alkyl; and A, Y, Q, Z, V, R$^6$, R$^{23}$ and Ω are as defined above.

In a first embodiment, T represents —CH$_2$—. In a second embodiment, T represents —CH$_2$CH$_2$—.

In a first embodiment, U represents C(O). In a second embodiment, U represents S(O)$_2$.

Generally, W represents O, S(O)$_2$, N(R$^{31}$) or C(R$^{32}$)(R$^{33}$). Typically, W represents O, N(R$^{31}$) or C(R$^{32}$)(R$^{33}$).

In a first embodiment, W represents O. In a second embodiment, W represents S. In a third embodiment, W represents S(O). In a fourth embodiment, W represents S(O)$_2$. In a fifth embodiment, W represents S(O)(NR$^6$). In a sixth embodiment, W represents N(R$^{31}$). In a seventh embodiment, W represents C(R$^{32}$)(R$^{33}$).

In one embodiment, -M- represents —CH$_2$—. In another embodiment, -M- represents —CH$_2$CH$_2$—.

Typically, R$^{31}$ represents hydrogen, cyano(C$_{1-6}$)alkyl, C$_{1-6}$ alkyl, trifluoromethyl, trifluoroethyl, C$_{1-6}$ alkylsulphonyl, (C$_{1-6}$)alkylsulphonyl(C$_{1-6}$)alkyl, formyl, C$_{2-6}$ alkylcarbonyl, carboxy, carboxy(C$_{1-6}$)alkyl, C$_{2-6}$ alkoxycarbonyl, C$_{2-6}$ alkoxycarbonyl-(C$_{1-6}$)alkyl, tetrazolyl(C$_{1-6}$)alkyl, aminocarbonyl, C$_{1-6}$ alkylaminocarbonyl, di(C$_{1-6}$)alkylaminocarbonyl, aminosulphonyl, C$_{1-6}$ alkylaminosulphonyl or di(C$_{1-6}$)alkylaminosulphonyl.

Typical values of R$^{31}$ include hydrogen, cyanoethyl, methyl, ethyl, isopropyl, trifluoromethyl, trifluoroethyl, methylsulphonyl, methylsulphonylethyl, formyl, acetyl, carboxy, carboxymethyl, carboxyethyl, methoxycarbonyl, ethoxycarbonyl, tert-butoxycarbonyl, ethoxycarbonylmethyl, ethoxycarbonylethyl, tetrazolylmethyl, aminocarbonyl, methylamino-carbonyl, dimethylaminocarbonyl, aminosulphonyl, methylaminosulphonyl and dimethylaminosulphonyl.

A particular value of R$^{31}$ is hydrogen.

Generally, R$^{32}$ represents halogen, carboxy, carboxy (C$_{1-6}$)alkyl, C$_{2-6}$ alkoxycarbonyl, C$_{2-6}$ alkoxycarbonyl(C$_{1-6}$)alkyl, a carboxylic acid isostere or prodrug moiety Ω, or —(C$_{1-6}$)alkyl-Ω.

Typically, R$^{32}$ represents hydrogen, halogen, cyano, hydroxy, hydroxy(C$_{1-6}$)alkyl, C$_{1-6}$ alkylsulphonyl, formyl, carboxy, carboxy(C$_{1-6}$)alkyl, C$_{2-6}$ alkoxycarbonyl, C$_{2-6}$ alkoxycarbonyl(C$_{1-6}$)alkyl, aminosulphonyl, (C$_{1-6}$)alkylsulphoximinyl, [(C$_{1-6}$)alkyl][N—(C$_{1-6}$)alkyl]sulphoximinyl, (C$_{1-6}$)alkylsulphonylaminocarbonyl, (C$_{2-6}$)alkylcarbonylaminosulphonyl, (C$_{1-6}$)alkoxyaminocarbonyl, tetrazolyl or hydroxyoxadiazolyl.

Suitably, R$^{32}$ represents carboxy or C$_{2-6}$ alkoxycarbonyl.

Typical values of R$^{32}$ include hydrogen, fluoro, cyano, hydroxy, hydroxymethyl, methylsulphonyl, formyl, carboxy, carboxymethyl, carboxyethyl, methoxycarbonyl, ethoxycarbonyl, tert-butoxycarbonyl, methoxycarbonylmethyl, methoxycarbonylethyl, ethoxycarbonylmethyl, ethoxycarbonylethyl, aminosulphonyl, methylsulphoximinyl, (methyl)(N-methyl)sulphoximinyl, methylsulphonylaminocarbonyl, acetylaminosulphonyl, methoxyaminocarbonyl, tetrazolyl and hydroxyoxadiazolyl.

Suitable values of R$^{32}$ include carboxy, methoxycarbonyl and ethoxycarbonyl.

In a selected embodiment, R$^{32}$ represents carboxy.

Generally, R$^{33}$ represents hydrogen, halogen or C$_{1-6}$ alkyl. Suitably, R$^{33}$ represents hydrogen or C$_{1-6}$ alkyl.

Selected values of R$^{33}$ include hydrogen, fluoro, methyl, ethyl, isopropyl, trifluoromethyl, hydroxy, hydroxymethyl, methoxy, amino and carboxy.

Particular values of R$^{33}$ include hydrogen and methyl.

In a first embodiment, R$^{33}$ represents hydrogen. In a second embodiment, R$^{33}$ represents halogen. In one aspect of that embodiment, R$^{33}$ represents fluoro. In a third embodiment, R$^{33}$ represents C$_{1-6}$ alkyl. In a first aspect of that embodiment, R$^{33}$ represents methyl. In a second aspect of that embodiment, R$^{33}$ represents ethyl. In a third aspect of that embodiment, R$^{33}$ represents isopropyl. In a fourth embodiment, R$^{33}$ represents trifluoromethyl. In a fifth embodiment, R$^{33}$ represents hydroxy. In a sixth embodiment, R$^{33}$ represents hydroxy(C$_{1-6}$)alkyl. In one aspect of that embodiment, R$^{33}$ represents hydroxymethyl. In a seventh embodiment, R$^{33}$ represents C$_{1-6}$ alkoxy. In one aspect of that embodiment, R$^{33}$ represents methoxy. In an eighth embodiment, R$^{33}$ represents amino. In a ninth embodiment, R$^{33}$ represents carboxy.

In a first embodiment, R$^{34}$ represents hydrogen. In a second embodiment, R$^{34}$ represents halogen. In one aspect of that embodiment, R$^{34}$ represents fluoro. In a third embodiment, R$^{34}$ represents halo(C$_{1-6}$)alkyl. In one aspect of that embodiment, R$^{34}$ represents fluoromethyl. In a fourth embodiment, R$^{34}$ represents hydroxy. In a fifth embodiment, R$^{34}$ represents C$_{1-6}$ alkoxy, especially methoxy. In a sixth embodiment, R$^{34}$ represents C$_{1-6}$ alkylthio, especially methylthio. In a seventh embodiment, $R^{34}$ represents $C_{1-6}$ alkylsulphinyl, especially methylsulphinyl. In an eighth embodiment, $R^{34}$ represents $C_{1-6}$ alkylsulphonyl, especially methylsulphonyl. In a ninth embodiment, $R^{34}$ represents amino. In a tenth embodiment, $R^{34}$ represents $C_{1-6}$ alkylamino, especially methylamino. In an eleventh embodiment, $R^{34}$ represents di($C_{1-6}$)alkylamino, especially dimethylamino. In a twelfth embodiment, $R^{34}$ represents $(C_{2-6})$ alkylcarbonylamino, especially acetylamino. In a thirteenth embodiment, $R^{34}$ represents $(C_{2-6})$alkylcarbonylamino$(C_{1-6})$alkyl, especially acetylaminomethyl. In a fourteenth embodiment, $R^{34}$ represents $(C_{1-6})$alkylsulphonylamino, especially methylsulphonylamino. In a fifteenth embodiment, $R^{34}$ represents $(C_{1-6})$alkylsulphonylamino$(C_{1-6})$alkyl, especially methylsulphonylaminomethyl.

Typically, $R^{34}$ represents hydrogen, halogen, halo($C_{1-6}$)alkyl, hydroxy or $(C_{2-6})$alkylcarbonylamino$(C_{1-6})$alkyl.

Selected values of $R^{34}$ include hydrogen, fluoro, fluoromethyl, hydroxy, methoxy, methylthio, methylsulphinyl, methylsulphonyl, amino, methylamino, dimethylamino and acetylaminomethyl.

Particular values of $R^{34}$ include hydrogen, fluoro, fluoromethyl, hydroxy and acetylaminomethyl.

Suitably, $R^{34}$ represents hydrogen or hydroxy.

Particular sub-groups of the compounds of formula (IIB-B) above are represented by the compounds of formula (IIC-B), (IID-B), (IIE-B), (IIF-B), (IIG-B), (IIH-B), (IIJ-B), (IIK-B) and (IIL-B), and N-oxides thereof, and pharmaceutically acceptable salts and solvates thereof, and glucuronide derivatives thereof, and co-crystals thereof:

(IIC-B)

(IID-B)

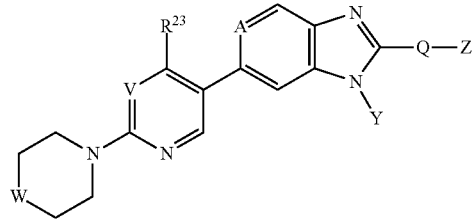

(IIE-B)

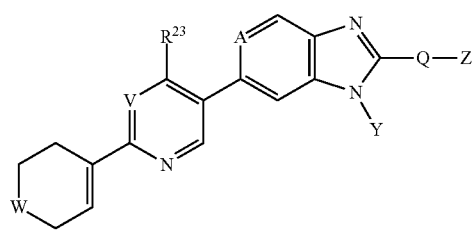

(IIE-B)

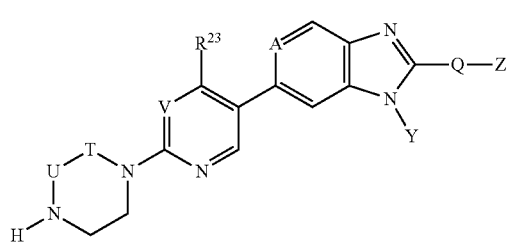

(IIF-B)

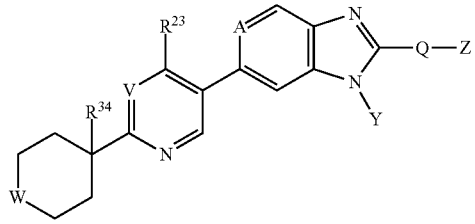

(IIG-B)

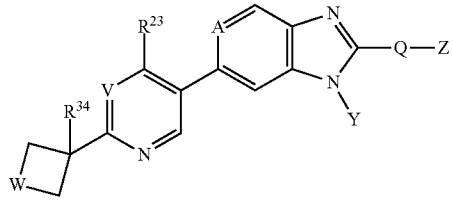

(IIH-B)

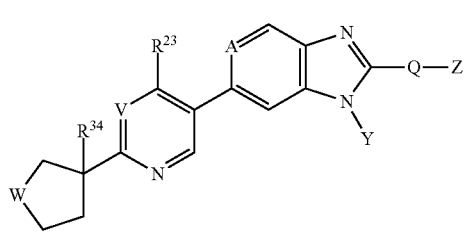

(IIJ-B)

(IIK-B)

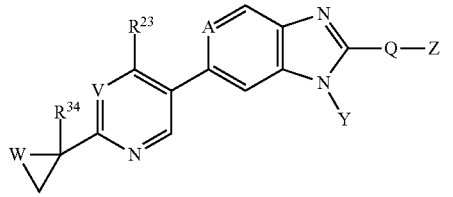

(IIL-B)

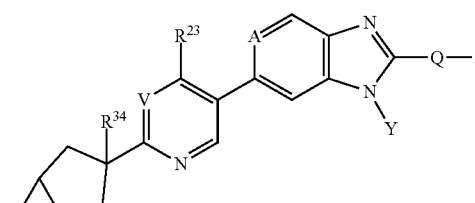

wherein A, Y, Q, Z, M, T, U, V, W, $R^{23}$ and $R^{34}$ are as defined above.

Particular sub-groups of the compounds of formula (IIB-C) above are represented by the compounds of formula (IIC-C), (IID-C), (IIE-C), (IIF-C), (IIG-C), (IIH-C), (IIJ-C), (IIK-C) and (IIL-C), and N-oxides thereof, and pharmaceutically acceptable salts and solvates thereof, and glucuronide derivatives thereof, and co-crystals thereof:

(IIC-C)
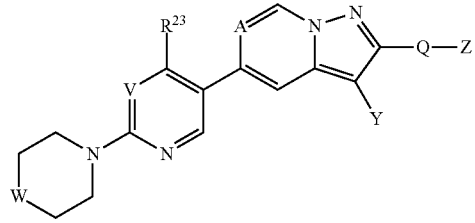

(IID-C)
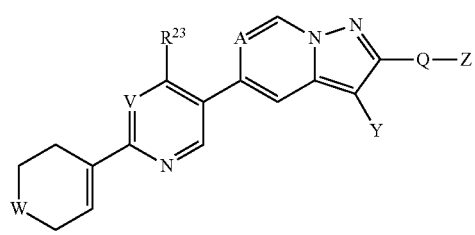

(IIE-C)
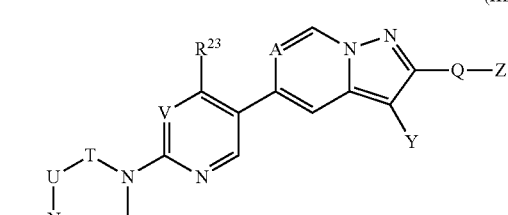

(IIF-C)
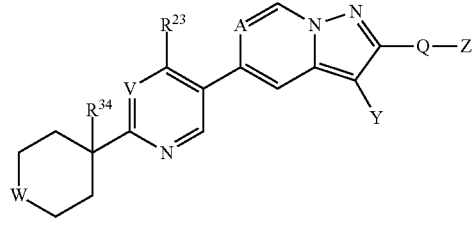

(IIG-C)
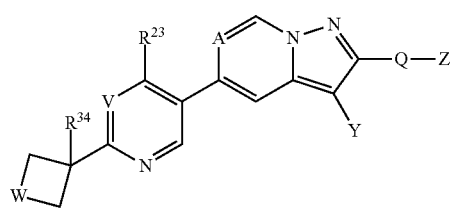

(IIH-C)
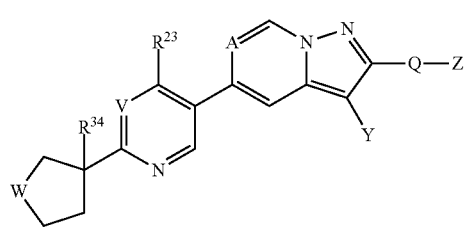

(IIJ-C)
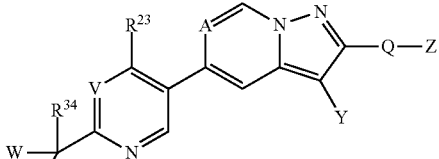

(IIK-C)
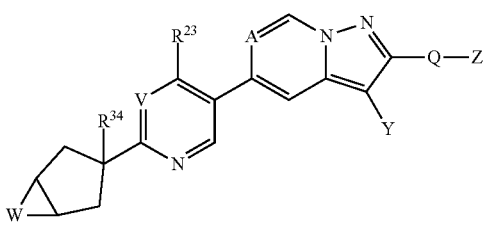

(IIL-C)
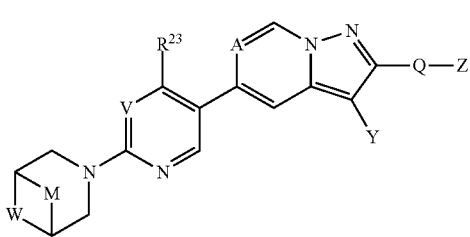

wherein A, Y, Q, Z, M, T, U, V, W, $R^{23}$ and $R^{34}$ are as defined above.

An alternative sub-class of compounds of formula (IIA-A) above is represented by the compounds of formula (IIM-A) and N-oxides thereof, and pharmaceutically acceptable salts and solvates thereof, and glucuronide derivatives thereof, and co-crystals thereof:

(IIM-A)
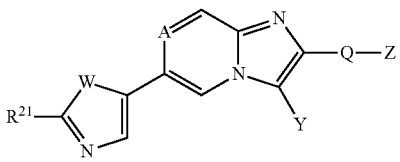

wherein
A, Y, Q, Z, W and $R^{21}$ are as defined above.

An alternative sub-class of compounds of formula (IIA-B) above is represented by the compounds of formula (IIM-B) and N-oxides thereof, and pharmaceutically acceptable salts and solvates thereof, and glucuronide derivatives thereof, and co-crystals thereof:

(IIM-B)
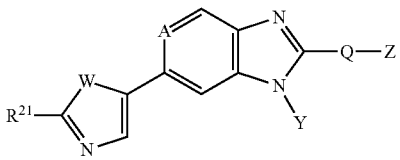

wherein
A, Y, Q, Z, W and $R^{21}$ are as defined above.

An alternative sub-class of compounds of formula (IIA-C) above is represented by the compounds of formula (IIM-C)

and N-oxides thereof, and pharmaceutically acceptable salts and solvates thereof, and glucuronide derivatives thereof, and co-crystals thereof:

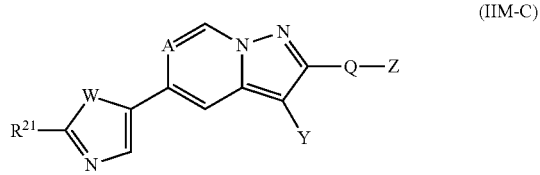

(IIM-C)

wherein

A, Y, Q, Z, W and $R^{21}$ are as defined above.

With specific reference to formula (IIM-A), (IIM-B) and (IIM-C), the integer W is suitably O, S or N—$R^{31}$, especially S or N—$R^{31}$.

Specific novel compounds in accordance with the present invention include each of the compounds whose preparation is described in the accompanying Examples, and pharmaceutically acceptable salts and solvates thereof, and co-crystals thereof.

The compounds in accordance with the present invention are beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, psoriatic arthropathy, vasculitis, polymyositis, scleroderma, multiple sclerosis, systemic sclerosis, ankylosing spondylitis, rheumatoid arthritis, non-specific inflammatory arthritis, juvenile inflammatory arthritis, juvenile idiopathic arthritis (including oligoarticular and polyarticular forms thereof), anemia of chronic disease (ACD), Still's disease (juvenile and/or adult onset), Behçet's disease and Sjögren's syndrome. Autoimmune endocrine disorders include thyroiditis. Organ-specific autoimmune disorders include Addison's disease, haemolytic or pernicious anemia, acute kidney injury (AKI; including cisplatin-induced AKI), diabetic nephropathy (DN), obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis (LN), minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease (COPD), respiratory distress syndrome, sepsis, fever, muscular dystrophy (including Duchenne muscular dystrophy) and organ transplant rejection (including kidney allograft rejection).

Neurological and neurodegenerative disorders include Alzheimer's disease, Parkinson's disease, Huntington's disease, ischaemia, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction). Modulators of TNFα function may also be of use in the treatment and/or prevention of myocardial infarction (see J. J. Wu et al., *JAMA*, 2013, 309, 2043-2044).

Metabolic disorders include diabetes (including insulin-dependent diabetes mellitus and juvenile diabetes), dyslipidemia and metabolic syndrome.

Ocular disorders include retinopathy (including diabetic retinopathy, proliferative retinopathy, non-proliferative retinopathy and retinopathy of prematurity), macular oedema (including diabetic macular oedema), age-related macular degeneration (ARMD), vascularisation (including corneal vascularisation and neovascularisation), retinal vein occlusion, and various forms of uveitis and keratitis.

Oncological disorders, which may be acute or chronic, include proliferative disorders, especially cancer, and cancer-associated complications (including skeletal complications, cachexia and anemia). Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT 1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle. Modulators of TNFα function may also be used to increase the safety of the potent anticancer effect of TNF (see F. V. Hauwermeiren et al., *J. Clin. Invest.*, 2013, 123, 2590-2603).

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (IA), (IB) or (IC) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (IA), (IB) or (IC) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule such as methotrexate or prednisolone.

The compounds of formula (IA), (IB) and (IC) above may be prepared by a process which comprises reacting a compound of formula Y-L$^1$ with a compound of formula (IIIA), (IIIB) or (IIIC):

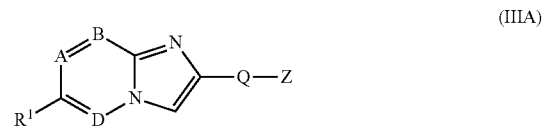

(IIIA)

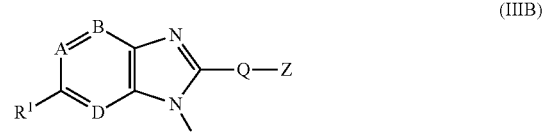

(IIIB)

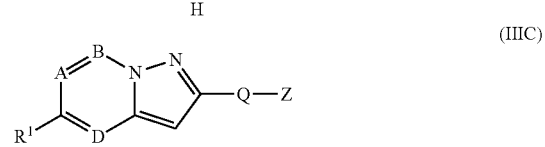

(IIIC)

wherein A, B, D, Y, Q, Z and R$^1$ are as defined above, and L$^1$ represents a displaceable group.

The displaceable group L$^1$ is suitably hydroxy, methoxy or dimethylamino.

The procedure is suitably effected in the presence of an acid such as pyridinium p-toluenesulfonate. The reaction is conveniently carried out at an elevated temperature in a suitable solvent, e.g. acetonitrile.

In an alternative procedure, the compounds of formula (IA) above wherein E represents —O— may be prepared by a two-step procedure which comprises: (i) reacting a compound of formula (IV) with a compound of formula (V):

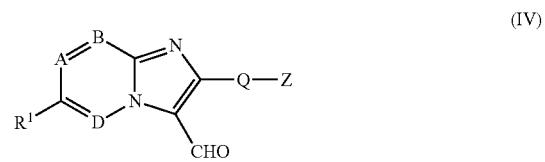

(IV)

-continued

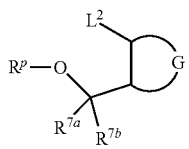

(V)

wherein A, B, D, G, Q, Z, $R^1$, $R^{7a}$ and $R^{7b}$ are as defined above, $R^p$ represents hydrogen or a hydroxy-protecting group, and $L^2$ represents hydrogen or a halogen atom, e.g. bromo, or $L^2$ represents —MgBr; followed, where necessary, by removal of the hydroxy-protecting group $R^p$; and (ii) treatment with an acid.

The hydroxy-protecting group $R^p$ will suitably be 2-methoxyethoxymethyl or tetrahydropyran-2-yl.

Where $L^2$ represents hydrogen or a halogen atom, step (i) will generally be carried out in the presence of a base, e.g. an organolithium reagent such as n-butyllithium. The reaction is conveniently effected in a suitable solvent, e.g. a hydrocarbon solvent such as toluene or pentane, or a cyclic ether such as tetrahydrofuran, optionally in the presence of N,N,N',N'-tetramethylethylenediamine.

Where $L^2$ represents —MgBr, step (i) is conveniently effected in a suitable solvent, e.g. a cyclic ether such as tetrahydrofuran, typically at a temperature in the region of 0° C.

Removal of the hydroxy-protecting group $R^p$, where necessary, will conveniently be effected by treatment with a mineral acid, e.g. hydrochloric acid.

The acid employed in step (ii) will typically be a mineral acid such as hydrochloric acid. The reaction is conveniently effected in a suitable solvent, e.g. a cyclic ether such as 1,4-dioxane, or a chlorinated solvent such as dichloromethane.

In another procedure, the compounds of formula (IA) above wherein E represents —O— and $R^{7a}$ and $R^{7b}$, when taken together with the carbon atom to which they are both attached, represent carbonyl (C=O), may be prepared by a three-step procedure which comprises: (i) reacting a compound of formula (IV) as defined above with a compound of formula (VA):

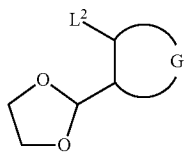

(VA)

wherein $L^2$ is as defined above; (ii) removal of the cyclic ketal protecting group, followed by intramolecular cyclisation of the resulting material; and (iii) oxidation of the material thereby obtained.

Step (i) may conveniently be effected under conditions analogous to those described above for the reaction between compounds (IV) and (V).

Step (ii) may conveniently be effected by treatment with a mineral acid, e.g. hydrochloric acid.

The oxidising agent employed in step (iii) will suitably be tetrapropylammonium perruthenate.

The intermediates of formula (IV) above may be prepared by treating a compound of formula (IIIA) as defined above with phosphorus oxychloride and N,N-dimethylformamide.

Alternatively, the intermediates of formula (IV) above may be prepared by a two-step procedure which comprises: (i) treatment of a compound of formula (IIIA) as defined above with formaldehyde; and (ii) treatment of the resulting compound with an oxidising agent, e.g. Dess-Martin periodinane.

The intermediates of formula (V) and (VA) above wherein $L^2$ represents —MgBr may be prepared from the corresponding compound wherein $L^2$ represents bromo by treatment with magnesium. The reaction is conveniently effected at an elevated temperature in a suitable solvent, e.g. a cyclic ether such as tetrahydrofuran.

The intermediates of formula (IIIA) above may be prepared by reacting a compound of formula (VI) with a compound of formula (VII) or an acetal derivative thereof, e.g. the dimethyl acetal derivative:

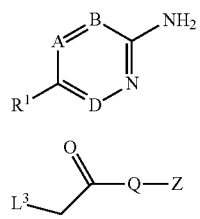

(VI)

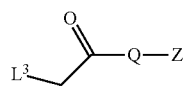

(VII)

wherein A, B, D, Q, Z and $R^1$ are as defined above, and $L^3$ represents a suitable leaving group.

The leaving group $L^3$ is typically a halogen atom, e.g. chloro or bromo.

The reaction is conveniently effected at an elevated temperature in a suitable solvent, e.g. a $C_{1-4}$ alkanol such as ethanol or isopropanol.

In another procedure, the compounds of formula (IA) above wherein E represents —O— and $R^{7a}$ and $R^{7b}$, when taken together with the carbon atom to which they are both attached, represent carbonyl (C=O), may be prepared by reacting a compound of formula (IIIA) as defined above with a compound of formula (VB):

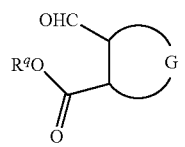

(VB)

wherein G is as defined above, and $R^q$ represents $C_{1-6}$ alkyl.

Suitably, $R^q$ represents methyl or ethyl. In one embodiment, $R^q$ represents methyl. In another embodiment, $R^q$ represents ethyl.

The reaction is conveniently effected at an elevated temperature in a suitable solvent, e.g. a cyclic ether such as 1,4-dioxane.

The intermediates of formula (IIIB) above may be prepared by reacting a compound of formula Z-Q-$CO_2$H or a carboxylate salt thereof (e.g. a carboxylate salt with an alkali metal such as lithium, sodium or potassium) with a compound of formula (VIII):

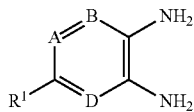

(VIII)

wherein Q, Z, A, B, D and R¹ are as defined above.

The reaction may advantageously be performed in the presence of a peptide coupling reagent such as 1-[bis(dimethylamino)methylene]-1H-1,2,3-triazolo[4,5-b]-pyridinium 3-oxid hexafluorophosphate (HATU), optionally in the presence of a suitable base, e.g. an organic base such as N,N-diisopropylethylamine. The reaction is conveniently effected at ambient or elevated temperature in a suitable solvent, e.g. N,N-dimethylformamide or a chlorinated solvent such as dichloromethane. The product thereby obtained is suitably treated with an acid, ideally an organic acid such as acetic acid, or a mineral acid such as hydrochloric acid, typically at an elevated temperature.

Alternatively, the reaction may conveniently be effected in the presence of a coupling reagent such as 1-(3-dimethylaminopropyl)-3-ethylcarbodiimide hydrochloride (EDC), typically at ambient temperature in a suitable solvent, e.g. a chlorinated solvent such as dichloromethane, in the presence of a suitable base, e.g. an organic base such as triethylamine.

Alternatively, the reaction may conveniently be effected at an elevated temperature in the presence of a mineral acid, e.g. hydrochloric acid.

Alternatively, the reaction may conveniently be effected at an elevated temperature in the presence of a lower alkanol, e.g. a $C_{1-4}$ alkanol such as methanol.

The compounds of formula (IIIC) above may be prepared by a two-step procedure which comprises (i) reacting a compound of formula $H_2N$-$L^4$ with a compound of formula (IX):

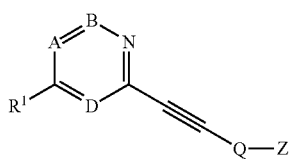

(IX)

wherein A, B, D, Q, Z and R¹ are as defined above, and $L^3$ represents a suitable leaving group; and (ii) treatment with a base.

The leaving group $L^4$ is typically an arylsulphonate moiety, e.g. 2,4,6-trimethyl-benzenesulphonate.

Step (i) is conveniently effected at ambient temperature in a suitable solvent, e.g. a $C_{1-4}$ alkanol such as ethanol.

Step (ii) is conveniently effected at elevated temperature in a suitable solvent, e.g. a $C_{1-4}$ alkanol such as ethanol. The base employed in the reaction will suitably be an inorganic base, e.g. an alkaline earth metal carbonate such as potassium carbonate.

The intermediates of formula (IX) above may be prepared by reacting a compound of formula H—C≡C-Q-Z with a compound of formula (X):

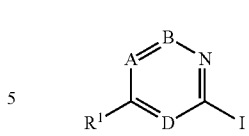

(X)

wherein A, B, D, Q, Z and R¹ are as defined above; in the presence of a transition metal catalyst.

The transition metal catalyst of use in the foregoing reaction is suitably a palladium complex such as [1,1'-bis(diphenylphosphino)ferrocene]dichloropalladium(II). The reaction is conveniently effected at ambient temperature in the presence of a copper(I) salt, e.g. copper(I) iodide, and a base, suitably an organic base such as triethylamine.

Where they are not commercially available, the starting materials of formula (VB), (VI), (VII), (VIII) and (X) may be prepared by methods analogous to those described in the accompanying Examples, or by standard methods well known from the art.

It will be understood that any compound of formula (IA) or (IB) initially obtained from any of the above processes may, where appropriate, subsequently be elaborated into a further compound of formula (IA) or (IB) by techniques known from the art. By way of example, a compound wherein E represents —C(O)— may be converted into the corresponding compound wherein E represents —CH(OH)— by treatment with a reducing agent such as sodium borohydride.

A compound wherein E represents —CH(OH)— may be converted into the corresponding compound wherein E represents —$CH_2$— by heating with elemental iodine and phosphinic acid in acetic acid; or by treating with triethylsilane and an acid, e.g. an organic acid such as trifluoroacetic acid, or a Lewis acid such as boron trifluoride diethyl etherate; or by treating with chlorotrimethylsilane and sodium iodide; or by a two-step procedure which comprises: (i) treatment with thionyl bromide; and (ii) treatment of the product thereby obtained with a transition metal catalyst, e.g. (2,2'-bipyridine)dichloro-ruthenium(II) hydrate, in the presence of diethyl 1,4-dihydro-2,6-dimethyl-3,5-pyridine-dicarboxylate (Hantzsch ester) and a base, e.g. an organic base such as N,N-diisopropylethylamine.

A compound wherein E represents —$CH_2$— may be converted into the corresponding compound wherein E represents —$CH(CH_3)$— by treatment with a methyl halide, e.g. methyl iodide, in the presence of a base such as lithium hexamethyldisilazide.

A compound which contains a hydroxy group may be alkylated by treatment with the appropriate alkyl halide in the presence of a base, e.g. sodium hydride, or silver oxide. A compound wherein -Q-Z represents —$CH_2OH$ may be arylated in a two-step procedure which comprises: (i) treatment with thionyl chloride; and (ii) treatment of the chloro derivative thereby obtained with the appropriate aryl or heteroaryl hydroxide. A compound wherein -Q-Z represents —$CH_2OH$ may be converted into the corresponding compound wherein -Q-Z represents —$CH_2S$—Z via a two-step procedure which comprises: (i) treatment with thionyl chloride; and (ii) treatment of the chloro derivative thereby obtained with a compound of formula Z—SH, typically in the presence of a base, e.g. an inorganic base such as potassium carbonate. A compound wherein -Q-Z represents —$CH_2OH$ may be converted into the corresponding compound wherein -Q-Z represents —$CH_2CN$ via a two-step procedure which comprises: (i) treatment with thionyl chloride; and (ii) treatment of the chloro derivative thereby obtained with a cyanide salt such as sodium cyanide. A compound which contains hydroxy may be converted into the corresponding fluoro-substituted compound by treatment with diethylaminosulfur trifluoride (DAST) or bis(2-methoxyethyl)aminosulfur trifluoride (BAST). A compound which contains hydroxy may be converted into the corresponding difluoro-substituted compound via a two-step procedure which comprises: (i) treatment with an oxidising agent, e.g. manganese dioxide; and (ii) treatment of the carbonyl-containing compound thereby obtained with DAST.

A compound which contains an N—H moiety may be alkylated by treatment with the appropriate alkyl halide, typically at an elevated temperature in an organic solvent such as acetonitrile; or at ambient temperature in the presence of a base, e.g. an alkali metal carbonate such as potassium carbonate or cesium carbonate, in a suitable solvent, e.g. a dipolar aprotic solvent such as N,N-dimethylformamide. Alternatively, a compound which contains an N—H moiety may be alkylated by treatment with the appropriate alkyl tosylate in the presence of a base, e.g. an inorganic base such as sodium hydride, or an organic base such as 1,8-diazabicyclo[5.4.0]undec-7-ene (DBU).

A compound which contains an N—H moiety may be methylated by treatment with formaldehyde in the presence of a reducing agent, e.g. sodium triacetoxyborohydride.

A compound which contains an N—H moiety may be acylated by treatment with the appropriate acid chloride, e.g. acetyl chloride, or with the appropriate carboxylic acid anhydride, e.g. acetic anhydride, typically at ambient temperature in the presence of a base, e.g. an organic base such as triethylamine.

A compound which contains an N—H moiety may be converted into the corresponding compound wherein the nitrogen atom is substituted by $C_{1-6}$ alkylsulphonyl, e.g. methylsulphonyl, by treatment with the appropriate $C_{1-6}$ alkylsulphonyl chloride, e.g. methanesulphonyl chloride, or with the appropriate $C_{1-6}$ alkylsulphonic acid anhydride, e.g. methanesulphonic anhydride, typically at ambient temperature in the presence of a base, e.g. an organic base such as triethylamine or N,N-diisopropylethylamine.

A compound substituted by amino (—$NH_2$) may be converted into the corresponding compound substituted by $C_{1-6}$ alkylsulphonylamino, e.g. methylsulphonylamino, or bis[($C_{1-6}$)alkylsulphonyl]amino, e.g. bis(methylsulphonyl)amino, by treatment with the appropriate $C_{1-6}$ alkylsulphonyl halide, e.g. a $C_{1-6}$ alkylsulphonyl chloride such as methanesulphonyl chloride. Similarly, a compound substituted by hydroxy (—OH) may be converted into the corresponding compound substituted by $C_{1-6}$ alkylsulphonyloxy, e.g. methylsulphonyloxy, by treatment with the appropriate $C_{1-6}$ alkylsulphonyl halide, e.g. a $C_{1-6}$ alkylsulphonyl chloride such as methanesulphonyl chloride.

A compound containing the moiety —S— may be converted into the corresponding compound containing the moiety —S(O)— by treatment with 3-chloroperoxybenzoic acid. Likewise, a compound containing the moiety —S(O)— may be converted into the corresponding compound containing the moiety —$S(O)_2$— by treatment with 3-chloroperoxybenzoic acid. Alternatively, a compound containing the moiety —S— may be converted into the corresponding compound containing the moiety —$S(O)_2$— by treatment with Oxone® (potassium peroxymonosulfate).

A compound containing an aromatic nitrogen atom may be converted into the corresponding N-oxide derivative by treatment with 3-chloroperoxybenzoic acid.

A bromophenyl derivative may be converted into the corresponding optionally substituted 2-oxopyrrolidin-1-ylphenyl or 2-oxooxazolidin-3-ylphenyl derivative by treatment with pyrrolidin-2-one or oxazolidin-2-one, or an appropriately substituted analogue thereof. The reaction is conveniently effected at an elevated temperature in the presence of copper(I) iodide, trans-N,N'-dimethylcyclohexane-1,2-diamine and an inorganic base such as potassium carbonate.

A compound wherein $R^1$ represents halogen, e.g. bromo or iodo, may be converted into the corresponding compound wherein $R^1$ represents an optionally substituted aryl or heteroaryl moiety by treatment with the appropriately substituted aryl or heteroaryl boronic acid or a cyclic ester thereof formed with an organic diol, e.g. pinacol, 1,3-propanediol or neopentyl glycol. The reaction is typically effected in the presence of a transition metal catalyst, e.g. [1,1'-bis(diphenylphosphino)ferrocene]dichloropalladium (II), tetrakis(triphenylphosphine)palladium(0), or bis[3-(diphenylphosphanyl)cyclopenta-2,4-dien-1-yl]iron-dichloropalladium-dichloromethane complex, and a base, e.g. an inorganic base such as sodium carbonate or potassium carbonate, or potassium phosphate.

A compound wherein $R^1$ represents halogen, e.g. bromo, may be converted into the corresponding compound wherein $R^1$ represents an optionally substituted aryl, heteroaryl or heterocycloalkenyl moiety via a two-step procedure which comprises: (i) reaction with bis(pinacolato)diboron or bis (neopentyl glycolato)diboron; and (ii) reaction of the compound thereby obtained with an appropriately functionalised halo- or tosyloxy-substituted aryl, heteroaryl or heterocycloalkenyl derivative. Step (i) is conveniently effected in the presence of a transition metal catalyst such as [1,1'-bis (diphenylphosphino)-ferrocene]dichloropalladium(II), or bis[3-(diphenylphosphanyl)cyclopenta-2,4-dien-1-yl]iron-dichloropalladium-dichloromethane complex. Step (ii) is conveniently effected in the presence of a transition metal catalyst such as tetrakis(triphenylphosphine)-palladium(0), or bis[3-(diphenylphosphanyl)cyclopenta-2,4-dien-1-yl] iron-dichloropalladium-dichloromethane complex, and a base, e.g. an inorganic base such as sodium carbonate or potassium carbonate.

A compound wherein $R^1$ represents halogen, e.g. bromo, may be converted into the corresponding compound wherein $R^1$ represents an optionally substituted $C_{2-6}$ alkynyl moiety by treatment with an appropriately substituted alkyne derivative, e.g. 2-hydroxybut-3-yne. The reaction is conveniently accomplished with the assistance of a transition metal catalyst, e.g. tetrakis(triphenylphosphine)palladium (0), typically in the presence of copper(I) iodide and a base, e.g. an organic base such as triethylamine.

A compound wherein $R^1$ represents halogen, e.g. bromo, may be converted into the corresponding compound wherein $R^1$ represents an optionally substituted imidazol-1-yl moiety by treatment with the appropriately substituted imidazole derivative, typically in the presence of copper(II) acetate and an organic base such as N,N,N',N'-tetramethylethylenediamine (TMEDA).

A compound wherein $R^1$ represents halogen, e.g. bromo, may be converted into the corresponding compound wherein $R^1$ represents 2-(methoxycarbonyl)ethyl via a two-step procedure which comprises: (i) reaction with methyl acrylate; and (ii) catalytic hydrogenation of the alkenyl derivative thereby obtained, typically by treatment with a hydrogenation catalyst, e.g. palladium on charcoal, under an atmosphere of hydrogen gas. Step (i) is typically effected in the presence of a transition metal catalyst, e.g. palladium(II)

acetate or bis(dibenzylideneacetone)palladium(0), and a reagent such as tri(ortho-tolyl)-phosphine.

In general, a compound containing a —C≡C— functionality may be converted into the corresponding compound containing a —CH—CH— functionality by catalytic hydrogenation, typically by treatment with a hydrogenation catalyst, e.g. palladium on charcoal, under an atmosphere of hydrogen gas, optionally in the presence of a base, e.g. an alkali metal hydroxide such as sodium hydroxide.

A compound wherein $R^1$ represents 6-methoxypyridin-3-yl may be converted into the corresponding compound wherein $R^1$ represents 2-oxo-1,2-dihydropyridin-5-yl by treatment with pyridine hydrochloride; or by heating with a mineral acid such as hydrochloric acid. By utilising similar methodology, a compound wherein $R^1$ represents 6-methoxy-4-methylpyridin-3-yl may be converted into the corresponding compound wherein $R^1$ represents 4-methyl-2-oxo-1,2-dihydropyridin-5-yl; and a compound wherein $R^1$ represents 6-methoxy-5-methylpyridin-3-yl may be converted into the corresponding compound wherein $R^1$ represents 3-methyl-2-oxo-1,2-dihydropyridin-5-yl.

A compound wherein $R^1$ represents 2-oxo-1,2-dihydropyridin-5-yl may be converted into the corresponding compound wherein $R^1$ represents 2-oxopiperidin-5-yl by catalytic hydrogenation, typically by treatment with gaseous hydrogen in the presence of a hydrogenation catalyst such as platinum(IV) oxide.

A compound containing an ester moiety, e.g. a $C_{2-6}$ alkoxycarbonyl group such as methoxycarbonyl or ethoxycarbonyl, may be converted into the corresponding compound containing a carboxy (—CO$_2$H) moiety by treatment with an acid, e.g. a mineral acid such as hydrochloric acid.

A compound containing an N-(tert-butoxycarbonyl) moiety may be converted into the corresponding compound containing an N—H moiety by treatment with an acid, e.g. a mineral acid such as hydrochloric acid, or an organic acid such as trifluoroacetic acid.

A compound containing an ester moiety, e.g. a $C_{2-6}$ alkoxycarbonyl group such as methoxycarbonyl or ethoxycarbonyl, may alternatively be converted into the corresponding compound containing a carboxy (—CO$_2$H) moiety by treatment with a base, e.g. an alkali metal hydroxide selected from lithium hydroxide, sodium hydroxide and potassium hydroxide; or an organic base such as sodium methoxide or sodium ethoxide.

A compound containing a carboxy (—CO$_2$H) moiety may be converted into the corresponding compound containing an amide moiety by treatment with the appropriate amine in the presence of a condensing agent such as 1-ethyl-3-(3-dimethylaminopropyl)-carbodiimide.

A compound containing a carbonyl (C═O) moiety may be converted into the corresponding compound containing a —C(CH$_3$)(OH)— moiety by treatment with methylmagnesium bromide. Similarly, a compound containing a carbonyl (C═O) moiety may be converted into the corresponding compound containing a —C(CF$_3$)(OH)— moiety by treatment with (trifluoromethyl)trimethylsilane and cesium fluoride. A compound containing a carbonyl (C═O) moiety may be converted into the corresponding compound containing a —C(CH$_2$NO$_2$)(OH)— moiety by treatment with nitromethane.

A compound containing a hydroxymethyl moiety may be converted into the corresponding compound containing a formyl (—CHO) moiety by treatment with an oxidising agent such as Dess-Martin periodinane. A compound containing a hydroxymethyl moiety may be converted into the corresponding compound containing a carboxy moiety by treatment with an oxidising agent such as tetrapropylammonium perruthenate. Similarly, a compound containing a —CH(OH)— moiety may be converted into the corresponding compound containing a —C(O)— moiety by treatment with an oxidising agent such as tetrapropylammonium perruthenate.

A compound wherein $R^1$ represents a substituent containing at least one nitrogen atom, which substituent is linked to the remainder of the molecule via a nitrogen atom, may be prepared by reacting a compound wherein $R^1$ represents halogen, e.g. bromo, with the appropriate compound of formula $R^1$—H [e.g. 1-(pyridin-3-yl)piperazine or morpholine]. The reaction is conveniently effected with the assistance of a transition metal catalyst, e.g. tris(dibenzylideneacetone)dipalladium(0), in the presence of an amination ligand such as 2-dicyclohexylphosphino-2',4',6'-triisopropylbiphenyl (XPhos) or 2,2'-bis(diphenylphosphino)-1,1'-binaphthalene (BINAP) and a base, e.g. an inorganic base such as sodium tert-butoxide. Alternatively, the reaction may be effected using palladium diacetate, in the presence of a reagent such as [2',6'-bis(propan-2-yloxy)-biphenyl-2-yl](dicyclohexyl)phosphane and a base, e.g. an inorganic base such as cesium carbonate.

A compound containing an oxo moiety can be converted into the corresponding compound containing an ethoxycarbonylmethylidene moiety by treatment with triethyl phosphonoacetate in the presence of a base such as sodium hydride.

A compound wherein $R^{21}$ represents ethenyl may be prepared by reacting a compound wherein $R^{21}$ represents halogen, e.g. chloro, with potassium vinyl trifluoro-borate. The reaction is typically effected in the presence of a transition metal catalyst, e.g. [1,1'-bis(diphenylphosphino)ferrocene]dichloropalladium(II), and a base, e.g. an organic base such as triethylamine.

A compound wherein $R^{21}$ represents halogen, e.g. chloro, may be converted into the corresponding compound wherein $R^{21}$ represents an optionally substituted $C_{4-7}$ cycloalkenyl moiety by treatment with the appropriately substituted cycloalkenyl boronic acid or a cyclic ester thereof formed with an organic diol, e.g. pinacol, 1,3-propanediol or neopentyl glycol. The reaction is typically effected in the presence of a transition metal catalyst, e.g. bis[3-(diphenylphosphanyl)cyclopenta-2,4-dien-1-yl]iron-dichloropalladium-dichloromethane complex, and a base, e.g. an inorganic base such as potassium carbonate.

A compound wherein $R^{21}$ represents a substituent containing at least one nitrogen atom, which substituent is linked to the remainder of the molecule via a nitrogen atom, may be prepared by reacting a compound wherein $R^{21}$ represents halogen, e.g. chloro, with the appropriate compound of formula $R^{21}$—H [e.g. 2-methoxyethylamine, N-methyl-L-alanine, 2-aminocyclopentanecarboxylic acid, 3-aminocyclopentanecarboxylic acid, 1-(aminomethyl)cyclopropanecarboxylic acid, methyl azetidine-3-carboxylate, pyrrolidin-3-ol, pyrrolidine-3-carboxylic acid, piperidine-2-carboxylic acid, piperidine-3-carboxylic acid, 4-(1H-tetrazol-5-yl)piperidine, piperazine, 1-(methylsulfonyl)piperazine, piperazin-2-one, 2-(piperazin-1-yl)propanoic acid, morpholine, morpholine-2-carboxylic acid, thiomorpholine, thiomorpholine 1,1-dioxide, 1,4-diazepan-5-one, 2-oxa-5-azabicyclo-[2.2.1]heptane or an appropriately substituted azaspiroalkane], optionally in the presence of a base, e.g. an organic base such as triethylamine or N,N-diisopropylethylamine and/or 1-methyl-2-pyrrolidinone, or pyridine, or an inorganic base such as potassium carbonate.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (IA) or (IB) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (IA) or (IB), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (IA) or (IB) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

The following Examples illustrate the preparation of compounds according to the invention.

The compounds in accordance with this invention potently inhibit the binding of a fluorescence conjugate to TNFα when tested in the fluorescence polarisation assay described below. Moreover, certain compounds in accordance with this invention potently inhibit TNFα-induced NF-κB activation in the reporter gene assay described below.

Fluorescence Polarisation Assay
Preparation of Compound (A)

1-(2,5-Dimethylbenzyl)-6-[4-(piperazin-1-ylmethyl)phenyl]-2-(pyridin-4-ylmethyl)-1H-benzimidazole—hereinafter referred to as "Compound (A)"—can be prepared by the procedure described in Example 499 of WO 2013/186229 (published 19 Dec. 2013); or by a procedure analogous thereto.

Preparation of Fluorescence Conjugate

Compound (A) (27.02 mg, 0.0538 mmol) was dissolved in DMSO (2 mL). 5 (-6) Carboxy-fluorescein succinimyl ester (24.16 mg, 0.0510 mmol) (Invitrogen catalogue number: C1311) was dissolved in DMSO (1 mL) to give a bright yellow solution. The two solutions were mixed at room temperature, the mixture turning red in colour. The mixture was stirred at room temperature. Shortly after mixing a 20 µL aliquot was removed and diluted in a 80:20 mixture of AcOH:H$_2$O for LC-MS analysis on the 1200RR-6140 LC-MS system. The chromatogram showed two closely eluting peaks at retention times of 1.42 and 1.50 minutes, both with mass (M+H)$^+$=860.8 amu, corresponding to the two products formed with the 5- and 6-substituted carboxyfluorescein group. A further peak at retention time 2.21 minutes had a mass of (M+H)$^+$=502.8 amu, corresponding to Compound (A). No peak was observed for unreacted 5(-6) carboxyfluorescein succinimyl ester. The peak areas were 22.0%, 39.6% and 31.4% for the three signals, indicating a 61.6% conversion to the two isomers of the desired fluorescence conjugate at that time-point. Further 20 µL aliquots were extracted after several hours and then after overnight stirring, diluted as before and subjected to LC-MS analysis. The percentage conversion was determined as 79.8% and 88.6% respectively at these time-points. The mixture was purified on a UV-directed preparative HPLC system. The pooled purified fractions were freeze-dried to remove excess solvent. After freeze-drying, an orange solid (23.3 mg) was recovered, equivalent to 0.027 mmol of fluorescence conjugate, corresponding to an overall yield of 53% for the reaction and preparative HPLC purification.

Inhibition of Binding of Fluorescence Conjugate to TNFα

Compounds were tested at 10 concentrations starting from 25 µM in a final assay concentration of 5% DMSO, by pre-incubation with TNFα for 60 minutes at ambient temperature in 20 mM Tris, 150 mM NaCl, 0.05% Tween 20, before addition of the fluorescence conjugate and a further incubation for 20 hours at ambient temperature. The final concentrations of TNFα and the fluorescence conjugate were 10 nM and 10 nM respectively in a total assay volume of 25 µL. Plates were read on a plate reader capable of detecting fluorescence polarisation (e.g. an Analyst HT plate reader; or an Envision plate reader). An IC$_{50}$ value was calculated using XLfit™ (4 parameter logistic model) in ActivityBase.

When tested in the fluorescence polarisation assay, the compounds of the accompanying Examples were all found to exhibit IC$_{50}$ values of 50 µM or better.

Reporter Gene Assay
Inhibition of TNFα-Induced NF-κB Activation

Stimulation of HEK-293 cells by TNFα leads to activation of the NF-κB pathway. The reporter cell line used to determine TNFα activity was purchased from InvivoGen. HEK-Blue™ CD40L is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a dose-dependent manner by TNFα, with an EC50 of 0.5 ng/mL for human TNFα. Compounds were diluted from 10 mM DMSO stocks (final assay concentration 0.3% DMSO) to generate a 10-point 3-fold serial dilution curve (e.g. 30,000 nM to 2 nM final concentration). Diluted compound was preincubated with TNFα for 60 minutes prior to addition to a 384-well microtitre plate and incubated for 18 h. The final TNFα concentration in the assay plate was 0.5 ng/mL. SEAP activity was determined in the supernatant using a colorimetric substrate, e.g. QUANTI-Blue™ or HEK-Blue™ Detection media (InvivoGen). Percentage inhibitions for compound dilutions were calculated between a DMSO control and maximum inhibition (by excess control compound)

and an IC$_{50}$ value calculated using XLfit™ (4 parameter logistic model) in ActivityBase.

When tested in the reporter gene assay, certain compounds of the accompanying Examples were found to exhibit IC$_{50}$ values of 50 μM or better.

EXAMPLES

Abbreviations

DCM: dichloromethane EtOAc: ethyl acetate
MeOH: methanol DMSO: dimethylsulfoxide
EtOH: ethanol Et$_2$O: diethyl ether
DMF: N,N-dimethylformamide MeCN: acetonitrile
TBAF: tetrabutylammonium fluoride THF: tetrahydrofuran
DIPEA: N,N-diisopropylethylamine IPA: isopropyl alcohol
NMP: 1-methyl-2-pyrrolidinone TPAP: tetrapropylammonium perruthenate
TFA: trifluoroacetic acid
TMEDA: N,N,N',N'-tetramethylethylenediamine
Pd(PPh$_3$)$_4$: tetrakis(triphenylphosphine)palladium(0)
Pd(dppf)Cl$_2$: [1,1'-bis(diphenylphosphino)ferrocene]dichloropalladium(II)
h: hour M: mass
HPLC: High Performance Liquid Chromatography
LCMS: Liquid Chromatography Mass Spectrometry
RT: retention time
Nomenclature Compounds were named with the aid of ACD/Name Batch (Network) version 12.0, and/or Accelrys Draw 4.0.
Analytical Conditions
NMR NMR spectra were obtained using a Bruker DPX 250 MHz NMR spectrometer; a Bruker Fourier 300 MHz NMR spectrometer; a Bruker AVIII 400 MHz NMR spectrometer; a Bruker DRX 500 MHz NMR spectrometer; or an AV 600 MHz NMR spectrometer. Chemical shift values are reported in ppm (δ) with zero corresponding to the corrected residual deuterated solvent shift as an internal reference, or with zero corresponding to tetramethylsilane as an internal standard. The NMR spectra were recorded at a temperature ranging from 5 to 110° C. When more than one conformer was detected the chemical shifts for the most abundant conformer are reported.
LCMS LCMS data were obtained using the method described below, or an analogous method. Mass spectra were generated by using ESI ionisation.
Column: Waters, X-Bridge, 20×2.1 mm, 2.5 μm
pH: high (approximately pH 9.5)
Mobile Phase A: 10 mM ammonium formate in water+0.1% ammonia
Mobile Phase B: acetonitrile+5% solvent A+0.1% ammonia
Injection Volume: 5.0 μL
Flow Rate: 1.00 mL/minute
Column temperature: 40° C.
Gradient program:

| Time | A % | B % |
|---|---|---|
| 0.00 | 95.0 | 5.0 |
| 1.50 | 5.0 | 95.0 |
| 2.25 | 5.0 | 95.0 |
| 2.30 | 95.0 | 5.0 |

Intermediate 1

6-Bromo-7-fluoro-2-methylimidazo[1,2-a]pyridine

5-Bromo-4-fluoropyridin-2-amine (5 g, 26.18 mmol) was dissolved in EtOH (50 mL) and 1-chloropropan-2-one (4.25 mL, 52.82 mmol) was added. The reaction mixture was stirred at reflux overnight, then further 1-chloropropan-2-one (2.5 mL, 31.1 mmol) was added and the reaction mixture was heated for a further 4 h at 90° C. The reaction mixture was concentrated to dryness and re-dissolved in EtOAc (15 mL), then washed with saturated aqueous NaHCO$_3$ solution (10 mL) and brine (10 mL). The aqueous layer was re-extracted with EtOAc (2×10 mL), then the combined organic layers were washed with brine (10 mL), dried over Na$_2$SO$_4$ and concentrated to dryness under vacuum. The resulting crude orange solid was purified by chromatography on silica gel, eluting with 0-100% EtOAc in isohexane, to afford the title compound (1.18 g, 19.7%) as a white solid. δ$_H$ (500 MHz, DMSO-d$_6$) 8.97 (d, J7.0 Hz, 1H), 7.62 (s, 1H), 7.51 (d, J9.8 Hz, 1H), 2.30 (s, 3H).
Alternative Procedure A suspension of 5-bromo-4-fluoropyridin-2-amine (1 g, 5.24 mmol) in IPA (10 mL) was treated with 1-bromo-2,2-dimethoxypropane (1.16 g, 6.28 mmol) and the resulting mixture was heated at 80° C. for 21 h. The reaction mixture was cooled to room temperature, then concentrated under vacuum at 40° C. The residue was treated with EtOAc (15 mL) and water (15 mL), then the phases were separated. The aqueous phase was basified with aqueous NaOH solution (32% w/w) to pH 8, then extracted with EtOAc (10 mL, then 15 mL). The organic phases were pooled and concentrated under vacuum at 40° C. to give the title compound (0.93 g, 78%) as a beige solid.

Intermediate 2

3H-Spiro[2-benzofuran-1,1'-cyclopropane]-3-ol

1-Phenylcyclopropan-1-ol (1.4 g, 10.43 mmol) was dissolved in heptane (14 mL) and TMEDA (4 mL, 26.68 mmol) was added. The mixture was cooled to 0° C. under nitrogen and 2.5M butyllithium in hexane (10 mL) was added over 10 minutes with stirring. The reaction mixture was stirred at 0° C. under nitrogen for 15 minutes, then allowed to warm to ambient temperature and stirred under nitrogen overnight. The reaction mixture was warmed to 40° C. in a water bath for 5 minutes, then cooled to ambient temperature and DMF (2 mL, 25.83 mmol) was added over 5 minutes. The resulting reaction mixture was stirred under nitrogen for 1 h, then quenched carefully with water (15 mL). The organic layer was separated, then the aqueous layer was re-extracted with EtOAc (3×20 mL). The combined organic layers were concentrated to dryness under vacuum. The residue was purified by chromatography on silica gel, eluting with 0-100% EtOAc in heptane, to afford the title compound (864 mg, 54.7%) as a colourless oil. δ$_H$ (500 MHz, DMSO-d$_6$) 7.34-7.31 (m, 2H), 7.31-7.27 (m, 1H), 6.95 (d, J7.0 Hz, 1H), 6.88 (d, J7.6 Hz, 1H), 6.41 (d, J7.5 Hz, 1H), 1.26-1.20 (m, 2H), 1.04-0.94 (m, 2H).

Intermediate 3

6-Bromo-7-fluoro-2-methyl-3-{3H-spiro[2-benzofuran-1,1'-cyclopropane]-3-yl}imidazo-[1,2-a]pyridine Intermediate 1 (90 mg, 0.26 mmol), Intermediate 2 (80%, 140 mg, 0.69 mmol) and pyridinium p-toluenesulfonate (450 mg, 1.79 mmol) were dissolved in MeCN (400 μL) and heated at 90° C. under microwave irradiation for 30 minutes. A second aliquot of Intermediate 1 (60 mg, 0.39 mmol), Intermediate 2 (80%, 90 mg, 0.44 mmol) and pyridinium p-toluenesulfonate (300 mg, 1.19 mmol) in MeCN (300 μL) was heated at 90° C. under microwave irradiation for 30 minutes. The two reaction mixtures were concentrated to dryness under vacuum and re-dissolved in EtOAc (2 mL each), then combined and washed with saturated aqueous NaHCO$_3$ solution (2 mL). The aqueous layer was re-extracted with EtOAc (2×3 mL), then the combined organic layers were dried over Na$_2$SO$_4$ and concentrated to dryness under vacuum. The crude residue (320 mg) was purified by chromatography on silica gel, eluting with 0-75% EtOAc in heptane, to afford the title compound (160 mg, 65.5%) as a pale yellow gum. $\delta_H$ (500 MHz, CDCl$_3$) 7.88 (d, J6.6 Hz, 1H), 7.37 (t, J7.5 Hz, 1H), 7.26-7.22 (m, 2H), 6.95 (d, J7.6 Hz, 1H), 6.93 (d, J7.6 Hz, 1H), 6.76 (s, 1H), 2.52 (s, 3H), 1.50 (ddd, J 11.6, 7.4, 5.6 Hz, 1H), 1.41 (ddd, J 11.4, 7.4, 5.9 Hz, 1H), 1.24 (ddd, J 11.0, 7.3, 5.9 Hz, 1H), 1.06 (ddd, J 10.8, 5.5, 2.0 Hz, 1H). LCMS m/z 372.80 [M+H]$^+$.

Intermediate 4

(3R)-3-Methyl-1,3-dihydro-2-benzofuran-1-ol (1R)-1-Phenylethanol (5.2 g, 42.57 mmol) was dissolved in heptane (50 mL) and TMEDA (14 mL, 93.37 mmol) was added. The mixture was cooled to 0° C. under nitrogen and 2.5M butyllithium in hexane (36 mL) was added over 15 minutes. The reaction mixture was stirred at 0° C. under nitrogen for 15 minutes, then allowed to warm to ambient temperature and stirred under nitrogen overnight. The reaction mixture was warmed to 40° C. in a water bath for 2 minutes, then allowed to cool to ambient temperature and DMF (7 mL, 90.4 mmol) was added over 15 minutes. The resulting reaction mixture was stirred under nitrogen for 2 h, then quenched carefully with water (50 mL). The organic layer was separated, then the aqueous layer was re-extracted with heptane (3×50 mL). The combined organic layers were washed with brine, dried over Na$_2$SO$_4$ and concentrated to dryness, to yield 2 g of crude material. The aqueous layer was re-extracted with EtOAc (2×50 mL), then dried over Na$_2$SO$_4$ and concentrated to dryness under vacuum. The combined residue was triturated with heptane to yield the title compound (3.5 g, 57.6%) as a pale yellow solid. $\delta_H$ (500 MHz, DMSO-d$_6$) 7.43-7.20 (m, 4H), 6.58 (d, J7.2 Hz, 1H), 6.29 (d, J5.5 Hz, 1H), 5.31 (q, J5.7, 5.2 Hz, 1H), 1.37 (d, J 6.4 Hz, 3H).

Intermediate 5

6-Bromo-7-fluoro-2-methyl-3-[(3R)-3-methyl-1,3-dihydro-2-benzofuran-1-yl]imidazo-[1,2-a]pyridine Prepared from Intermediate 1 and Intermediate 4 by a method analogous to that used to prepare Intermediate 3, to afford the title compound (146.3 mg, 46.4%) as a brown gum. $\delta_H$ (500 MHz, CD$_3$OD) 7.90 (dd, J 13.9, 6.6 Hz, 2H), 7.47-7.39 (m, 4H), 7.31 (dt, J 11.0, 8.2 Hz, 4H), 7.03 (d, J7.6 Hz, 1H), 6.92 (d, J7.6 Hz, 1H), 6.80 (d, J2.1 Hz, 1H), 6.64-6.61 (m, 1H), 5.57 (qd, J6.3, 2.3 Hz, 1H), 5.38 (dd, J6.3, 2.3 Hz, 1H), 2.40 (s, 3H), 2.29 (s, 3H), 1.65 (d, J6.4 Hz, 3H), 1.56 (d, J6.4 Hz, 3H). Isomer B: 7.43-7.20 (m, 4H), 6.68 (d, J7.8 Hz, 1H), 6.24 (d, J7.5 Hz, 1H), 5.10 (q, J6.4 Hz, 1H), 1.45 (d, J 6.4 Hz, 3H).

Intermediate 6 tert-Butyl(cyclopent-3-en-1-yloxy)dimethylsilane

Cyclopent-3-en-1-ol (24.7 g, 293.6 mmol) was dissolved in DMF (250 mL) at 0° C., then 1H-imidazole (44 g, 646 mmol) was added, followed by tert-butyl(chloro)-dimethylsilane (53.1 g, 352.4 mmol). The mixture was warmed to room temperature and stirred for 24 h. The mixture was diluted with ethyl acetate (500 mL), washed with 5% w/w aqueous LiCl solution (2×200 mL) and brine (200 mL), then dried over sodium sulfate, filtered, and concentrated. The crude residue was purified by chromatography on silica gel, eluting with 0-20% EtOAc in heptanes, to afford the title compound (57.4 g, 78.8%) as a colourless liquid. $\delta_H$ (500 MHz, CDCl$_3$) 5.66 (s, 2H), 4.53 (tt, J7.0, 3.6 Hz, 1H), 2.57 (dd, J 15.2, 6.8 Hz, 2H), 2.27 (dd, J 15.3, 3.6 Hz, 2H), 0.89 (s, 9H), 0.06 (s, 6H).

Intermediate 7

Ethyl 3-[(tert-butyldimethylsilyl)oxy]bicyclo[3.1.0]hexane-6-carboxylate

Rhodium(II) diacetate (990 mg, 2.24 mmol) was added to a stirred solution of Intermediate 6 (80%, 55.55 g, 224 mmol) in DCM (1160 mL). The mixture was degassed with nitrogen gas for 30 minutes. Under a nitrogen atmosphere, 1-(2-ethoxy-2-oxoethylidene)diazenium (85%, 33.7 mL, 268.82 mmol) was added dropwise over 9 h at room temperature using a syringe pump. The reaction mixture was allowed to stir at room temperature for a further 12 h, then filtered through a pad of Keiselguhr. The Keiselguhr 'cake' was washed with additional DCM and the combined filtrates were concentrated under vacuum The resulting yellow-green oil was purified by chromatography on silica gel, eluting with 0-10% EtOAc in heptanes, to afford the title compound (33.5 g, 53%) as a colourless liquid, as a 4:1 mixture of exo:endo isomers. $\delta_H$ (500 MHz, CDCl$_3$) 4.17-4.02 (m, 2H), 2.14 (dd, J 12.7, 7.2 Hz, 1H), 2.03 (ddd, J 15.8, 6.9, 3.4 Hz, 1H), 1.93-1.66 (m, 4H), 1.58 (s, 1H), 1.26 (qd, J7.2, 2.7 Hz, 4H), 0.86 (t, J 3.5 Hz, 9H), 0.01 (dd, J4.4, 1.2 Hz, 6H).

Intermediate 8

Ethyl 3-hydroxybicyclo[3.1.0]hexane-6-carboxylate

TBAF (1M in THF, 236 mL) was added dropwise to a stirred solution of Intermediate 7 (33.5 g, 117.76 mmol) in THF (400 mL) at 0° C. over 45 minutes, then the mixture was heated at 50° C. for 1 h. The mixture was cooled to room temperature and concentrated under reduced pressure. The residue was diluted with ethyl acetate (300 mL), washed with water (2×250 mL) and brine (2×250 mL), then dried over Na$_2$SO$_4$ and concentrated under reduced pressure, to provide the title compound (18.36 g, 69%) as an orange oil. $\delta_H$ (250 MHz, CDCl$_3$) 4.19-4.01 (m, 2H), 2.26 (dd, J 13.0, 7.1 Hz, 1H), 2.19-2.08 (m, 1H), 1.94-1.70 (m, 4H), 1.52 (s, 2H), 1.30-1.18 (m, 3H).

Intermediate 9

Exo-Ethyl (1R,5S,6S)-3-oxobicyclo[3.1.0]hexane-6-carboxylate

To Intermediate 8 (75%, 18.36 g, 80.9 mmol; and 60%, 5.4 g, 19 mmol) in DCM (450 mL) under a nitrogen atmosphere at 0° C. was added Dess-Martin periodinane (50.9 g, 120.1 mmol) portionwise over 1 h. The reaction mixture was allowed to warm to room temperature and stirred for 22 h, then diluted with DCM (600 mL). The white precipitate was filtered and washed with additional DCM. Following filtration, the yellow solution was washed with saturated aqueous sodium bicarbonate solution (4×200 mL), water (4×200 mL) and brine (3×200 mL), then dried over $Na_2SO_4$ and concentrated under vacuum. The resulting off white solid was purified by chromatography on silica (eluting with 0-50% EtOAc in heptane) to afford the title compound (12.5 g, 74%). $\delta_H$ (500 MHz, $CDCl_3$) (exo-isomer) 4.13 (q, J7.1 Hz, 2H), 2.66 (ddt, J 18.5, 3.9, 1.6 Hz, 2H), 2.31 (d, J 1.8 Hz, 1H), 2.27 (d, J 1.7 Hz, 2H), 2.18 (td, J3.4, 1.6 Hz, 2H), 1.31-1.23 (m, 4H).

Intermediate 10

Ethyl (1S,5S,6R)-3-(trifluoromethanesulfonyloxy)bicyclo[3.1.0]hex-2-ene-6-carboxylate Intermediate 9 (12 g, 71.4 mmol) was dissolved in dry toluene (240 mL), then DIPEA (50 mL, 285.4 mmol) was added and the reaction mixture was heated at 45° C. Trifluoromethanesulfonic anhydride (48 mL, 285.4 mmol) was added dropwise with stirring over 45 minutes, ensuring the internal reaction temperature did not rise above 50° C. The mixture was stirred for a further 2 h at 45° C. The reaction mixture was cooled to room temperature, then diluted with ethyl acetate (750 mL) and washed with saturated aqueous sodium bicarbonate solution (6×250 mL). The combined aqueous layers were extracted with ethyl acetate (6×150 mL) and the combined organic layers were dried over sodium sulfate and concentrated under vacuum. The dark brown residue (~60 g) was purified by chromatography on silica gel, eluting with 0-20% ethyl acetate in heptane, to afford the title compound (10.74 g, 50%) as a dark orange liquid. $\delta_H$ (250 MHz, $CDCl_3$) 5.87 (d, J 1.7 Hz, 1H), 4.13 (q, J7.1 Hz, 2H), 3.38 (q, J7.1 Hz, 1H), 2.99 (ddd, J 18.1, 7.1, 1.9 Hz, 1H), 2.67 (d, J 18.4 Hz, 1H), 2.38 (dq, J7.2, 2.4 Hz, 1H), 2.16 (td, J7.1, 3.3 Hz, 1H), 1.31-1.19 (m, 3H).

Intermediate 11

Ethyl (1S,5S,6R)-3-(4,4,5,5-tetramethyl-1,3,2-dioxaborolan-2-yl)bicyclo[3.1.0]hex-2-ene-6-carboxylate Intermediate 10 (10.74 g, 35.8 mmol) was dissolved in 1,4-dioxane (240 mL) and degassed using nitrogen for 30 minutes. Bis(pinacolato)diborane (13.6 g, 53.70 mmol), potassium acetate (10.5 g, 107.30 mmol), 1,1'-bis(diphenylphosphanyl)ferrocene (0.59 g, 1.10 mmol) and Pd(dppf)Cl$_2$ complex with DCM (0.88 g, 1.10 mmol) were added, and the reaction mixture was heated under nitrogen at 90° C. for 18 h. The reaction mixture was cooled to room temperature, diluted with ethyl acetate (600 mL) and washed with a saturated aqueous solution of sodium bicarbonate (4×200 mL). The combined aqueous washes were re-extracted with ethyl acetate (2×200 mL). The combined organic extracts were washed with brine (2×200 mL), dried over sodium sulfate and concentrated. The crude residue (~40 g) was purified by chromatography on silica (eluting with 0-15% ethyl acetate in heptanes) to afford the title compound (10 g, 50%) as a yellow solid. $\delta_H$ (250 MHz, $CDCl_3$) 6.66 (d, J2.0 Hz, 1H), 4.10 (q, J7.1 Hz, 2H), 2.88-2.71 (m, 1H), 2.61 (t, J 2.0 Hz, 1H), 2.50 (ddt, J 8.0, 4.3, 1.7 Hz, 1H), 2.26 (ddd, J 9.3, 3.6, 1.7 Hz, 1H), 1.33-1.15 (m, 16H).

Intermediate 12

6-Bromo-2-methylimidazo[1,2-a]pyridine

A solution of 5-bromopyridin-2-amine (20 g, 115.6 mmol) in ethanol (200 mL) was treated with 1-chloropropan-2-one (18.6 mL, 231.2 mmol), added portionwise, and the reaction mixture was stirred under reflux for 16 h. The reaction mixture was concentrated under vacuum. The resulting yellow solid was re-dissolved in DCM (150 mL) and 1M aqueous sodium hydroxide solution (150 mL) was added. The two-phase mixture was stirred at ambient temperature for 20 minutes. The organic phase was separated and washed with brine (50 mL), then dried over $Na_2SO_4$ and concentrated to dryness under vacuum. The crude residue was purified by chromatography on silica gel (eluting with 0-100% EtOAc in heptane) to afford the title compound (13.75 g, 53.4%) as a white solid. $\delta_H$ (250 MHz, $CDCl_3$) 8.18 (s, 1H), 7.41 (d, J9.5 Hz, 1H), 7.30 (s, 1H), 7.18 (d, J9.5 Hz, 1H), 2.44 (s, 3H). LCMS m/z 211/213 [M+H]+.

Intermediate 13

(3S)—N,N,3-Trimethyl-1,3-dihydro-2-benzofuran-1-amine (1S)-1-Phenylethanol (5.32 mL, 44.04 mmol) was dissolved in heptane (50 mL) and TMEDA (14 mL, 93.37 mmol) was added. The mixture was cooled to 0° C. under nitrogen and 2.5M butyllithium in hexanes (37 mL) was added over 15 minutes. The reaction mixture was stirred at 0° C. under nitrogen for 15 minutes, then allowed to warm to ambient temperature and stirred under nitrogen overnight. The reaction mixture was warmed to 40° C. in a water bath for 2 minutes, then allowed to cool to ambient temperature and DMF (7 mL, 90.4 mmol) was added over 15 minutes. The resulting reaction mixture was stirred under nitrogen for 3 h, then quenched carefully with water (50 mL) and extracted with EtOAc (3×75 mL). The combined organic layers were washed with brine, dried over $Na_2SO_4$ and concentrated under vacuum to dryness. The residue was purified by chromatography on silica (eluting with 0 to 40% EtOAc in heptane) to afford the title compound (3.5 g, 26.5%) as a colourless oil. $\delta_H$ (500 MHz, DMSO-d$_6$) (isomer A): 7.38-7.17 (m, 4H), 5.88 (s, 1H), 5.12-5.07 (m, 1H), 2.19 (s, 6H), 1.39 (d, J6.4 Hz, 3H); (isomer B): 7.38-7.17 (m, 4H), 5.90 (d, J2.9 Hz, 1H), 5.21 (qd, J 6.4, 2.9 Hz, 1H), 2.16 (s, 6H), 1.37 (d, J6.4 Hz, 3H). LCMS m/z 178.4 [M+H]$^+$.

Intermediate 14

6-Bromo-2-methyl-3-[(1S,3S)-3-methyl-1,3-dihydro-2-benzofuran-1-yl]imidazo[1,2-a]-pyridine Intermediate 12 (0.9 g, 4.26 mmol) and Intermediate 13 (2.5 g, 9.87 mmol) were dissolved in MeCN (8 mL) and pyridinium p-toluenesulfonate (4.3 g, 17.11 mmol) was added. The reaction mixture was allowed to stir for 90 minutes at 100° C. under microwave irradiation. Intermediate 13 (1.5 g, 5.92 mmol) and pyridinium p-toluenesulfonate (2 g, 7.96 mmol) were added and the reaction mixture was stirred for 60 minutes at 100° C. under microwave irradiation. Intermediate 13 (1 g, 3.95 mmol) was added and the reaction mixture was stirred for 60 minutes at 100° C. under microwave irradiation. The reaction mixture was combined with repeated reactions. The combined reaction mixtures were concentrated under vacuum. The residue was purified by chromatography on silica gel, eluting with a gradient of 0-100% ethyl acetate in heptanes. The resulting crude dark brown oil (5.2 g) was dissolved to 100 mg/mL and purified by HPLC (using a Lux Cellulose-4, 21.2×250 mm, 5 µm column; eluting with heptane/IPA in a 70/30 ratio; no modifier added; flow rate 21 mL/minute). The wet fractions were evaporated to dryness under vacuum to afford the title compound (2.36 g, 40.2%). $\delta_H$ (500 MHz, CD$_3$OD) 7.81 (s, 1H), 7.44 (t, J8.9 Hz, 3H), 7.36 (dd, J9.5, 1.8 Hz, 1H), 7.31 (t, J7.0 Hz, 1H), 6.92 (d, J7.6 Hz, 1H), 6.66 (d, J2.7 Hz, 1H), 5.41 (qd, J6.3, 2.8 Hz, 1H), 2.44 (s, 3H), 1.66 (d, J6.4 Hz, 3H).

Intermediate 15

2-Chloro-5-{2-methyl-3-[(1S,3S)-3-methyl-1,3-dihydro-2-benzofuran-1-yl]imidazo[1,2-a]pyridin-6-yl}pyrimidine Intermediate 14 (94%, 800 mg, 2.19 mmol) and 2-chloro-5-(4,4,5,5-tetramethyl-1,3,2-dioxaborolan-2-yl)pyrimidine (1.1 g, 4.57 mmol) were dissolved in 1,4-dioxane (25 mL) and DMSO (7 mL), then degassed with nitrogen for 10 minutes. Bis(triphenyl-phosphine)palladium(II) dichloride (80 mg, 0.11 mmol) and tri-tert-butylphosphonium tetrafluoroborate (65 mg, 0.22 mmol) were added and the reaction mixture was heated at 120° C. under nitrogen for 3 h. The reaction mixture was diluted with EtOAc (80 mL), then washed with water (40 mL) and brine (30 mL). The combined aqueous layers were re-extracted with EtOAc (50 mL) and the resulting organic layer was washed with brine (20 mL). The combined organic layers were dried over Na$_2$SO$_4$ and concentrated to dryness under vacuum. The residue was purified by chromatography on silica (eluting with 0 to 60% EtOAc in heptane) to yield the title compound (457 mg, 55.3%) as a pale yellow solid. $\delta_H$ (500 MHz, CDCl$_3$) 8.45 (s, 2H), 7.80 (d, J 8.5 Hz, 1H), 7.69 (s, 1H), 7.45 (t, J7.6 Hz, 1H), 7.40-7.32 (m, 2H), 7.29 (t, J7.4 Hz, 1H), 6.90 (d, J7.6 Hz, 1H), 6.61 (d, J2.7 Hz, 1H), 5.42 (qd, J6.2, 3.2 Hz, 1H), 2.64 (s, 3H), 1.65 (d, J6.3 Hz, 3H). LCMS m/z 377.1 [M+H]$^+$.

Intermediate 16

Ethyl (1S,5S,6R)-3-(5-{2-methyl-3-[(1S,3S)-3-methyl-1,3-dihydro-2-benzofuran-1-yl]-imidazo[1,2-a]pyridin-6-yl}pyrimidin-2-yl)bicyclo[3.1.0]hex-2-ene-6-carboxylate Intermediate 15 (50 mg, 0.13 mmol) and Intermediate 11 (75%, 55 mg, 0.15 mmol) were dissolved in 1,4-dioxane (1 mL). A 2M solution of potassium carbonate in water (200 µL) was added and the mixture was degassed with nitrogen for 10 minutes. Pd(PPh$_3$)$_4$ (15 mg, 0.01 mmol) was added and the reaction mixture was heated at 120° C. under microwave irradiation for 2 h with stirring. The reaction was repeated on a 407 mg scale (2 batches of 203.5 mg), with heating at 120° C. under microwave irradiation for 2 h with stirring. The reaction mixtures were combined and diluted with EtOAc (50 mL), then washed with water (15 mL) and brine (15 mL). The combined aqueous layers were re-extracted with EtOAc (30 mL), then the resulting organic layer was washed with brine (10 mL). The combined organic layers were dried over Na$_2$SO$_4$ and concentrated to dryness under vacuum. The crude residue (1.1 g) was purified by chromatography on silica (eluting with 15-50% EtOAc in heptane). The resulting crude material (740 mg) was further purified by preparative HPLC to afford the title compound (55.7 mg+69.5 mg, 10.5%+12.4%) as a light brown solid. $\delta_H$ (500 MHz, CD$_3$OD) 8.63 (d, J29.9 Hz, 2H), 7.88 (s, 1H), 7.67-7.58 (m, 2H), 7.47 (d, J6.5 Hz, 2H), 7.36-7.30 (m, 1H), 7.14 (d, J 1.9 Hz, 1H), 6.96 (d, J7.6 Hz, 1H), 6.76 (d, J2.7 Hz, 1H), 5.43 (dd, J6.3, 2.6 Hz, 1H), 4.14 (q, J7.1 Hz, 2H), 3.17 (dd, J 18.5, 6.6 Hz, 1H), 3.01 (d, J 18.5 Hz, 1H), 2.59 (dd, J 6.1, 2.5 Hz, 1H), 2.46 (s, 3H), 2.37 (td, J6.7, 3.3 Hz, 1H), 1.64 (d, J6.3 Hz, 3H), 1.26 (t, J7.1 Hz, 3H).

Intermediate 17

Ethyl (1R,5S,6R)-3-(5-{2-methyl-3-[(1S,3S)-3-methyl-1,3-dihydro-2-benzofuran-1-yl]-imidazo[1,2-a]pyridin-6-yl}pyrimidin-2-yl)bicyclo[3.1.0]hexane-6-carboxylate Intermediate 16 (95%, 70 mg, 0.13 mmol) and triethylamine (0.022 mL, 0.16 mmol) were dissolved in ethyl acetate (5 mL) and degassed with N$_2$. The mixture was added to palladium on carbon (10%, 25 mg, 0.02 mmol), degassed with N$_2$ and allowed to stir under a hydrogen balloon at ambient temperature for 24 h. The reaction mixture was filtered over a Celite pad which was washed with ethyl acetate (250 mL). The filtrate was concentrated under vacuum to afford the title compound (92 mg, 78.1%) as a yellow-brown solid. $\delta_H$ (500 MHz, CD$_3$OD) 8.64 (s, 2H), 7.93 (s, 1H), 7.61 (d, J 8.7 Hz, 2H), 7.46 (d, J7.3 Hz, 2H), 7.32 (t, J7.1 Hz, 1H), 6.96 (d, J7.5 Hz, 1H), 6.75 (s, 1H), 5.46-5.39 (m, 1H), 4.04 (q, J7.1 Hz, 2H), 3.73 (tt, J8.9, 4.1 Hz, 1H), 2.48 (d, J8.9 Hz, 4H), 2.43 (s, 3H), 1.92 (s, 2H), 1.63 (d, J6.3 Hz, 3H), 1.52 (t, J2.9 Hz, 1H), 1.20 (t, J7.1 Hz, 3H).

Intermediate 18

(3R)—N,N,3-Trimethyl-1,3-dihydro-2-benzofuran-1-amine

Prepared from (1R)-1-phenylethanol and DMF by a method analogous to that used to prepare Intermediate 13, to afford the title compound (490 mg, 27%) as an orange-brown oil. LCMS m/z 178.2 [M+H]+.

Intermediate 19

6-Bromo-2-methyl-3-[(3R)-3-methyl-1,3-dihydro-2-benzofuran-1-yl]imidazo[1,2-a]-pyridine Prepared from Intermediate 12 and Intermediate 18 by a method analogous to that used to prepare Intermediate 3, to afford the title compound (155 mg, 31.8%) as a brown gum. $\delta_H$ (500 MHz, DMSO-d$_6$) (isomer A): 8.05 (s, 1H), 7.56-7.39 (m, 3H), 7.36-7.27 (m, 2H), 7.06 (d, J7.3 Hz, 1H), 6.87 (d, J2.4 Hz, 1H), 5.33 (qd, J6.3, 2.8 Hz, 1H), 2.13 (s, 3H), 1.57 (d, J6.4 Hz, 3H); (isomer B): 7.92 (s, 1H), 7.56-7.39 (m, 3H), 7.36-7.27 (m, 2H), 6.95 (d, J7.5 Hz, 1H), 6.69 (d, J2.6 Hz, 1H), 5.51 (qd, J6.2, 2.2 Hz, 1H), 2.27 (s, 3H), 1.49 (d, J 6.4 Hz, 3H). LCMS m/z 343.1 [M+H]+.

Intermediates 20 to 22

The following compounds were prepared by a method analogous to that used to prepare Intermediate 16, by catalytic coupling of Intermediate 14 with a suitable boronic acid or pinacol boronate.

| Intermediate | Name | LCMS m/z [M + H]+ |
|---|---|---|
| 20 | tert-Butyl 4-(5-{2-methyl-3-[(1S,3S)-3-methyl-1,3-dihydro-2-benzofuran-1-yl]imidazo[1,2-a]pyridin-6-yl}pyrimidin-2-yl)-piperazine-1-carboxylate | 527.0 |
| 21 | 5-{2-Methyl-3-[(1S,3S)-3-methyl-1,3-dihydro-2-benzofuran-1-yl]imidazo[1,2-a]pyridin-6-yl}-2-{2-[(trimethylsilyl)oxy]propan-2-yl}pyridine | 471.9 |
| 22 | tert-Butyl 4-(5-{2-methyl-3-[(1S,3S)-3-methyl-1,3-dihydro-2-benzofuran-1-yl]imidazo[1,2-a]pyridin-6-yl}pyridin-2-yl)-piperazine-1-carboxylate | 526.1 |

Intermediate 23

[2-(Morpholin-4-yl)pyrimidin-5-yl]boronic acid

A solution of (2-chloropyrimidin-5-yl)boronic acid (1 g, 6.32 mmol), morpholine (2.19 mL, 25.26 mmol) and triethylamine (0.9 mL, 6.32 mmol) in ethanol (25 mL) was stirred at 20° C. for 1 h. Water (50 mL) was slowly added to the reaction mixture to form a precipitate that was collected by filtration, to afford the title compound (950 mg, 70%) as a cream solid. $\delta_H$ (250 MHz, DMSO-$d_6$) 8.63 (s, 2H), 8.05 (s, 2H), 3.68 (ddd, J23.4, 5.7, 3.9 Hz, 8H). LCMS m/z 210 [M+H]+.

Intermediate 24

{2-[(1R,5S)-8-(Methoxycarbonyl)-3-azabicyclo[3.2.1]octan-3-yl]pyrimidin-5-yl}boronic acid (1R,5S)-3-tert-Butoxycarbonyl-3-azabicyclo[3.2.1]octane-8-carboxylic acid (9.0 g, 35.3 mmol) was suspended in HCl solution (2.25M in MeOH) and the reaction mixture was heated at reflux for 4 h. The reaction mixture was allowed to cool to room temperature, then concentrated in vacuo. To the resulting white solid was added (2-chloropyrimidin-5-yl)boronic acid (5.58 g, 35.2 mmol) and the mixture was suspended in EtOH (130 mL). Triethylamine (9.90 mL, 70.5 mmol) was added and the reaction mixture was heated at 80° C. for 5 h. The reaction mixture was allowed to cool to room temperature, then water (30 mL) was added. The reaction mixture was concentrated to around one-third volume, then more water (100 mL) was added. The resulting off-white solid precipitate was filtered and washed with water (2×30 mL), to afford the title compound (8.9 g, 86%) as an off-white powder. $\delta_H$ (300 MHz, DMSO-$d_6$) 8.59 (2H, s), 8.02 (2H, s), 4.45 (2H, dd, J 13.1, 3.4 Hz), 3.62 (3H, s), 2.98 (2H, br d, J 12.4 Hz), 2.77 (1H, s), 2.59 (2H, br s), 1.66-1.63 (2H, m), 1.38-1.33 (2H, m). LCMS m/z 292 [M+H]+.

Intermediate 25

[2-(5-Oxo-1,4-diazepan-1-yl)pyrimidin-5-yl]boronic acid

Prepared by a method analogous to that used to prepare Intermediate 23, by reacting 1,4-diazepan-5-one and (2-chloropyrimidin-5-yl)boronic acid in NMP, to afford the title compound (296 mg, 20%) as a cream solid. LCMS m/z 237 [M+H]+.

Intermediate 26

Ethyl 4-methyl-1-[5-(4,4,5,5-tetramethyl-1,3,2-dioxaborolan-2-yl)pyrimidin-2-yl]piperidine-4-carboxylate Prepared by a method analogous to that used to prepare Intermediate 23, using 2-chloro-5-(4,4,5,5-tetramethyl-1,3,2-dioxaborolan-2-yl)pyrimidine and ethyl 4-methyl-piperidine-4-carboxylate.

Intermediate 27

(6-Bromo-2-methylimidazo[1,2-a]pyridin-3-yl)[2-(1,3-dioxolan-2-yl)phenyl]methanol 2-(2-Bromophenyl)-1,3-dioxolane (0.15 g, 0.63 mmol) was dissolved in THF (3 mL) and cooled to −78° C. n-Butyllithium (0.28 mL of a 2.5M solution in cyclohexane, 0.70 mmol) was added dropwise and the resulting solution was stirred at −78° C. for 1 h. A solution of 6-bromo-2-methylimidazo[1,2-a]pyridine-3-carbaldehyde (0.15 g, 0.63 mmol) in THF (3 mL) was added dropwise to the reaction mixture at −78° C. The reaction mixture was allowed to warm to room temperature over 4 h, then diluted with EtOAc and washed with brine. The organic layer was dried over $Na_2SO_4$ and concentrated under reduced pressure. The crude residue was purified by chromatography on silica (eluting with EtOAc:hexanes, 40-100%) to afford the title compound (138 mg, 56%) as an off-white solid. $\delta_H$ (300 MHz, DMSO-$d_6$) 8.50 (d, J 1.2 Hz, 1H), 7.67 (d, J7.3 Hz, 1H), 7.55 (dd, J7.5, 1.4 Hz, 1H), 7.49-7.44 (m, 2H), 7.39-7.34 (m, 1H), 7.31 (dd, J9.5, 1.9 Hz, 1H), 6.55 (d, J4.3 Hz, 1H), 6.15 (d, J4.6 Hz, 1H), 5.70 (s, 1H), 3.98-3.75 (m, 4H), 1.93 (s, 3H). LCMS m/z 389 [M+H]+.

Intermediate 28

3-(6-Bromo-2-methylimidazo[1,2-a]pyridin-3-yl)-1,3-dihydroisobenzofuran-1-ol

Intermediate 27 (0.16 g, 0.42 mmol) was taken up in THF (2 mL), then 2M HCl solution was added (2 mL, 4 mmol). The reaction mixture was stirred at room temperature for 2 h, then neutralised with saturated aqueous sodium bicarbonate solution. The resulting precipitate was filtered and dried to afford the title compound (111 mg, 76%) as a cream solid, which was used directly in the next step without further purification. LCMS m/z 345 [M+H]+.

Intermediate 29

6-Iodo-2-methylimidazo[1,2-a]pyridine

A solution of 5-iodopyridin-2-amine (25 g, 114 mmol) and 1-chloropropan-2-one (18.1 mL, 227 mmol) in ethanol (150 mL) was stirred at 80° C. for 16 h. Additional 1-chloropropan-2-one (2.72 mL, 33.9 mmol) was added and stirring at 80° C. was continued for 16 h. The mixture was allowed to cool to room temperature and the solvent was removed in vacuo. The residue was partitioned between DCM and aqueous NaOH solution (1M) and the layers were separated. The aqueous layer was extracted twice with DCM. The combined organic layers were dried over $Na_2SO_4$ and the solvent was removed in vacuo. The residue was purified by chromatography on silica gel (60-100% EtOAc in heptane, followed by 40-80% MeCN in DCM) to give the title compound (16.6 g, 56%) as a light brown solid. $\delta_H$ (300 MHz, DMSO-$d_6$) 8.83 (dd, J 1.5, 1.0 Hz, 1H), 7.62 (s, 1H), 7.33 (dd, J 9.3, 1.6 Hz, 1H), 7.28 (d, J 9.3 Hz, 1H), 2.32 (d, J 0.7 Hz, 3H).

Intermediate 30

6-Iodo-2-methylimidazo[1,2-a]pyridine-3-carbaldehyde

A solution of Intermediate 29 (15 g, 58.126 mmol) in DMF (150 mL) at 0-5° C. was treated with $POCl_3$ (14.0 mL, 23.0 g, 150 mmol) dropwise over 15 minutes. A white solid was formed. The mixture was stirred at this temperature for 1 h, then warmed to room temperature, then heated at 70° C. for 6 h, before cooling to room temperature and standing overnight. The reaction mixture was poured into ice/water (200 mL) and treated with aqueous NaOH solution (300 mL), then the aqueous layer was extracted into EtOAc (3×300 mL). The combined organic extracts were washed with water (2×200 mL) and brine (200 mL), then dried ($Na_2SO_4$), filtered and concentrated in vacuo. The resulting crude solid was triturated with diethyl ether to give the title compound (11.2 g, 67%) as a pale orange solid. $\delta_H$ (300 MHz, DMSO-$d_6$) 10.01 (s, 1H), 9.63 (d, 1H, J0.6 Hz), 7.87 (dd, 1H, J9.2, 1.6 Hz), 7.61 (d, 1H, J9.2 Hz), 2.64 (s, 3H). LCMS m/z 286.8 [M+H]$^+$.

Intermediate 31

1-{2-[(Hydrox)(6-iodo-2-methylimidazo[1,2-a]pyridin-3-yl)methyl]phenyl}ethanol n-Butyllithium (6.9 mL, 2.5M in hexanes) was added in two portions (3.45 mL dropwise, then 3.45 mL at once) to a solution of 1-phenylethanol (1.22 g, 10.0 mmol) and TMEDA (2.60 mL, 17.2 mmol) in n-pentane (40 mL) at room temperature. The resulting mixture was heated to 40° C. and stirred overnight. The mixture was diluted with n-pentane (40 mL) and cooled to −78° C., then Intermediate 30 (2.0 g, 7.0 mmol) was added as a solid in small portions. The mixture was stirred for 15 minutes at −78° C., then warmed to room temperature. After 5 h, the mixture was poured onto water and extracted four times with EtOAc. The combined organic layers were washed with brine, dried ($Na_2SO_4$) and concentrated in vacuo. The resulting yellow oil was purified by flash chromatography (10% MeOH in DCM). Product fractions were concentrated, and the oily residue was co-evaporated once with $Et_2O$, to afford the title compound (1.30 g, 82%) as a light yellow solid. LCMS m/z 409 [M+H]$^+$.

Intermediate 32

1-{2-[(6-Bromo-2-methylimidazo[1,2-a]pyridin-3-yl)(hydroxy)methyl]-3-methoxyphenyl}ethanol Prepared from 6-bromo-2-methylimidazo[1,2-a]pyridine-3-carbaldehyde and 1-(3-methoxyphenyl)ethanol by a method analogous to that used to prepare Intermediate 31, to afford the title compound (31% yield). LCMS m/z 393.0 [M+H]$^+$.

Intermediate 33

2-{2-[(Hydroxy)(6-iodo-2-methylimidazo[1,2-a]pyridin-3-yl)methyl]phenyl}propan-2-ol n-Butyllithium solution (2.5M, 8.8 mL, 22 mmol) was added at −78° C. to a solution of α,α-dimethylbenzyl alcohol (1.5 g, 11 mmol) in anhydrous toluene (12 mL). The mixture was stirred overnight, allowing the temperature to rise slowly. The turbid solution was cooled again to −78° C. and a solution of Intermediate 30 (2.5 g, 8.74 mmol) in toluene (20 mL) was added dropwise. The mixture was stirred for 4 h, with warming slowly to room temperature. The reaction mixture was poured into ice/saturated aqueous ammonium chloride solution, then extracted into EtOAc. The organic extract was dried ($MgSO_4$) and concentrated. The crude residue was purified by chromatography on silica gel (EtOAc). The resulting material was crystallised from IPA and filtered, then washed with ether/hexane and dried, to give the title compound (0.44 g, 12%) as a light pink crystalline solid. $\delta_H$ (400 MHz, DMSO-$d_6$) 8.75 (s, 1H), 7.61 (m, 1H), 7.38 (m, 2H), 7.28 (m, 3H), 7.13 (d, J5.6 Hz, 1H), 5.90 (d, J5.6 Hz, 1H), 5.16 (s, 1H), 1.76 (s, 3H), 1.56 (s, 3H), 1.34 (s, 3H). LCMS m/z 423 [M+H]$^+$.

Intermediate 34

1-Bromo-2-[2,2,2-trifluoro-1-(2-methoxyethoxymethoxy)ethyl]benzene

To a solution of 1-(2-bromophenyl)-2,2,2-trifluoroethanol (1.00 g, 3.92 mmol) in THF (10 mL) at 0° C. was added sodium hydride (60% in mineral oil, 0.165 g, 4.13 mmol). The mixture was stirred for 30 minutes before the dropwise addition of 2-methoxyethoxymethyl chloride (0.862 g, 5.88 mmol, 0.790 mL). After 20 minutes, the reaction mixture was allowed to warm to room temperature. After 3 h, the reaction mixture was partitioned between EtOAc (100 mL) and water (100 mL). The aqueous layer was extracted into EtOAc (20 mL). The combined organic layers were washed with water (20 mL) and brine (20 mL), then dried ($Na_2SO_4$), filtered and concentrated in vacuo. The resulting crude material was purified by chromatography on silica gel (eluting with hexane to 25% EtOAc) to give the title compound (1.02 g, 76%) as a clear oil. $\delta_H$ (400 MHz, $CDCl_3$) 7.63 (m, 2H), 7.40 (td, 1H, J7.6, 1.1 Hz), 7.28 (m, 1H), 5.66 (q, 1H, J6.5 Hz), 4.87 (d, 1H, J6.9 Hz), 4.69 (d, 1H, J6.9 Hz), 3.82 (m, 1H), 3.53 (m, 3H), 3.38 (s, 3H).

Intermediate 35

(6-Iodo-2-methylimidazo[1,2-a]pyridin-3-yl){2-[2,2,2-trifluoro-1-(2-methoxyethoxy-methoxy)ethyl]phenyl}methanol To a solution of Intermediate 34 (0.35 g, 1.0 mmol) in THF (4 mL) at −78° C. was added n-butyllithium (2.5M, 0.51 mL, 1.3 mmol) dropwise. The mixture was stirred at this temperature for 15 minutes before the dropwise addition of a solution of Intermediate 30 (0.29 g, 1.0 mmol) in THF (4 mL). The mixture was stirred for 20 minutes, then allowed to warm to room temperature and stirred for a further 3 h. The reaction mixture was quenched by partitioning between EtOAc (30 mL) and saturated aqueous NH₄Cl solution (30 mL). The organic layers were separated, washed with water (10 mL) and brine (10 mL), then dried (Na₂SO₄) and filtered. The solvent was removed in vacuo. The resulting crude oil was purified by chromatography on silica, eluting with hexane to EtOAc, to give the title compound (0.052 g, 9.3%) as a clear oil. LCMS m/z 551.0 [M+H]⁺.

Intermediate 36

3-Hydroxyisoindolin-1-one

Prepared according to a literature procedure (*Beilstein J. Org. Chem.*, 2012, 8, 192-200). Phthalimide (5 g, 33.9 mmol) was dissolved in MeOH (85 mL) and THF (175 mL), then cooled to 0° C. Sodium borohydride (1.3 g, 34 mmol) was added portionwise over 10 minutes, then the reaction mixture was stirred at 0° C. for a further 30 minutes. The reaction mixture was quenched with water and extracted with EtOAc, then the organic layers were dried over sodium sulphate and concentrated under reduced pressure. The residue was purified by recrystallization from EtOH:water (1:1) to afford the title compound (2 g, 39%) as colourless crystals.

Intermediate 37

3-Hydroxy-2-methylisoindolin-1-one

Prepared according to a literature procedure (*Beilstein J. Org. Chem.*, 2012, 8, 192-200). N-Methylphthalimide (5 g, 30.4 mmol) was dissolved in MeOH (85 mL) and THF (175 mL), then cooled to 0° C. Sodium borohydride (1.15 g, 30 mmol) was added portionwise over 10 minutes, then the reaction mixture was stirred at 0° C. for a further 30 minutes. The reaction mixture was quenched with water and extracted with EtOAc, then the organic layers were dried over sodium sulphate and concentrated under reduced pressure, to afford the title compound (3.64 g, 73%) as a white solid.

Intermediate 38

(3S)-3-Methyl-1,3-dihydroisobenzofuran-1-ol

Prepared from (1S)-1-phenylethanol by a method analogous to that used to prepare Intermediate 4.

Intermediate 39

6-Bromo-7-fluoro-2-methyl-3-[(3S)-3-methyl-1,3-dihydroisobenzofuran-1-yl]imidazo-[1,2-a]pyridine The title compound may be prepared from Intermediate 1 and Intermediate 38 by a method analogous to that used to prepare Intermediate 3.

Intermediate 40

3-Hydroxy-3-methylisoindolin-1-one

Prepared according to the procedure described in *Synth. Commun.*, 2004, 34, 853-861.

Phthalimide (2 g, 13.5 mmol) was dissolved in DCM (140 mL) and cooled to 0° C. Methylmagnesium iodide (13.5 mL, 40.3 mmol) was added dropwise over 5 minutes and the reaction mixture was stirred at 0° C. for a further 3 h. Methylmagnesium iodide (4.5 mL, 13.5 mmol) was added and the reaction mixture was allowed to warm to room temperature overnight. The reaction mixture was quenched with saturated aqueous ammonium chloride solution, then extracted with DCM. The organic layers were washed with brine, dried over sodium sulphate and concentrated under reduced pressure, to afford the title compound (2.19 g, 99%) as a white solid.

Intermediate 41

3-Methylisoindolin-1-one

Prepared according to the procedure described in *Synth. Commun.*, 2004, 34, 853-861.

Intermediate 40 (1.5 g, 9.2 mmol) was dissolved in DCM (100 mL) and cooled to −15° C. Triethylsilane (15 mL, 92 mmol) was added, followed by boron trifluoride diethyl etherate (3.5 mL, 27 mmol), and the reaction mixture was allowed to warm to room temperature overnight. The reaction mixture was quenched with saturated aqueous sodium bicarbonate solution, then extracted with DCM. The organic layers were washed with brine, dried over sodium sulphate and concentrated under reduced pressure. The residue was purified by chromatography on silica gel (20-90% EtOAc:hexane) to afford the title compound (0.67 g, 50%) as an off-white solid.

Intermediate 42 tert-Butyl 1-methyl-3-oxoisoindoline-2-carboxylate

Intermediate 41 (0.67 g, 4.5 mmol) was suspended in DCM (60 mL). Triethylamine (0.64 mL, 4.5 mmol) was added, followed by di-tert-butyl dicarbonate (2.0 g, 9.1 mmol) and 4-(dimethylamino)pyridine (0.56 g, 4.5 mmol). The reaction mixture was stirred at room temperature overnight, then concentrated under reduced pressure. The residue was purified by chromatography on silica gel (0-20% EtOAc:hexane) to afford the title compound (1.01 g, 90%) as a colorless oil. $\delta_H$ (300 MHz, CDCl₃) 7.76-7.54 (m, 3H), 7.54 (t, J7.1 Hz, 1H), 5.09 (q, J6.5 Hz, 1H), 1.55 (d, J6.5 Hz, 3H), 1.53 (s, 9H).

Intermediate 43 tert-Butyl 1-hydroxy-3-methylisoindoline-2-carboxylate

Intermediate 42 (0.49 g, 1.8 mmol) was dissolved in THF (10 mL) and cooled to −78° C. Diisobutylaluminium hydride (2.7 mL of a 1M solution in THF, 2.7 mmol) was added dropwise and the reaction mixture was allowed to warm to room temperature slowly overnight. Saturated aqueous sodium acetate solution (10 mL) was added. The mixture was stirred for 10 minutes, then a mixture of diethyl ether and saturated aqueous ammonium chloride solution (3:1, 35 mL) was added. The mixture was stirred for 15 minutes. The phases were separated and the aqueous layer was extracted with diethyl ether. The organic layers were washed with brine, then dried over sodium sulphate and concentrated under reduced pressure. The residue was purified by chromatography on silica gel (0-20% EtOAc:hexane) to afford the title compound (0.26 g, 46%), mixture of diastereoisomers, as a pink solid. $\delta_H$ (300 MHz, CDCl₃) 7.39-7.30 (m, 4H), 6.27-6.00 (m, 2H), 4.90-4.74 (m, 1H), 1.48-1.46 (m, 12H).

Intermediate 44 tert-Butyl 1-methoxy-3-methylisoindoline-2-carboxylate

Intermediate 43 (0.79 g, 2.5 mmol) was dissolved in MeOH (15 mL). Pyridinium p-toluenesulfonate (0.06 g, 0.25 mmol) was added and the reaction mixture was stirred at room temperature for 3 h. Triethylamine (0.16 mL, 1.1 mmol) was added and the reaction mixture was concentrated under reduced pressure to afford the title compound (0.67 g, 99%) as a brown oil. $\delta_H$ (300 MHz, CDCl$_3$) 7.48-7.33 (m, 4H), 6.13 (br s, 1H), 4.85 (q, J6.2 Hz, 1H), 3.26 (s, 3H), 1.47-1.44 (m, 12H).

Intermediate 45 tert-Butyl (1R,3R)-1-(6-bromo-2-methylimidazo[1,2-a]pyridin-3-yl)-3-methylisoindoline-2-carboxylate and tert-Butyl (1S,3S)-1-(6-bromo-2-methylimidazo[1,2-a]pyridin-3-yl)-3-methylisoindoline-2-carboxylate Intermediate 44 (0.84 g, 3.2 mmol) and 6-bromo-2-methylimidazo[1,2-a]pyridine (0.28 g, 1.3 mmol) were dissolved in acetonitrile (10 mL). Pyridinium p-toluenesulfonate (1.33 g, 5.31 mmol) was added and the reaction mixture was heated at 80° C. for 72 h. The reaction mixture was diluted with EtOAc, then washed with saturated aqueous sodium bicarbonate solution and brine. The organic layers were concentrated under reduced pressure. The residue was purified by chromatography on silica gel (0-100% EtOAc:hexane). Further purification by preparative HPLC afforded the title compound (30 mg, 5%) as an off-white solid. $\delta_H$ (300 MHz, CDCl$_3$) 7.48-7.38 (m, 3H), 7.32-7.24 (m, 2H), 6.92 (d, J7.8 Hz, 1H), 6.67 (br s, 1H), 5.09 (q, J6.3 Hz, 1H), 1.98 (s, 3H), 1.57-1.53 (m, 3H), 1.29 (br s, 9H).

Intermediate 46 tert-Butyl (1S,3R)-1-(6-bromo-2-methylimidazo[1,2-a]pyridin-3-yl)-3-methylisoindoline-2-carboxylate and tert-Butyl (1R,3S)-1-(6-bromo-2-methylimidazo[1,2-a]pyridin-3-yl)-3-methylisoindoline-2-carboxylate Purification by preparative HPLC of the residue from the reaction described for Intermediate 45 afforded the title compound (80 mg, 14%) as an off-white solid. $\delta_H$ (300 MHz, CDCl$_3$) 7.49-7.22 (m, 5H), 6.97-6.94 (m, 1H), 6.76 (br s, 1H), 5.30-5.14 (m, 1H), 1.71 (s, 3H), 1.57-1.53 (m, 3H), 0.83 (s, 9H).

Intermediate 47

7-Fluoro-2-methyl-6-[4-(methylsulfonyl)phenyl]imidazo[1,2-a]pyridine

Prepared from Intermediate 1 and 4-(methylsulfonyl)benzeneboronic acid by a method analogous to that used to prepare Intermediate 16 to afford the title compound (2.0 g, 54%) as a tan powder. $\delta_H$ (d$_6$-DMSO) 8.82 (d, J7.7 Hz, 1H), 8.05 (d, J 8.4 Hz, 2H), 7.85 (d, J9.9 Hz, 2H), 7.70 (s, 1H), 7.47 (d, J 11.7 Hz, 1H), 3.28 (s, 3H), 2.34 (s, 3H).

Intermediate 48

Ethyl 4-(5-{2-methyl-3-[(1S,3S)-3-methyl-1,3-dihydro-2-benzofuran-1-yl]imidazo[1,2-a]-pyridin-6-yl}pyrimidin-2-yl)cyclohex-3-ene-1-carboxylate Prepared from Intermediate 14 and ethyl 4-[5-(4,4,5,5-tetramethyl-1,3,2-dioxaborolan-2-yl)pyrimidin-2-yl]cyclohex-3-ene-1-carboxylate by a method analogous to that used to prepare Intermediate 16 to afford the title compound (654 mg, 76%) as a white solid. $\delta_H$ (500 MHz, CD$_3$OD) 8.61 (s, 2H), 7.89 (s, 1H), 7.64 (s, 2H), 7.48 (d, J6.6 Hz, 2H), 7.35-7.30 (m, 1H), 7.29 (s, 1H), 6.97 (d, J7.5 Hz, 1H), 6.76 (d, J2.5 Hz, 1H), 5.44 (dd, J6.3, 2.6 Hz, 1H), 4.17 (q, J6.9 Hz, 2H), 2.77 (s, 1H), 2.72-2.63 (m, 1H), 2.61-2.49 (m, 3H), 2.47 (s, 3H), 2.18 (dd, J8.6, 4.4 Hz, 1H), 1.87-1.77 (m, 1H), 1.65 (d, J6.4 Hz, 3H), 1.27 (t, J7.1 Hz, 3H).

Intermediate 49

Ethyl 4-(5-{2-methyl-3-[(1S,3S)-3-methyl-1,3-dihydro-2-benzofuran-1-yl]imidazo[1,2-a]-pyridin-6-yl}pyrimidin-2-yl)cyclohexane-1-carboxylate Prepared from Intermediate 48 by a method analogous to that used to prepare Intermediate 17 to afford the title compound (516 mg, 79%) as a yellow oil. $\delta_H$ (500 MHz, CD$_3$OD) 8.64 (s, 2H), 7.90 (s, 1H), 7.67-7.59 (m, 2H), 7.47 (d, J6.8 Hz, 2H), 7.36-7.28 (m, 1H), 6.96 (d, J7.5 Hz, 1H), 6.75 (d, J2.6 Hz, 1H), 5.43 (dd, J6.3, 2.6 Hz, 1H), 4.16 (dt, J 13.4, 6.9 Hz, 2H), 3.02-2.84 (m, 1H), 2.71-2.64 (m, 1H), 2.45 (s, 3H), 2.20-2.04 (m, 3H), 2.00-1.82 (m, 3H), 1.72 (ddd, J 13.2, 9.8, 4.2 Hz, 2H), 1.64 (d, J6.3 Hz, 3H), 1.27 (td, J7.1, 3.1 Hz, 3H).

Intermediate 50

6-Bromo-2-methyl-3-[(3S)-3-methyl-1,3-dihydro-2-benzofuran-1-yl]imidazo[1,2-a]-pyrazine Prepared from Intermediate 38 and 6-bromo-2-methylimidazo[1,2-a]pyrazine by a method analogous to that used to prepare Intermediate 3 to afford the title compound (100 mg, 21%) as a yellow gum. LCMS m/z 344 [M+H]$^+$.

Intermediate 51

6-Bromo-2-(methoxymethyl)imidazo[1,2-a]pyridine-3-carbaldehyde

To a solution of 6-bromo-2-(methoxymethyl)imidazo[1,2-a]pyridine (4.0 g, 17 mmol) in DMF (50.0 mL, 645 mmol) at room temperature was added DMF (50.0 mL, 645 mmol) dropwise. The mixture was heated at 70° C. for 3 h. The reaction mixture was partitioned between ice/water (300 mL) and EtOAc (300 mL). The organic phase was separated and the aqueous phase was extracted into EtOAc (50 mL). The combined organic phases were washed with water (3×50 mL) and brine (50 mL), then dried over Na$_2$SO$_4$, filtered and concentrated in vacuo, to afford the title compound (3.8 g, 85%) as a white solid. LCMS m/z 269 [M+H]$^+$.

Intermediate 52

[6-Bromo-2-(methoxymethyl)imidazo[1,2-a]pyridin-3-yl][2-(tetrahydropyran-2-yloxy-methyl)phenyl]methanol A mixture of 2-[(2-bromophenyl)methoxy]tetrahydropyran (0.5 g, 1.8 mmol) and magnesium (0.054 g, 2.2 mmol) in THF (4 mL) was heated at 75° C. for 2 h. The mixture was cooled in an ice bath and treated with a solution of Intermediate 51 (0.42 g, 1.5608 mmol) in THF (10 mL). The mixture was partitioned between EtOAc (50 mL) and saturated aqueous NH$_4$Cl solution (40 mL). The organic layer was separated and the aqueous layer was re-extracted into EtOAc (10 mL). The combined organic layers were washed with brine (5 mL), dried and concentrated in vacuo. The residue was purified by chromatography on silica gel (0-100% EtOAc:hexane) to afford the title compound (641 mg, 89%) as a clear oil. LCMS m/z 463 [M+H]$^+$.

Example 1

2-{5-[7-Fluoro-2-methyl-3-(3H-spiro[2-benzofuran-1,1'-cyclopropan]-3-yl)imidazo[1,2-a]pyridin-6-yl]pyrimidin-2-yl}propan-2-ol Intermediate 3 (160 mg, 0.43 mmol) and 2-[5-(4,4,5,5-tetramethyl-1,3,2-dioxaborolan-2-yl)pyrimidin-2-yl]propan-2-ol (170 mg, 0.64 mmol) were dissolved in 1,4-dioxane (3 mL) and 2M sodium carbonate in water (750 µL) was added. The resulting mixture was degassed with nitrogen for 5 minutes, then Pd(dppf)Cl$_2$ (20 mg, 0.02 mmol) was added and the reaction mixture was heated in a sealed tube at 105° C. for 1 h. The reaction mixture was diluted with EtOAc (5 mL) and washed with water (3 mL). The aqueous layer was re-extracted with EtOAc (3 mL), then the combined organic layers were dried over Na$_2$SO$_4$ and concentrated to dryness under vacuum. The crude residue (250 mg) was purified by chromatography on silica gel, eluting with 0-5% MeOH in DCM. The resulting crude material (200 mg) was further purified using preparative HPLC to afford the title compound (77.8 mg, 42.2%) as an off-white solid. δ$_H$ (500 MHz, CDCl$_3$) 8.60 (d, J 1.5 Hz, 2H), 7.74 (d, J7.2 Hz, 1H), 7.39 (t, J7.6 Hz, 1H), 7.33 (d, J 10.7 Hz, 1H), 7.26 (t, J7.5 Hz, 1H), 6.95 (d, J8.2 Hz, 2H), 6.82 (s, 1H), 4.49 (s, 1H), 2.58 (s, 3H), 1.63 (s, 6H), 1.51 (ddd, J11.6, 7.4, 5.7 Hz, 1H), 1.36 (ddd, J11.4, 7.5, 5.8 Hz, 1H), 1.17 (ddd, J 11.0, 7.3, 5.9 Hz, 1H), 1.04 (ddd, J 11.0, 7.5, 5.7 Hz, 1H). LCMS m/z 431.1 [M+H]$^+$.

Example 2

2-(5-{3-[(1S,3R)-3-Ethyl-1,3-dihydroisobenzofuran-1-yl]-7-fluoro-2-methylimidazo[1,2-a]pyridin-6-yl}pyrimidin-2-yl)propan-2-ol Isolated from the process described in Example 1, to give the title compound (4 mg, 2.4%) as an off-white solid. δ$_H$ (500 MHz, CDCl$_3$) 8.53 (d, J 1.2 Hz, 2H), 7.60 (d, J 7.2 Hz, 1H), 7.43 (t, J7.5 Hz, 1H), 7.37-7.31 (m, 2H), 7.29 (t, J7.5 Hz, 1H), 6.91 (d, J 7.5 Hz, 1H), 6.55 (d, J2.9 Hz, 1H), 5.22 (dt, J7.0, 3.2 Hz, 1H), 4.48 (s, 1H), 2.54 (s, 3H), 2.17 (dqd, J 14.9, 7.4, 3.7 Hz, 1H), 1.81 (dp, J 14.7, 7.4 Hz, 1H), 1.61 (s, 6H), 1.08 (t, J 7.4 Hz, 3H). LCMS m/z 433.2 [M+H]$^+$.

Example 3

2-(5-{3-[(1S,3S)-3-Ethyl-1,3-dihydroisobenzofuran-1-yl]-7-fluoro-2-methylimidazo[1,2-a]pyridin-6-yl}pyrimidin-2-yl)propan-2-ol Isolated from the process described in Example 1, to give the title compound (11.5 mg, 6.4%) as an off-white solid. δ$_H$ (500 MHz, CDCl$_3$) 8.55 (d, J 1.4 Hz, 2H), 7.47 (d, J 7.2 Hz, 1H), 7.43 (t, J7.5 Hz, 1H), 7.36 (d, J7.5 Hz, 1H), 7.34 (d, J 10.7 Hz, 1H), 7.30 (t, J7.4 Hz, 1H), 6.97 (d, J7.6 Hz, 1H), 6.71 (d, J2.6 Hz, 1H), 5.42 (ddd, J7.1, 4.0, 2.8 Hz, 1H), 4.48 (s, 1H), 2.55 (s, 3H), 1.99-1.91 (m, 1H), 1.87 (dq, J 14.4, 7.3 Hz, 1H), 1.62 (s, 6H), 1.07 (t, J 7.4 Hz, 3H). LCMS m/z=433.2 [M+H]$^+$.

Example 4

2-(5-{7-Fluoro-2-methyl-3-[(3R)-3-methyl-1,3-dihydro-2-benzofuran-1-yl]imidazo[1,2-a]pyridin-6-yl}pyrimidin-2-yl)propan-2-ol Intermediate 5 (146.3 mg, 0.41 mmol) and 2-[5-(4,4,5,5-tetramethyl-1,3,2-dioxaborolan-2-yl)pyrimidin-2-yl]propan-2-ol (130 mg, 0.49 mmol) were dissolved in 1,4-dioxane (5 mL) and 2M sodium carbonate in water (0.6 mL) was added. The resulting mixture was degassed with nitrogen for 10 minutes, then Pd(dppf)Cl$_2$ (30 mg, 0.04 mmol) was added and the reaction mixture was heated at 100° C. for 15 minutes under microwave irradiation. The reaction mixture was concentrated under vacuum, then diluted with EtOAc (25 mL), then washed with aqueous NaHCO$_3$ solution (15 mL), water (20 mL) and brine (5 mL), then dried over Na$_2$SO$_4$ and concentrated under vacuum. The residue was purified by chromatography on silica gel, eluting with 0-10% MeOH in DCM. The crude material was further purified using preparative HPLC to afford the title compound (56.5 mg, 33.3%) as a brown gum. δ$_H$ (500 MHz, CD$_3$OD) 8.69 (d, J 15.0 Hz, 2H), 7.85 (dd, J7.0, 5.0 Hz, 1H), 7.47-7.28 (m, 4H), 7.02 (dd, J47.7, 7.5 Hz, 1H), 6.92-6.68 (m, 1H), 5.63-5.36 (m, 1H), 2.36 (d, J43.6 Hz, 3H), 1.58 (dd, J21.7, 5.3 Hz, 9H). LCMS m/z 419.5 [M+H]$^+$.

Example 5

Potassium (1R,5S,6R)-3-(5-{2-methyl-3-[(1S,3S)-3-methyl-1,3-dihydro-2-benzofuran-1-yl]imidazo[1,2-a]pyridin-6-yl}pyrimidin-2-yl)bicyclo[3.1.0]hexane-6-carboxylate Intermediate 17 (92 mg, 0.19 mmol) was dissolved in ethanol (3 mL) and 1M KOH in water (0.19 mL) was added. The mixture was stirred at 70° C. for 24 h. 1M KOH in water (0.02 mL) was added and the mixture was stirred at 70° C. for a further 4 h. The mixture was concentrated under vacuum and purified using preparative HPLC to afford the title compound (20.3 mg 21.6%) as a brown gum. δ$_H$ (500 MHz, CD$_3$OD) 8.60 (s, 2H), 7.88 (s, 1H), 7.63 (t, J7.8 Hz, 2H), 7.47 (d, J7.0 Hz, 2H), 7.32 (t, J7.1 Hz, 1H), 6.95 (d, J7.5 Hz, 1H), 6.75 (d, J2.4 Hz, 1H), 5.42 (qd, J6.1, 2.6 Hz, 1H), 3.10 (ddd, J 18.4, 10.5, 7.9 Hz, 1H), 2.44 (s, 3H), 2.29-2.16 (m, 4H), 1.86 (s, 2H), 1.63 (d, J6.3 Hz, 3H), 1.53 (t, J2.9 Hz, 1H). LCMS m/z 468.2 [M+H]$^+$.

Example 6

2-Methyl-3-[(1S,3R)-3-methyl-1,3-dihydro-2-benzofuran-1-yl]-6-[4-(methylsulfonyl)-phenyl]imidazo[1,2-a]pyridine Prepared from Intermediate 19 and [4-(methylsulfonyl)phenyl]boronic acid by a method analogous to that used to prepare Example 1, to afford the title compound (26 mg, 13.8%) as a pale yellow solid. $\delta_H$ (500 MHz, CDCl$_3$) 7.94 (d, J8.2 Hz, 2H), 7.69-7.62 (m, 2H), 7.46-7.34 (m, 6H), 7.31 (t, J7.4 Hz, 1H), 7.02 (d, J7.5 Hz, 1H), 6.79 (s, 1H), 5.65-5.54 (m, 1H), 3.07 (s, 3H), 2.51 (s, 3H), 1.61 (d, J6.4 Hz, 3H). LCMS m/z 419.0 [M+H]$^+$.

Example 7

2-Methyl-3-[(1R,3R)-3-methyl-1,3-dihydro-2-benzofuran-1-yl]-6-[4-(methylsulfonyl)-phenyl]imidazo[1,2-a]pyridine Prepared from Intermediate 19 and [4-(methylsulfonyl)phenyl]boronic acid by a method analogous to that used to prepare Example 1, to afford the title compound (33 mg, 17.5%) as a pale yellow solid. $\delta_H$ (500 MHz, CDCl$_3$) 7.92 (d, J8.2 Hz, 2H), 7.75-7.69 (m, 2H), 7.47-7.40 (m, 2H), 7.39-7.33 (m, 3H), 7.29 (t, J7.4 Hz, 1H), 6.93 (d, J7.5 Hz, 1H), 6.62 (s, 1H), 5.47-5.39 (m, 1H), 3.07 (s, 3H), 2.59 (s, 3H), 1.65 (d, J6.4 Hz, 3H). LCMS m/z 419.0 [M+H]$^+$.

Example 8

2-Methyl-3-[(1S,3S)-3-methyl-1,3-dihydro-2-benzofuran-1-yl]-6-[2-(piperazin-1-yl)-pyrimidin-5-yl]imidazo[1,2-a]pyridine Intermediate 20 (230 mg, 0.44 mmol) was suspended in 4M HCl in 1,4-dioxane (4 mL) and stirred for 90 minutes at ambient temperature, then concentrated to dryness under vacuum. The resulting crude material was purified using preparative HPLC to afford the title compound (26.2 mg, 13.5%) as a white solid. $\delta_H$ (500 MHz, CD$_3$OD) 8.31 (s, 2H), 7.73 (s, 1H), 7.59 (d, J9.3 Hz, 1H), 7.51 (dd, J9.3, 1.5 Hz, 1H), 7.45 (d, J7.0 Hz, 2H), 7.33-7.28 (m, 1H), 6.94 (d, J7.5 Hz, 1H), 6.73 (d, J2.5 Hz, 1H), 5.42 (dd, J6.3, 2.7 Hz, 1H), 4.13-4.06 (m, 4H), 3.30-3.26 (m, 4H), 2.46 (s, 3H), 1.63 (d, J6.3 Hz, 3H). LCMS m/z 427.1 [M+H]$^+$.

Example 9

2-(5-{2-Methyl-3-[(1S,3S)-3-methyl-1,3-dihydro-2-benzofuran-1-yl]imidazo[1,2-a]-pyridin-6-yl}pyridin-2-yl)propan-2-ol Intermediate 21 (140 mg, 0.3 mmol) was dissolved in THF (2 mL). TBAF in THF (1M, 0.59 mL) was added and the reaction mixture was stirred at ambient temperature overnight, then concentrated under vacuum. The resulting dark yellow residue was taken up in DCM (20 mL), then washed sequentially with saturated aqueous NaHCO$_3$ solution (15 mL) and brine (15 mL). The organic layer was collected, dried over Na$_2$SO$_4$ and concentrated under vacuum. The crude residue was purified by chromatography on silica gel, eluting with DCM:MeOH (1:0 to 9:1). The resulting yellow gum was triturated with diethyl ether to afford the title compound (43 mg, 36%) as an off-white solid. $\delta_H$ (500 MHz, DMSO-d$_6$) 8.50 (d, J2.0 Hz, 1H), 8.01 (s, 1H), 7.78 (dd, J 8.3, 2.3 Hz, 1H), 7.69 (d, J 8.2 Hz, 1H), 7.64 (d, J9.3 Hz, 1H), 7.59 (dd, J9.3, 1.7 Hz, 1H), 7.49 (d, J7.5 Hz, 1H), 7.44 (t, J7.4 Hz, 1H), 7.30 (t, J7.3 Hz, 1H), 6.97 (d, J 7.5 Hz, 1H), 6.79 (d, J2.4 Hz, 1H), 5.36 (dd, J6.3, 2.6 Hz, 1H), 5.26 (s, 1H), 2.30 (s, 3H), 1.58 (d, J6.3 Hz, 3H), 1.45 (s, 7H). LCMS m/z 400.2 [M+H]$^+$.

Example 10

2-Methyl-3-[(1S,3S)-3-methyl-1,3-dihydro-2-benzofuran-1-yl]-6-[6-(piperazin-1-yl)-pyridin-3-yl]imidazo[1,2-a]pyridine Intermediate 22 (70 mg, 0.13 mmol) was dissolved in 4M hydrogen chloride in 1,4-dioxane (0.33 mL). The reaction mixture was stirred at ambient temperature overnight. The resulting precipitate was collected via filtration. The residue was taken up in DCM (20 mL) and saturated aqueous NaHCO$_3$ solution (15 mL). The organic layer was collected and dried over Na$_2$SO$_4$, then the solvent was removed under vacuum. The resulting yellow gum was triturated with diethyl ether to afford the title compound (25 mg, 44%) as a beige solid. $\delta_H$ (500 MHz, DMSO-d$_6$) 8.08 (d, J2.3 Hz, 1H), 7.78 (s, 1H), 7.57 (d, J9.3 Hz, 1H), 7.53-7.47 (m, 3H), 7.44 (t, J7.4 Hz, 1H), 7.30 (t, J7.4 Hz, 1H), 6.94 (d, J7.5 Hz, 1H), 6.85 (d, J8.9 Hz, 1H), 6.74 (d, J2.5 Hz, 1H), 5.35 (qd, J5.8, 2.2 Hz, 1H), 3.48-3.43 (m, 4H), 2.83-2.77 (m, 4H), 2.33 (s, 3H), 1.58 (d, J6.3 Hz, 3H). LCMS m/z 426.2 [M+H]$^+$.

Example 11

6-Bromo-2-methyl-3-[(3S)-3-methyl-1,3-dihydro-2-benzofuran-1-yl]imidazo[1,2-a]-pyridine Intermediate 12 (0.9 g, 4.26 mmol) and Intermediate 13 (70%, 2.5 g, 9.87 mmol) were dissolved in MeCN (8 mL) and pyridinium p-toluenesulfonate (4.3 g, 17.11 mmol) was added. The reaction mixture was stirred for 90 minutes at 100° C. under microwave irradiation. Intermediate 13 (70%, 1.5 g, 5.92 mmol) and pyridinium p-toluenesulfonate (2 g, 7.96 mmol) were added and the reaction mixture was stirred for 60 minutes at 100° C. under microwave irradiation. Intermediate 13 (70%, 1 g, 3.95 mmol) was added and the reaction mixture was stirred for 60 minutes at 100° C. under microwave irradiation. The reaction mixture was combined with previous batches. The combined reaction mixtures were concentrated under vacuum. The resulting dark brown oil was purified by chromatography on silica gel, eluting with 0-100% ethyl acetate in heptanes, to afford the title compound (5.2 g, 88.8%) as a dark brown oil. $\delta_H$ (500 MHz, CD$_3$OD) 7.84-7.79 (m, 2H), 7.47-7.40 (m, 6H), 7.37-7.28 (m, 4H), 7.02 (d, J7.6 Hz, 1H), 6.92 (d, J7.6 Hz, 1H), 6.82 (d, J2.4 Hz, 1H), 6.65 (d, J2.6 Hz, 1H), 5.59 (dd, J6.4, 2.5 Hz, 1H), 5.40 (dd, J6.3, 2.7 Hz, 1H), 2.44 (s, 3H), 2.33 (s, 3H), 1.66 (d, J6.4 Hz, 3H), 1.57 (d, J6.4 Hz, 3H). LCMS m/z 345 [M+H]$^+$.

Examples 12 TO 19

The following compounds were prepared by a method analogous to that used to prepare Example 1, by catalytic coupling of the appropriate starting material with a suitable boronic acid or pinacol boronate. Where applicable, chiral HPLC was used to separate isomers.

| Example | Name | Starting material | m/z |
|---|---|---|---|
| 12 | 2-Methyl-3-[(1S,3S)-3-methyl-1,3-dihydro-2-benzofuran-1-yl]-6-[2-(morpholin-4-yl)pyrimidm-5-yl]imidazo[1,2-a]pyridine | Intermediate 14 and Intermediate 23 | 428.5 |
| 13 | 2-Methyl-3-[(1S,3S)-3-methyl-1,3-dihydro-2-benzofuran-1-yl]-6-[4-(methylsulfonyl)phenyl]-imidazo[1,2-a]pyridine | Example 11 | 419.1 |
| 14 | 2-Methyl-3-[(1R,3S)-3-methyl-1,3-dihydro-2-benzofuran-1-yl]-6-[4-(methylsulfonyl)phenyl]-imidazo[1,2-a]pyridine formate salt | Example 11 | 419.0 |
| 15 | 2-(5-{2-Methyl-3-[(1S,3S)-3-methyl-1,3-dihydro-2-benzofuran-1-yl]imidazo[1,2-a]pyridin-6-yl}-pyrimidin-2-yl)propan-2-ol | Example 11 | 401.5 |
| 16 | 2-(5-{2-Methyl-3-[(1R,3S)-3-methyl-1,3-dihydro-2-benzofuran-1-yl]imidazo[1,2-a]pyridin-6-yl}-pyrimidin-2-yl)propan-2-ol | Example 11 | 401.1 |
| 17 | 2-Methyl-3-[(3R)-3-methyl-1,3-dihydro-2-benzofuran-1-yl]-6-[4-(methylsulfonyl)phenyl]-imidazo[1,2-a]pyridine | Intermediate 19 | 419.1 |
| 18 | 2-Methyl-3-[(3S)-3-methyl-1,3-dihydro-2-benzofuran-1-yl]-6-[4-(methylsulfonyl)phenyl]-imidazo[1,2-a]pyridine | Example 11 | 419.1 |
| 19 | Methyl(1R,5S)-3-(5-{2-methyl-3-[(3S)-3-methyl-1,3-dihydroisobenzofuran-1-yl]imidazo[1,2-a]-pyridin-6-yl}pyrimidin-2-yl)-3-azabicyclo[3.2.1]-octane-8-carboxylate | Example 30 and Intermediate 24 | 510 |

Example 20

(1R,5S)-3-(5-{2-Methyl-3-[(3S)-3-methyl-1,3-dihydroisobenzofuran-1-yl]imidazo[1,2-a]-pyridin-6-yl}pyrimidin-2-yl)-3-azabicyclo[3.2.1]octane-8-carboxylic acid Example 19 (173 mg, 0.34 mmol) was dissolved in THF (10 mL) and water (5 mL). Lithium hydroxide monohydrate (55 mg, 1.31 mmol) was added and the mixture was stirred at room temperature for 18 h. The mixture was distributed between water and ethyl acetate and the phases were separated. The aqueous layer was acidified to pH 3-4 with 2M aqueous HCl, then extracted with EtOAc. The combined organic layers were washed with brine and dried over $Na_2SO_4$, then concentrated in vacuo, to afford the title compound (140 mg, 83%) as an off-white solid, as a 1:1 mixture of diastereoisomers. $\delta_H$ (300 MHz, DMSO-$d_6$) 12.10 (s, 1H), 8.45 (s, 1H), 8.36 (s, 1H), 7.98 (s, 0.5H), 7.89 (s, 0.5H), 7.63-7.39 (m, 4H), 7.30 (d, J7.4 Hz, 1H), 7.07 (d, J7.5 Hz, 0.5H), 6.97-6.93 (m, 1H), 6.76 (d, J2.6 Hz, 0.5H), 5.59-5.56 (m, 0.5H), 5.36-5.33 (m, 0.5H), 4.43-4.35 (m, 2H), 3.01 (d, J 13.0 Hz, 2H), 2.67 (d, J3.0 Hz, 1H), 2.59 (br s, 2H), 2.28 (s, 1.5H), 2.18 (s, 1.5H), 1.70-1.66 (m, 2H), 1.56 (d, J6.3 Hz, 1.5H), 1.51 (d, J6.3 Hz, 1.5H), 1.38-1.36 (m, 2H). LCMS m/z 497 [M+H]$^+$.

Example 21

(1R,5S)-3-(5-{2-Methyl-3-[(1S,3S)-3-methyl-1,3-dihydroisobenzofuran-1-yl]imidazo[1,2-a]pyridin-6-yl}pyrimidin-2-yl)-3-azabicyclo[3.2.1]octane-8-carboxylic acid Example 20 was purified by preparative HPLC to afford the title compound (8 mg, 5%) as a white solid. $\delta_H$ (300 MHz, DMSO-$d_6$) 8.62 (s, 2H), 8.60 (s, 1H), 8.21 (dd, J9.4, 1.3 Hz, 1H), 8.01 (d, J9.4 Hz, 1H), 7.52-7.46 (m, 2H), 7.38-7.33 (m, 1H), 7.17 (d, J7.5 Hz, 1H), 6.93-6.92 (m, 1H), 5.43-5.37 (m, 1H), 4.46-4.40 (m, 2H), 3.04 (d, J 12.2 Hz, 2H), 2.69 (s, 1H), 2.60 (br s, 2H), 2.28 (s, 3H), 1.70-1.67 (m, 2H), 1.57 (d, J6.3 Hz, 3H), 1.36 (d, J 7.5 Hz, 2H). LCMS m/z 497 [M+H]$^+$.

Example 22

(1R,5S)-3-(5-{2-Methyl-3-[(1R,3S)-3-methyl-1,3-dihydroisobenzofuran-1-yl]imidazo[1,2-a]pyridin-6-yl}pyrimidin-2-yl)-3-azabicyclo[3.2.1]octane-8-carboxylic acid Example 20 was purified by preparative HPLC to afford the title compound (13 mg, 8%) as a white solid. $\delta_H$ (300 MHz, DMSO-$d_6$) 8.54 (s, 2H), 8.48 (s, 1H), 8.19 (dd, J 9.6, 0.9 Hz, 1H), 8.03 (d, J9.4 Hz, 1H), 7.51-7.45 (m, 2H), 7.39-7.34 (m, 1H), 7.26 (d, J 7.5 Hz, 1H), 7.09 (d, J2.2 Hz, 1H), 5.65-5.58 (m, 1H), 4.46 (dd, J 13.1, 3.4 Hz, 2H), 3.05 (d, J 12.0 Hz, 2H), 2.70 (s, 1H), 2.61 (br s, 2H), 2.16 (s, 3H), 1.70-1.68 (m, 2H), 1.52 (d, J6.3 Hz, 3H), 1.37 (d, J 7.7 Hz, 2H). LCMS m/z 497 [M+H]$^+$.

Example 23

2-(5-{7-Fluoro-2-methyl-3-[(3S)-3-methyl-1,3-dihydroisobenzofuran-1-yl]imidazo[1,2-a]pyridin-6-yl}pyrimidin-2-yl)propan-2-ol Prepared from Intermediate 39 and 2-[5-(4,4,5,5-tetramethyl-1,3,2-dioxaborolan-2-yl)pyrimidin-2-yl]propan-2-ol by a method analogous to that used to prepare Example 1, to afford the title compound (62 mg, 89%) as an off-white solid, as a 1:1 mixture of diastereoisomers. $\delta_H$ (300 MHz, DMSO-$d_6$) 8.79 (d, J 1.6 Hz, 1H), 8.75 (d, J 1.5 Hz, 1H), 8.19 (d, J7.3 Hz, 0.5H), 8.12 (d, J7.5 Hz, 0.5H), 7.56-7.51 (m, 1H), 7.38-7.32 (m, 2H), 7.27-7.22 (m, 1H), 7.04 (d, J7.4 Hz, 0.5H), 6.94 (d, J7.4 Hz, 0.5H), 6.86 (d, J2.1 Hz, 0.5H), 6.70 (d, J2.4 Hz, 0.5H), 5.49-5.44 (m, 0.5H), 5.28-5.22 (m, 0.5H), 5.07 (s, 0.5H), 5.07 (s, 0.5H), 2.11 (s, 1.5H), 2.00 (s, 1.5H), 1.47-1.45 (m, 7.5H), 1.42 (d, J6.4 Hz, 1.5H). LCMS m/z 419 [M+H]$^+$.

Example 24

3-(6-Bromo-2-methylimidazo[1,2-a]pyridin-3-yl)-3H-isobenzofuran-1-one

Intermediate 28 (39 mg, 0.11 mmol), 4-methylmorpholine N-oxide (30 mg, 0.26 mmol) and 4 Å molecular sieves were dissolved in DCM (0.5 mL). TPAP (2 mg, 0.01 mmol) was added and the reaction mixture was stirred at room temperature for 1 h. The reaction mixture was diluted with EtOAc and filtered, then the filtrate was concentrated under reduced pressure. The residue was purified by chromatography on silica gel (EtOAc:hexane 50-100%) to afford the title compound (5 mg, 13%) as a white solid. $\delta_H$ (300 MHz, DMSO-$d_6$) 8.62 (s, 1H), 8.04 (d, J7.6 Hz, 1H), 7.89-7.85 (m, 1H), 7.76 (t, J 7.5 Hz, 1H), 7.65 (dd, J7.6, 0.7 Hz, 1H), 7.57 (dd, J9.5, 0.7 Hz, 1H), 7.51 (s, 1H), 7.47 (dd, J9.5, 1.8 Hz, 1H), 1.81 (s, 3H). LCMS m/z 343 [M+H]$^+$.

Example 25

3-(3,3-Dimethyl-1H-isobenzofuran-1-yl)-6-iodo-2-methylimidazo[1,2-a]pyridine Aqueous hydrochloric acid (4N, 4 mL) was added to a solution/suspension of Intermediate 33 (0.44 g, 1.0 mmol) in 1,4-dioxane (8 mL). The reaction mixture was stirred overnight, then poured into a mixture of ice and dilute aqueous NaOH solution and extracted once using EtOAc. The organic extract was washed with water, dried (MgSO$_4$) and concentrated, then purified by chromatography on silica gel (eluting with EtOAc-hexane, 3:2, then 1:1). The residue was triturated in diethyl ether and filtered, then washed with diethyl ether and dried, to give the title compound (0.256 g, 61%) as off-white solid. $\delta_H$ (300 MHz, DMSO-$d_6$) 8.00 (s, 1H), 7.44 (m, 2H), 7.36 (m, 2H), 7.28 (m, 1H), 6.92 (m, 1H), 6.75 (s, 1H), 2.27 (s, 3H), 1.63 (s, 3H), 1.52 (s, 3H). LCMS m/z 405 [M+H]$^+$.

Example 26

3-(1,3-Dihydroisobenzofuran-1-yl)-6-iodo-2-methylimidazo[1,2-a]pyridine n-Butyllithium solution in hexanes (2.5M, 3.5 mL, 8.75 mmol) was added at −78° C. to a solution of benzyl alcohol (0.43 mL, 4.2 mmol) in anhydrous toluene (8 mL) and stirred overnight. The reaction mixture was cooled to −78° C. again and a solution of Intermediate 30 (1 g, 3.5 mmol) in toluene (8 mL) was added gradually and left stirring for 4 h, allowing the temperature to rise slowly to room temperature. The reaction mixture was poured into ice/saturated aqueous NH$_4$Cl solution, then extracted using EtOAc. The organic layer was dried (MgSO$_4$), concentrated and purified by chromatography on silica gel (EtOAc). The residue was suspended in 1,4-dioxane (4 mL) and 4N HCl/1,4-dioxane (4 mL) was added. The reaction mixture was stirred overnight, then at 50° C. for 2 h. The reaction mixture was concentrated by rotary evaporation, then ice-water was added. The mixture was basified using 1N aqueous NaOH solution, then extracted using EtOAc. The organic extract was washed with brine and dried (MgSO$_4$), then concentrated and purified by chromatography on silica gel (EtOAc-hexane, 3:1). The residue was crystallised from diethyl ether and filtered, then washed with diethyl ether and dried, to give the title compound (60 mg, 5%) as an off-white solid. $\delta_H$ (400 MHz, DMSO-$d_6$) 7.99 (t, J 1.3 Hz, 1H), 7.50 (m, 1H), 7.41 (m, 1H), 7.38 (m, 2H), 7.30 (m, 1H), 7.01 (d, J7.5 Hz, 1H), 6.77 (s, 1H), 5.25 (m, 1H), 5.13 (m, 1H), 2.21 (s, 3H). LCMS m/z 377 [M+H]$^+$.

Example 27

6-Iodo-2-methyl-3-{spiro[1H-isobenzofuran-3,1'-cyclopropane]-1-yl}imidazo[1,2-a]-pyridine n-Butyllithium solution in hexanes (2.5M, 4.5 mL, 11.25 mmol) was added at −78° C. to a solution of 1-phenylcyclopropanol (0.6 g, 4.48 mmol) in anhydrous toluene (8 mL) and stirred overnight, allowing the temperature to rise slowly. The reaction mixture was cooled to −78° C. again and a solution of Intermediate 30 (1 g, 3.5 mmol) in toluene (8 mL) was added gradually and left stirring for 6 h. The reaction mixture was poured into ice/saturated aqueous NH$_4$Cl solution, then extracted using EtOAc. The organic extract was dried (MgSO$_4$) and concentrated. The crude residue was dissolved in 1,4-dioxane (8 mL) and 4N HCl/1,4-dioxane (6 mL) was added. The solution was stirred overnight, then at 50° C. for 2 h. The reaction mixture was concentrated by rotary evaporation, then ice/saturated aqueous NH$_4$Cl solution was added and the residue was extracted using EtOAc. The organic extract was washed with brine, dried and concentrated. The crude residue was purified by chromatography on silica gel (EtOAc-hexane; 2:1, then 5:2). The material was further purified by HPLC to give the title compound (3 mg, 0.2%) as an off-white solid. $\delta_H$ (400 MHz, DMSO-$d_6$) 8.16 (s, 1H), 7.38 (m, 3H), 7.28 (m, 1H), 7.14 (m, 1H), 7.02 (m, 1H), 6.94 (s, 1H), 2.31 (s, 3H), 1.39 (m, 1H), 1.25 (m, 2H), 1.10 (m, 1H). LCMS m/z 403 [M+H]$^+$.

Example 28

6-Iodo-2-methyl-3-(3-methyl-1,3-dihydroisobenzofuran-1-yl)imidazo[1,2-a]pyridine Intermediate 31 (1.3 g, 2.62 mmol) was dissolved in 1,4-dioxane (80 mL) and water (4 mL) was added. HCl (25 mL, 4N in 1,4-dioxane) was added and the resulting mixture was stirred at room temperature for 18 h. The crude mixture was concentrated in vacuo and the residue was partitioned between EtOAc and saturated aqueous NaHCO$_3$ solution. The layers were separated and the aqueous phase was extracted twice with EtOAc. The combined organic layers were washed with brine, dried over Na$_2$SO$_4$ and concentrated in vacuo. The residue was purified by chromatography on silica gel (80% EtOAc in heptane) to give the title compound (640 mg, 59%) as a light yellow solid. $\delta_H$ (300 MHz, DMSO-$d_6$; 1:1 mixture of diastereomers) 8.12-8.07 (m, 1H), 7.97 (s, 1H), 7.50-7.26 (m, 10H), 7.06 (d, J7.5 Hz, 1H), 6.94 (d, J7.5 Hz, 1H), 6.86 (d, J2.4 Hz, 1H), 6.68 (d, J2.6 Hz, 1H), 5.55-5.45 (m, 1H), 5.39-5.29 (m, 1H), 2.30 (s, 3H), 2.13 (s, 3H), 1.58 (d, J6.3 Hz, 3H), 1.50 (d, J6.3 Hz, 3H). LCMS m/z 391.0 [M+H]$^+$.

Examples 29 & 30

The following compounds were prepared by a method analogous to that used to prepare Example 11, by reaction of the appropriate starting materials, in the presence of pyridinium p-toluenesulfonate in MeCN.

| Example | Name | Starting materials | m/z |
|---|---|---|---|
| 29 | 6-Iodo-2-methyl-3-[(3R)-3-methyl-1,3-dihydro-isobenzofuran-1-yl]imidazo[1,2-a]pyridine | Intermediate 29 and Intermediate 4 | 391 |
| 30 | 6-Iodo-2-methyl-3-[(3S)-3-methyl-1,3-dihydro-isobenzofuran-1-yl]imidazo[1,2-a]pyridine | Intermediate 29 and Intermediate 38 | 391 |

Example 31

6-Iodo-2-methyl-3-[3-(trifluoromethyl)-1,3-dihydroisobenzofuran-1-yl]imidazo[1,2-a]-pyridine To a solution of Intermediate 35 (0.052 g, 0.095 mmol) in 1,4-dioxane (1 mL) was added HCl (4M aqueous, 1 mL, 4 mmol) and the mixture was stirred at room temperature. Extra HCl (4M aqueous, 0.25 mL, 1 mmol) was added and stirring was continued overnight. The reaction mixture was quenched by the addition of saturated aqueous $Na_2CO_3$ solution and the organic layer was extracted into EtOAc (two portions of 10 mL). The combined organic layers were washed with water (10 mL) and brine (10 mL), then dried ($Na_2CO_3$) and filtered. The solvent was removed in vacuo. The resulting crude brown oil was purified by preparative HPLC to give the title compound (4 mg, 9%) as a mixture of diastereoisomers. $\delta_H$ (300 MHz, DMSO-$d_6$) 8.13 (m, 1H), 7.49 (m, 5H), 7.18 (m, 1H), 7.04 (dd, 1H, J 18.7, 2.2 Hz), 6.19 (m, 0.39H), 5.92 (m, 0.54H), 2.12 (m, 3H). LCMS m/z 445.6 $[M+H]^+$.

Examples 32 & 33

The following compounds were prepared by a method analogous to that used to prepare Example 1, by catalytic coupling of the appropriate starting material with a suitable boronic acid or pinacol boronate. Where applicable, chiral HPLC was used to separate isomers.

| Example | Name | Starting materials | m/z |
|---|---|---|---|
| 32 | 1-{5-[2-Methyl-3-(3-methyl-1,3-dihydro-isobenzofuran-1-yl)imidazo[1,2-a]pyridin-6-yl]-pyrimidin-2-yl}-1,4-diazepan-5-one | Example 28 and Intermediate 25 | 455 |
| 33 | Ethyl 4-methyl-1-{5-[2-methyl-3-(3-methyl-1,3-dihydroisobenzofuran-1-yl)imidazo[1,2-a]pyridin-6-yl]pyrimidin-2-yl}piperidine-4-carboxylate | Example 28 and Intermediate 26 | 512 |

Example 34

4-Methyl-1-{5-[2-methyl-3-(3-methyl-1,3-dihydroisobenzofuran-1-yl)imidazo[1,2-a]-pyridin-6-yl]pyrimidin-2-yl}piperidine-4-carboxylic acid Example 33 (120 mg, 0.235 mmol) was dissolved in THF (6 mL) and aqueous NaOH solution (6 mL, 1M) was added. The mixture was diluted with MeOH (6 mL) and stirred at room temperature overnight. After concentration under vacuum, the residue was taken up in water (6 mL) and acidified with aqueous HCl (1M) until solids precipitated from the solution. The solid was collected by filtration and air-dried for 2 h to give the title compound (101 mg, 89%) as a light-brown solid. $\delta_H$ (300 MHz, DMSO-$d_6$; ~1:1 mixture of diastereomers) 12.45 (s, 2H), 8.53 (s, 2H), 8.42 (s, 2H), 8.20 (s, 1H), 8.07 (s, 1H), 7.79-7.70 (m, 4H), 7.53-7.42 (m, 4H), 7.37-7.27 (m, 2H), 7.14 (d, J7.6 Hz, 1H), 7.03 (d, J7.5 Hz, 1H), 7.00 (s, 1H), 6.82 (s, 1H), 5.66-5.54 (m, 1H), 5.42-5.30 (m, 1H), 4.31-4.18 (m, 4H), 3.40-3.23 (m, 3H), 2.29 (s, 3H), 2.18 (s, 3H), 2.06-1.93 (m, 4H), 1.57 (d, J6.3 Hz, 3H), 1.51 (d, J6.3 Hz, 3H), 1.45-1.30 (m, 5H), 1.18 (m, 6H). LCMS m/z 484 $[M+H]^+$.

Example 35

6-Bromo-3-(7-methoxy-3-methyl-1,3-dihydroisobenzofuran-1-yl)-2-methylimidazo[1,2-a]pyridine Prepared from Intermediate 32 by a method analogous to that used to prepare Example 31, to give the title compound (15 mg, 90%) as a clear oil. $\delta_H$ (400 MHz, CDCl$_3$) 7.93 (d, 1H, J 1.2 Hz), 7.88 (s, OH), 7.38 (m, 4H), 7.15 (ddd, 2H, J9.4, 5.7, 1.8 Hz), 6.90 (d, 2H, J7.5 Hz), 6.75 (dd, 2H, J8.1, 4.1 Hz), 6.69 (d, 1H, J2.8 Hz), 6.56 (d, 1H, J2.7 Hz), 5.55 (qd, 1H, J6.3, 2.8 Hz), 5.37 (qd, 1H, J6.4, 2.7 Hz), 3.63 (s, 3H), 3.53 (s, 3H), 2.39 (s, 3H), 2.25 (s, 3H), 1.64 (d, 3H, J6.4 Hz), 1.56 (d, 3H, J6.4 Hz). LCMS m/z 375 [M+H]+.

Example 36

3-(6-Bromo-2-methylimidazo[1,2-a]pyridin-3-yl)isoindolin-1-one 4-toluenesulfonic acid salt Intermediate 36 (53 mg, 0.35 mmol) and Intermediate 12 (50 mg, 0.24 mmol) were suspended in acetonitrile (5 mL). Pyridinium p-toluenesulfonate (0.24 g, 0.94 mmol) was added and the reaction mixture was heated at 80° C. overnight. The precipitate which formed on cooling to room temperature was filtered and dried, to afford the title compound (60 mg, 49%) as a white solid. $\delta_H$ (300 MHz, DMSO-$d_6$) 8.97 (s, 1H), 7.87-7.83 (m, 3H), 7.69-7.60 (m, 2H), 7.51-7.45 (m, 3H), 7.12-7.09 (m, 2H), 6.61 (s, 1H), 2.28 (s, 3H), 1.99 (br s, 3H). LCMS m/z 346 $[M+H]^+$.

Example 37

3-(6-Bromo-2-methylimidazo[1,2-a]pyridin-3-yl)-2-methylisoindolin-1-one

Intermediate 37 (460 mg, 2.84 mmol) and Intermediate 12 (300 mg, 1.42 mmol) were suspended in acetonitrile (30 mL). Pyridinium p-toluenesulfonate (1.42 g, 5.68 mmol) was added and the reaction mixture was heated at 80° C. overnight. The cooled reaction mixture was diluted with EtOAc and washed with saturated aqueous sodium bicarbonate solution. The organic extracts were dried over sodium sulphate and concentrated under reduced pressure. The residue was purified by chromatography on silica gel (EtOAc:DCM 0-80%) to afford the title compound (344 mg, 68%) as a white solid, as a 1:1 mixture of atropisomers. $\delta_H$ (300 MHz, DMSO-$d_6$) 9.30 (m, 1H), 7.93-7.90 (m, 1H), 7.79-7.77 (m, 1H), 7.64-7.50 (m, 6H), 7.42-7.38 (m, 2H), 7.33-7.27 (m, 2H), 6.70 (dd, J 1.9, 0.8 Hz, 1H), 6.57 (s, 1H), 6.36 (s, 1H), 2.81 (s, 3H), 2.80 (s, 3H), 2.62 (s, 3H), 1.53 (s, 3H). LCMS m/z 356 [M+H]$^+$.

Example 38

3-{6-[2-(1-Hydroxy-1-methylethyl)pyrimidin-5-yl]-2-methylimidazo[1,2-a]pyridin-3-yl}-2-methylisoindolin-1-one Prepared from Example 37 and 2-[5-(4,4,5,5-tetramethyl-1,3,2-dioxaborolan-2-yl)pyrimidin-2-yl]propan-2-ol by a method analogous to that used to prepare Example 1, to afford the title compound (50 mg, 38%) as an off-white solid, as a 1:1 mixture of atropisomers. $\delta_H$ (300 MHz, DMSO-$d_6$) 9.44 (s, 0.5H), 9.28 (s, 1H), 8.51 (s, 1H), 7.95-7.93 (m, 0.5H), 7.82-7.76 (m, 1H), 7.72-7.56 (m, 3.5H), 7.45-7.35 (m, 1H), 6.91 (dd, J 1.7, 1.0 Hz, 0.5H), 6.68 (s, 0.5H), 6.43 (s, 0.5H), 5.14 (s, 0.5H), 5.10 (s, 0.5H), 2.85 (s, 1.5H), 2.85 (s, 1.5H), 2.67 (s, 1.5H), 1.60 (s, 1.5H), 1.56 (s, 3H), 1.48 (s, 3H). LCMS m/z 414 [M+H]$^+$.

Example 39

6-Bromo-2-methyl-3-[(1R,3R)-3-methylisoindolin-1-yl]imidazo[1,2-a]pyridine and 6-Bromo-2-methyl-3-[(1S,3S)-3-methylisoindolin-1-yl]imidazo[1,2-a]pyridine Intermediate 45 (20 mg, 0.045 mmol) was dissolved in DCM:TFA (1:1, 1 mL) and stirred at room temperature for 3 h. The reaction mixture was concentrated under reduced pressure to afford the title compound (20.6 mg, 99%), trifluoroacetate salt, as a white solid. $\delta_H$ (300 MHz, DMSO-$d_6$) 10.00 (br s, 1H), 9.29 (br s, 1H), 8.91 (s, 1H), 7.57-7.49 (m, 4H), 7.40 (br s, 1H), 7.24 (br s, 1H), 6.78 (br s, 1H), 4.98 (br s, 1H), 1.67 (br s, 3H), 1.57 (d, J 6.4 Hz, 3H). LCMS m/z 344 [M+H]$^+$.

Example 40

6-Bromo-2-methyl-3-[(1R,3S)-3-methylisoindolin-1-yl]imidazo[1,2-a]pyridine and 6-Bromo-2-methyl-3-[(1S,3R)-3-methylisoindolin-1-yl]imidazo[1,2-a]pyridine Intermediate 46 (20 mg, 0.045 mmol) was dissolved in DCM:TFA (1:1, 1 mL) and stirred at room temperature for 3 h. The reaction mixture was concentrated under reduced pressure to afford the title compound (19.6 mg, 95%), trifluoroacetate salt, as a white solid. $\delta_H$ (300 MHz, DMSO-$d_6$) 9.85 (br s, 2H), 9.08 (br s, 1H), 7.69-7.62 (m, 4H), 7.54 (br s, 1H), 7.41 (br s, 1H), 6.99 (s, 1H), 5.14 (br s, 1H), 1.72 (d, J 6.8 Hz, 6H). LCMS m/z 344 [M+H]+.

Example 41

2-(5-{2-Methyl-3-[(1R,3R)-3-methylisoindolin-1-yl]imidazo[1,2-a]pyridin-6-yl}-pyrimidin-2-yl)propan-2-ol and 2-(5-{2-Methyl-3-[(1S,3S)-3-methylisoindolin-1-yl]-imidazo[1,2-a]pyridin-6-yl}pyrimidin-2-yl)propan-2-ol Prepared from Intermediate 45 and 2-(1-hydroxy-1-methylethyl)pyrimidine-5-boronic acid pinacol ester by a method analogous to that used to prepare Example 1, followed by deprotection using a method analogous to that used to prepare Example 39, to afford the title compound (4 mg, 26%) as an off-white solid. $\delta_H$ (400 MHz, DMSO-$d_6$) 8.77 (s, 2H), 8.37 (s, 1H), 7.64-7.57 (m, 2H), 7.41 (d, J7.4 Hz, 1H), 7.34 (t, J7.3 Hz, 1H), 7.18 (t, J7.4 Hz, 1H), 6.78 (d, J7.4 Hz, 1H), 6.07 (d, J2.5 Hz, 1H), 5.10 (s, 1H), 4.58 (m, 1H), 2.39 (s, 3H), 1.50 (s, 6H), 1.48 (d, J6.3 Hz, 3H). LCMS m/z 400 [M+H]$^+$.

Example 42

2-(5-{2-Methyl-3-[(1R,3S)-3-methylisoindolin-1-yl]imidazo[1,2-a]pyridin-6-yl}-pyrimidin-2-yl)propan-2-ol and 2-(5-{2-Methyl-3-[(1S,3R)-3-methylisoindolin-1-yl]-imidazo[1,2-a]pyridin-6-yl}pyrimidin-2-yl)propan-2-ol Prepared from Intermediate 46 and 2-(1-hydroxy-1-methylethyl)pyrimidine-5-boronic acid pinacol ester by a method analogous to that used to prepare Example 1, followed by deprotection using a method analogous to that used to prepare Example 39, to afford the title compound (11 mg, 28%) as an off-white solid. $\delta_H$ (400 MHz, DMSO-$d_6$) 8.88 (s, 2H), 8.31 (s, 1H), 7.60 (s, 2H), 7.49-7.30 (m, 3H), 7.21 (td, J7.4, 0.8 Hz, 1H), 6.97 (d, J7.4 Hz, 1H), 6.22 (s, 1H), 5.10 (s, 1H), 4.63 (m, 1H), 2.17 (s, 3H), 1.51 (s, 6H), 1.40 (d, J 6.5 Hz, 3H). LCMS m/z 400 [M+H]$^+$.

Example 43

3-{7-Fluoro-6-[4-(methanesulfonyl)phenyl]-2-methylimidazo[1,2-a]pyridin-3-yl}-1,3-dihydro-2-benzofuran-1-one A solution of Intermediate 47 (1 g, 3.29 mmol) and methyl 2-formylbenzoate (0.85 g, 5.18 mmol) in 1,4-dioxane (5 mL) was placed in a sealed vessel and heated, with stirring, at 80° C. for 66 h. The reaction mixture was concentrated under vacuum. The resulting brown solid was washed with DCM and dried in air to give the title compound (172 mg, 12%) as a white solid. $\delta_H$ (CDCl$_3$) 8.66 (s, 1H), 8.07 (d, J 8.2 Hz, 2H), 8.01 (d, J7.6 Hz, 1H), 7.85 (dd, J 16.7, 7.6 Hz, 3H), 7.75 (t, J7.4 Hz, 1H), 7.68-7.62 (m, 2H), 7.57 (s, 1H), 3.29 (s, 3H), 1.79 (s, 3H).

Example 44 trans-4-(5-{2-Methyl-3-[(1S,3S)-3-methyl-1,3-dihydro-2-benzofuran-1-yl]imidazo[1,2-a]pyridin-6-yl}pyrimidin-2-yl)cyclohexanecarboxylic acid A racemic mixture (3:7 trans:cis by LCMS) of Intermediate 49 (515 mg, 1.04 mmol) was dissolved in ethanol (10 mL) and degassed with N$_2$. A solution of sodium ethanolate in ethanol (2M, 2.59 mL) was added and the mixture was stirred at 80° C. for 24 h. The reaction mixture was concentrated in vacuo and purified using preparative HPLC (Method C) to afford the title compound (258.8 mg, 51%) as a light brown solid. $\delta_H$ (400 MHz, DMSO-$d_6$) 8.77 (s, 2H), 8.15 (s, 1H), 7.65 (s, 2H), 7.45 (dt, J 14.8, 7.5 Hz, 2H), 7.30 (t, J7.3 Hz, 1H), 6.98 (d, J7.6 Hz, 1H), 6.80 (d, J2.3 Hz, 1H), 5.34 (dd, J6.3, 2.5 Hz, 1H), 2.73 (t, J 12.0 Hz, 1H), 2.23 (s, 3H), 1.92 (d, J 12.0 Hz, 4H), 1.80 (t, J 12.0 Hz, 1H), 1.56 (d, J6.3 Hz, 3H), 1.51 (t, J 11.4 Hz, 2H), 1.40-1.30 (m, 2H). Method D HPLC-MS: MH$^+$ m/z 470.2, RT 1.89 minutes (100%).

Example 45

{6-Bromo-3-[(3S)-3-methyl-1,3-dihydroisobenzo-furan-1-yl]imidazo[1,2-a]pyridin-2-yl}-methanol Intermediate 38 (66.1 mg, 0.44 mmol) and (6-bromoimidazo[1,2-a]pyridin-2-yl)-methanol (100 mg, 0.44 mmol) were dissolved in acetonitrile (10 mL) and pyridinium p-toluenesulfonate (443 mg, 1.76 mmol) was added. The resulting mixture was heated at 80° C. overnight. The resulting mixture was cooled and evaporated onto silica. Purification by column chromatography (0-15% MeOH in DCM) gave a clear oil, which was freeze-dried to give the title compound (50 mg, 32%), 7:3 mixture of diastereomers, as a white solid.

Major diastereomer (trans): $\delta_H$ (400 MHz, DMSO-$d_6$) 7.80 (dd, 1H, J0.6, 1.9 Hz), 7.57 (dd, 1H, J0.6, 8.8 Hz), 7.48 (m, 1H), 7.42 (m, 1H), 7.36 (dd, 1H, J9.5, 1.9 Hz), 7.29 (t, 1H, J7.3 Hz), 7.04 (d, 1H, J7.4 Hz), 6.97 (d, 1H, J2.5 Hz), 5.63 (qd, 1H, J6.3, 2.6 Hz), 5.22 (t, 1H, J5.7 Hz), 4.54 (m, 2H), 1.52 (d, 3H, J6.3 Hz.

Minor diastereomer (cis): $\delta_H$ (400 MHz, DMSO-$d_6$) 7.78 (m, 1H), 7.57 (m, 1H), 7.48 (m, 1H), 7.42 (m, 1H), 7.36 (dd, 1H, J9.5, 1.9 Hz), 7.30 (t, 1H, J7.3 Hz), 6.92 (m, 1H), 6.82 (d, 1H, J2.8 Hz), 5.40 (m, 1H), 5.28 (t, 1H, J5.7 Hz), 4.66 (d, 2H, J5.6 Hz), 1.66 (d, 3H, J6.4 Hz).

LCMS MH+ m/z 359.60.

Example 46

Methyl (1R,5S)-3-(5-{2-(hydroxymethyl)-3-[(1R,3S)-3-methyl-1,3-dihydroisobenzofuran-1-yl]imidazo[1,2-a]pyridin-6-yl}pyrimidin-2-yl)-3-azabicyclo[3.2.1]octane-8-carboxylate and Methyl (1R,5S)-3-(5-{2-(hydroxymethyl)-3-[(1S,3R)-3-methyl-1,3-dihydroisobenzofuran-1-yl]imidazo[1,2-a]pyridin-6-yl}pyrimidin-2-yl)-3-azabicyclo[3.2.1]-octane-8-carboxylate Prepared from Example 45 and Intermediate 24 by a method analogous to that used to prepare Example 1 to afford the title compound (652 mg, 45%), 2:1 trans:cis mixture of diastereoisomers, as a white solid. Major diastereomer (trans): $\delta_H$ (400 MHz, DMSO-$d_6$) 8.36 (s, 2H), 7.65-7.53 (m, 3H), 7.43 (t, 1H, J7.7 Hz), 7.28 (t, 1H, J7.7 Hz), 7.03 (m, 2H), 5.76 (s, 1H), 5.69 (qd, 1H, J6.3, 2.5 Hz), 5.21 (t, 1H, J5.9 Hz), 4.59 (d, 2H, J5.6 Hz), 4.38 (m, 2H), 3.63 (s, 3H), 3.02 (d, 2H, J 12.4 Hz), 2.78 (s, 1H), 2.61 (d, 2H, J0.5 Hz), 1.67 (m, 2H), 1.51 (d, 3H, J6.3 Hz), 1.38 (m, 2H). LCMS MH+m/z 526.80.

Example 47

(1R,5S)-3-(5-{2-(Hydroxymethyl)-3-[(1R,3S)-3-methyl-1,3-dihydroisobenzofuran-1-yl]-imidazo[1,2-a]pyridin-6-yl}pyrimidin-2-yl)-3-azabicyclo[3.2.1]octane-8-carboxylic acid and (1R,5S)-3-(5-{2-(Hydroxymethyl)-3-[(1S,3R)-3-methyl-1,3-dihydroisobenzofuran-1-yl]imidazo[1,2-a]pyridin-6-yl}pyrimidin-2-yl)-3-azabicyclo[3.2.1]octane-8-carboxylic acid Prepared from Example 46 by a method analogous to that used to prepare Example 20 to afford the title compound (240 mg, 41%), 2:1 trans:cis mixture of diastereoisomers, as an off-white solid. Major diastereomer (trans): $\delta_H$ (400 MHz, DMSO-$d_6$) 12.18 (s, 1H), 8.40 (s, 2H), 7.79 (m, 1H), 7.64 (m, 1H), 7.51 (d, 1H, J7.5 Hz), 7.42 (t, 1H, J7.3 Hz), 7.29 (t, 1H, J7.3 Hz), 7.05 (m, 2H), 5.76 (s, 1H), 5.69 (m, 1H), 5.37 (m, 1H), 4.57 (s, 2H), 4.40 (m, 2H), 3.02 (m, 2H), 2.67 (s, 1H), 2.61 (m, 2H), 1.70 (m, 2H), 1.52 (d, 3H, J6.3 Hz), 1.38 (m, 2H). LCMS MH+ m/z 512.80.

Examples 48 & 49

2-(5-{2-(Hydroxymethyl)-3-[(1R,3S)-3-methyl-1,3-dihydroisobenzofuran-1-yl]imidazo-[1,2-a]pyridin-6-yl}pyrimidin-2-yl)propan-2-ol and 2-(5-{2-(Hydroxymethyl)-3-[(1S,3S)-3-methyl-1,3-dihydroisobenzofuran-1-yl]imidazo[1,2-a]pyridin-6-yl}pyrimidin-2-yl)-propan-2-ol Prepared from Example 45 and 2-[5-(4,4,5,5-tetramethyl-1,3,2-dioxaborolan-2-yl)pyrimidin-2-yl]propan-2-ol by a method analogous to that used to prepare Example 1 to afford the title compounds (600 mg, 52%), 4:1 trans:cis mixture of diastereoisomers, as an off-white solid. The diastereoisomers were then separated by preparative HPLC.

Major diastereomer (trans): $\delta_H$ (400 MHz, DMSO-$d_6$) 8.86 (s, 2H), 8.02 (s, 1H), 7.78 (d, 1H, J9.3 Hz), 7.68 (dd, 1H, J9.3, 1.5 Hz), 7.50 (d, 1H, J7.5 Hz), 7.42 (t, 1H, J 7.4 Hz), 7.30 (t, 1H, J7.4 Hz), 7.09 (d, 1H, J7.8 Hz), 5.77 (m, 2H), 5.28 (s, 1H), 5.11 (m, 1H), 4.62 (s, 1H), 3.95 (s, 1H), 1.53 (m, 6H), 1.10 (s, 3H). LCMS MH+ m/z 417.80.

Minor diastereomer (cis): $\delta_H$ (400 MHz, DMSO-$d_6$) 8.51 (s, 2H), 7.65 (m, 2H), 7.27 (m, 4H), 7.00 (d, 1H, J7.5 Hz), 6.86 (d, 1H, J2.3 Hz), 5.56 (qd, 1H, J6.0, 2.2 Hz), 5.21 (s, 1H), 4.81 (m, 2H), 1.95 (s, 1H), 1.55 (s, 6H), 1.53 (s, 3H). LCMS MH+ m/z 417.80.

Example 50

{3-[(1R,3S)-3-Methyl-1,3-dihydroisobenzofuran-1-yl]-6-[2-(morpholin-4-yl)pyrimidin-5-yl]imidazo[1,2-a]pyridin-2-yl}methanol and {3-[(1S,3R)-3-Methyl-1,3-dihydroisobenzofuran-1-yl]-6-[2-(morpholin-4-yl)pyrimidin-5-yl]imidazo[1,2-a]pyridin-2-yl}-methanol Prepared from Example 45 and Intermediate 23 by a method analogous to that used to prepare Example 1 to afford the title compound (330 mg, 27%), approximately 4:1 mixture of diastereomers, as a white solid. Major diastereomer (trans): $\delta_H$ (400 MHz, DMSO-$d_6$) 8.43 (s, 2H), 7.72 (m, 1H), 7.63 (dd, 1H, J9.3, 0.9 Hz), 7.53 (dd, 1H, J9.4, 1.7 Hz), 7.47 (m, 1H), 7.39 (t, 1H, J7.3 Hz), 7.28 (t, 1H, J6.7 Hz), 7.03 (m, 2H), 5.69 (m, 1H), 5.18 (t, 1H, J5.8 Hz), 4.59 (d, 2H, J5.6 Hz), 3.70 (m, 8H), 1.51 (d, 3H, J6.3 Hz). LCMS MH+ m/z 444.80.

Example 51

4-(5-{2-Methyl-3-[(1 S,3S)-3-methyl-1,3-dihydroisobenzofuran-1-yl]imidazo[1,2-a]-pyridin-6-yl}pyrimidin-2-yl)piperazin-2-one Prepared from Example 11 and 2-(3-oxopiperazin-1-yl)pyrimidin-5-ylboronic acid by a method analogous to that used to prepare Example 1 to afford the title compound as a white solid. LCMS MH+ m/z 441.

Example 52

2-(5-{2-Methyl-3-[(3S)-3-methyl-1,3-dihydroisobenzofuran-1-yl]imidazo[1,2-a]pyrazin-6-yl}pyrimidin-2-yl)propan-2-ol Prepared from Intermediate 50 and 2-[5-(4,4,5,5-tetramethyl-1,3,2-dioxaborolan-2-yl)pyrimidin-2-yl]propan-2-ol by a method analogous to that used to prepare Example 1 to afford the title compound as a white solid. LCMS MH⁺ m/z 402.

Example 53

6-Bromo-3-(1,3-dihydroisobenzofuran-1-yl)-2-(methoxymethyl)imidazo[1,2-a]pyridine To a solution of Intermediate 52 (0.60 g, 1.3 mmol) in a mixture of DCM (15 mL) and $H_2O$ (33 mL) was added HCl (5 mL, 20 mmol). The mixture was stirred for 5 days, then partitioned between aqueous $NaHCO_3$ solution (100 mL) and EtOAc (100 mL). The organic phase was separated and washed with water (20 mL), then dried over $Na_2SO_4$, filtered and concentrated in vacuo. The residue was purified by chromatography on silica gel (0-10% hexane:EtOAc) to afford the title compound (310 mg, 66%) as a white solid. LCMS m/z 361 [M+H]⁺.

The invention claimed is:

1. A compound represented by formula (IIB-A), (IIB-B) or (IIB-C), or an N-oxide thereof, or a pharmaceutically acceptable salt or solvate thereof, or a co-crystal thereof:

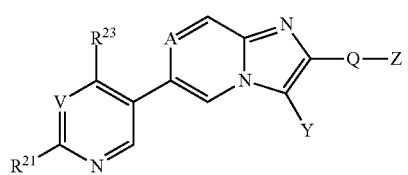
(IIB-A)

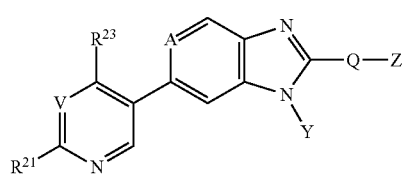
(IIB-B)

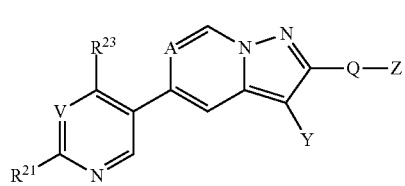
(IIB-C)

wherein
V represents C—$R^{22}$ or N;
$R^{21}$ represents hydroxy($C_{1-6}$)alkyl; or $R^{21}$ represents ($C_{3-7}$)cycloalkyl, ($C_{4-9}$)bicycloalkyl, ($C_{3-7}$)heterocycloalkyl or ($C_{4-9}$)heterobicycloalkyl, any of which groups is optionally substituted by one, two or three substituents independently selected from $C_{1-6}$ alkyl, oxo, carboxy and $C_{2-6}$ alkoxycarbonyl;
$R^{22}$ represents hydrogen, halogen or $C_{1-6}$ alkyl;
$R^{23}$ represents hydrogen, $C_{1-6}$ alkyl, trifluoromethyl or $C_{1-6}$ alkoxy;
A represents C—$R^2$ or N;
Y represents a group of formula (Ya):

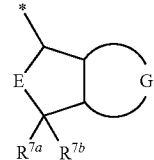
(Ya)

the asterisk (*) represents the point of attachment to the remainder of the molecule;
E represents —O—, —S—, —S(O)—, —S(O)$_2$—, —S(O)(N$R^5$)— or —N($R^5$)—;
G represents the residue of an optionally substituted benzene ring; or an optionally substituted five-membered heteroaromatic ring selected from furyl, thienyl, pyrrolyl, pyrazolyl, oxazolyl, isoxazolyl, thiazolyl, isothiazolyl, imidazolyl, oxadiazolyl, thiadiazolyl and triazolyl; or an optionally substituted six-membered heteroaromatic ring selected from pyridinyl, pyridazinyl, pyrimidinyl, pyrazinyl and triazinyl;
Q represents —$CH_2$—, —CH(OH)—, —$CH_2$O—, —$CH_2$S— or —$CH_2OCH_2$—;
Z represents hydrogen or methyl;
$R^2$ represents hydrogen or halogen;
$R^5$ represents hydrogen or $C_{1-6}$ alkyl;
$R^{7a}$ represents hydrogen, $C_{1-6}$ alkyl or trifluoromethyl; and
$R^{7b}$ represents hydrogen or $C_{1-6}$ alkyl; or
$R^{7a}$ and $R^{7b}$, when taken together with the carbon atom to which they are both attached, represent carbonyl (C=O); or
$R^{7a}$ and $R^{7b}$, when taken together with the carbon atom to which they are both attached, represent $C_{3-7}$ cycloalkyl or $C_{3-7}$ heterocycloalkyl, either of which groups may be optionally substituted by one or more substituents.

2. The compound as claimed in claim 1 wherein $R^{21}$ represents hydroxy($C_{1-6}$)alkyl.

3. A compound as claimed in claim 1 represented by formula (IIC-A), (IID-A), (IIE-A), (IIF-A), (IIG-A), (IIH-A), (IIJ-A), (IIK-A), (IIL-A), (IIC-B), (IID-B), (IIE-B), (IIF-B), (IIG-B), (IIH-B), (IIJ-B), (IIK-B), (IIL-B), (IIC-C), (IID-C), (IIE-C), (IIG-C), (IIH-C), (IIH-C), (IIJ-C), (IIK-C) or (IIL-C), or an N-oxide thereof, or a pharmaceutically acceptable salt or solvate thereof, or a co-crystal thereof:

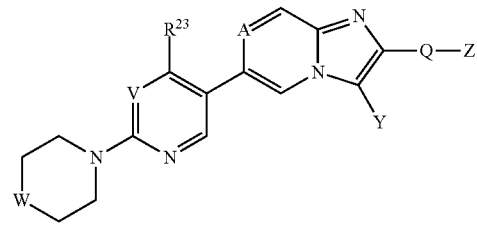
(IIC-A)

-continued
(IIE-A)
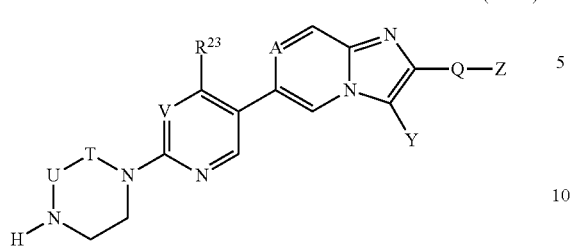
(IIC-B)
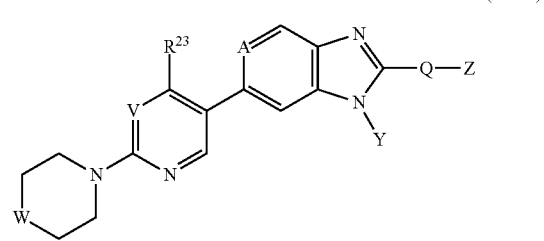
(IIF-A)
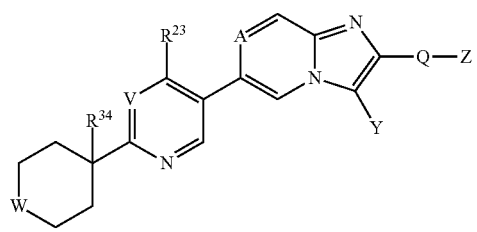
(IIE-B)
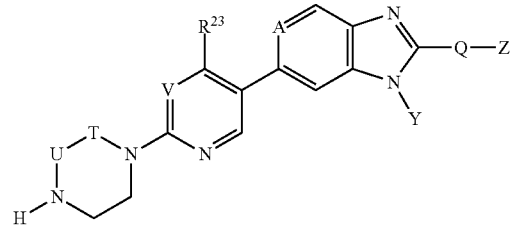
(IIG-A)
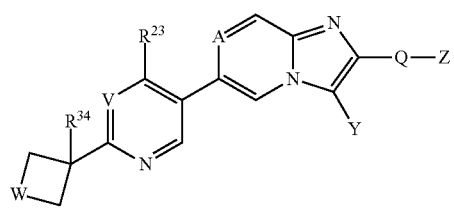
(IIF-B)
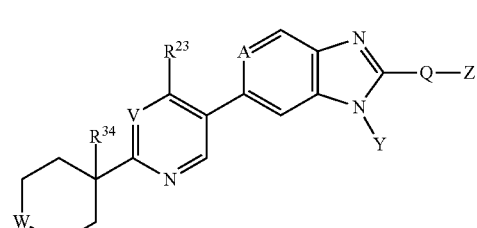
(IIH-A)
(IIG-B)
(IIK-A)
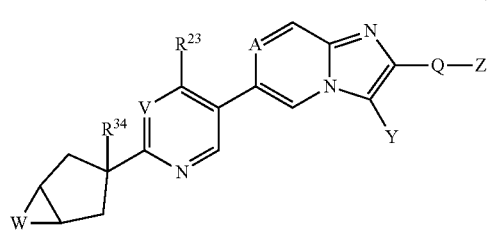
(IIH-B)
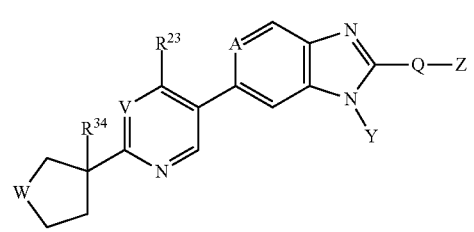
(IIL-A)
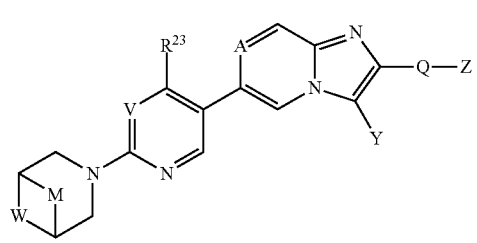
(IIK-B)

-continued (IIL-B)
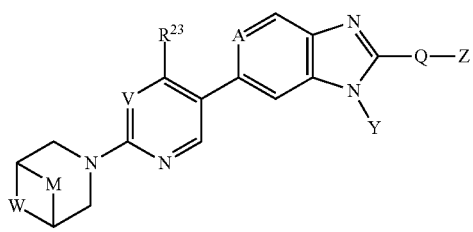

(IIC-C)
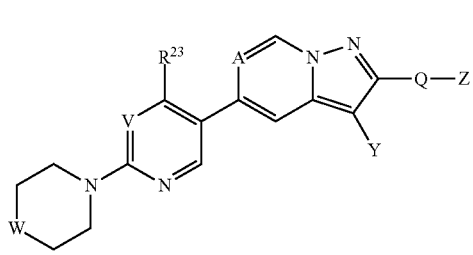

(IIE-C)
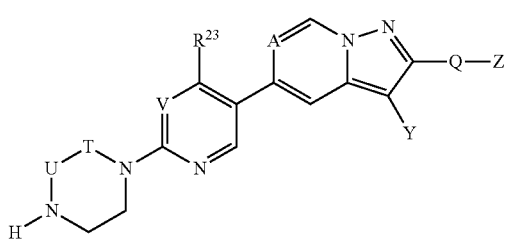

(IIF-C)
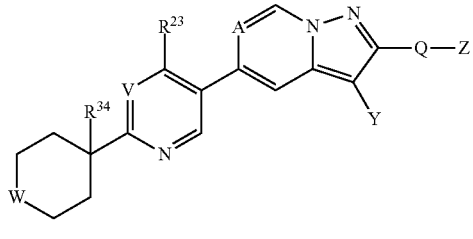

(IIG-C)
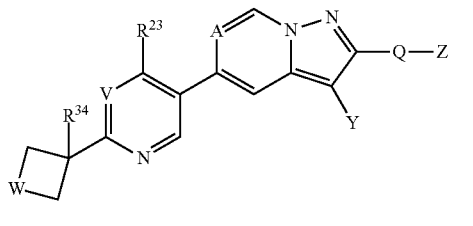

(IIH-C)
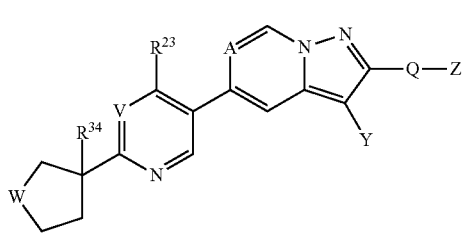

-continued (IIK-C)
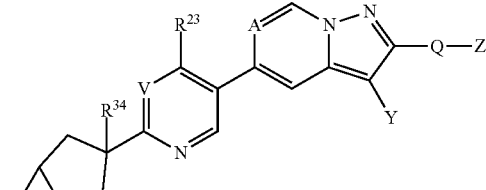

(IIL-C)
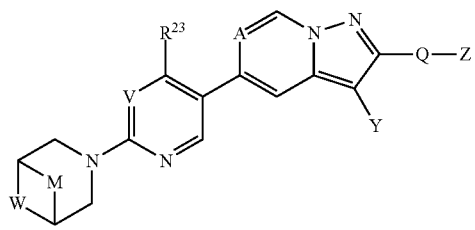

wherein
T represents —CH$_2$— or —CH$_2$CH$_2$—;
U represents C(O) or S(O)$_2$;
W represents O, N(R$^{31}$) or C(R$^{32}$)(R$^{33}$);
-M- represents —CH$_2$— or —CH$_2$CH$_2$—;
R$^{31}$ represents hydrogen, C$_{1-6}$ alkyl, carboxy or C$_{2-6}$ alkoxycarbonyl;
R$^{32}$ represents carboxy or C$_{2-6}$ alkoxycarbonyl;
R$^{33}$ represents hydrogen or C$_{1-6}$ alkyl;
R$^{34}$ represents hydrogen.

4. The compound as claimed in claim 1 wherein Y represents a group of formula (Ya-1) or (Ya-2):

(Ya-1)
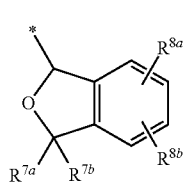

(Ya-2)
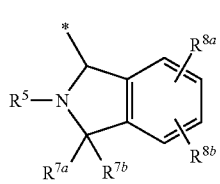

wherein
the asterisk (*) represents the point of attachment to the remainder of the molecule; and
R$^{8a}$ and R$^{8b}$ independently represent C$_{1-6}$ alkyl, halogen, cyano, trifluoromethyl, hydroxy, C$_{1-6}$ alkoxy, difluoromethoxy, C$_{1-6}$ alkylthio, C$_{1-6}$ alkylsulphinyl, C$_{1-6}$ alkylsulphonyl, C$_{2-6}$ alkylcarbonyl, amino, C$_{1-6}$ alkylamino or di(C$_{1-6}$)alkylamino.

5. A compound that is,
2-{5-[7-Fluoro-2-methyl-3-(3H-spiro[2-benzofuran-1,1'-cyclopropan]-3-yl)imidazo[1,2-a]pyridin-6-yl]pyrimidin-2-yl}propan-2-ol;
2-(5-{3-[(1S,3R)-3-Ethyl-1,3-dihydroisobenzofuran-1-yl]-7-fluoro-2-methylimidazo[1,2-a]pyridin-6-yl}pyrimidin-2-yl)propan-2-ol;

2-(5-{3-[(1S,3S)-3-Ethyl-1,3-dihydroisobenzofuran-1-yl]-7-fluoro-2-methylimidazo[1,2-a]pyridin-6-yl}pyrimidin-2-yl)propan-2-ol;
2-(5-{7-Fluoro-2-methyl-3-[(3R)-3-methyl-1,3-dihydro-2-benzofuran-1-yl]imidazo[1,2-a]pyridin-6-yl}pyrimidin-2-yl)propan-2-ol;
Potassium (1R,5S,6R)-3-(5-{2-methyl-3-[(1S,3S)-3-methyl-1,3-dihydro-2-benzofuran-1-yl]imidazo[1,2-a]pyridin-6-yl}pyrimidin-2-yl)bicyclo[3.1.0]hexane-6-carboxylate;
2-Methyl-3-[(1S,3S)-3-methyl-1,3-dihydro-2-benzofuran-1-yl]-6-[2-(piperazin-1-yl)-pyrimidin-5-yl]imidazo[1,2-a]pyridine;
2-(5-{2-Methyl-3-[(1S,3S)-3-methyl-1,3-dihydro-2-benzofuran-1-yl]imidazo[1,2-a]-pyridin-6-yl}pyridin-2-yl)propan-2-ol;
2-Methyl-3-[(1S,3S)-3-methyl-1,3-dihydro-2-benzofuran-1-yl]-6-[6-(piperazin-1-yl)-pyridin-3-yl]imidazo[1,2-a]pyridine;
2-Methyl-3-[(1S,3S)-3-methyl-1,3-dihydro-2-benzofuran-1-yl]-6-[2-(morpholin-4-yl)-pyridin-5-yl]imidazo[1,2-a]pyridine;
2-(5-{2-Methyl-3-[(1S,3S)-3-methyl-1,3-dihydro-2-benzofuran-1-yl]imidazo[1,2-a]pyridin-6-yl}-pyrimidin-2-yl)propan-2-ol;
2-(5-{2-Methyl-3-[(1R,3S)-3-methyl-1,3-dihydro-2-benzofuran-1-yl]imidazo[1,2-a]pyridin-6-yl}-pyrimidin-2-yl)propan-2-ol;
Methyl (1R,5S)-3-(5-{2-methyl-3-[(3S)-3-methyl-1,3-dihydroisobenzofuran-1-yl]imidazo[1,2-a]pyridin-2-yl}-3-azabicyclo[3.2.1]-octane-8-carboxylate;
(1R,5S)-3-(5-{2-Methyl-3-[(3S)-3-methyl-1,3-dihydroisobenzofuran-1-yl]imidazo[1,2-a]-pyridin-6-yl}pyrimidin-2-yl)-3-azabicyclo[3.2.1]octane-8-carboxylic acid;
(1R,5S)-3-(5-{2-Methyl-3-[(1S,3S)-3-methyl-1,3-dihydroisobenzofuran-1-yl]imidazo[1,2-a]pyridin-6-yl}pyrimidin-2-yl)-3-azabicyclo[3.2.1]octane-8-carboxylic acid;
(1R,5S)-3-(5-{2-Methyl-3-[(1R,3S)-3-methyl-1,3-dihydroisobenzofuran-1-yl]imidazo[1,2-a]pyridin-6-yl}pyrimidin-2-yl)-3-azabicyclo[3.2.1]octane-8-carboxylic acid;
2-(5-{7-Fluoro-2-methyl-3-[(3S)-3-methyl-1,3-dihydroisobenzofuran-1-yl]imidazo[1,2-a]pyridin-6-yl}pyrimidin-2-yl)propan-2-ol;
1-{5-[2-Methyl-3-(3-methyl-1,3-dihydro-isobenzofuran-1-yl)imidazo[1,2-a]pyridin-6-yl]-pyrimidin-2-yl}-1,4-diazepan-5-one;
Ethyl 4-methyl-1-{5-[2-methyl-3-(3-methyl-1,3-dihydroisobenzofuran-1-yl)imidazo[1,2-a]pyridin-6-yl]pyrimidin-2-yl}piperidine-4-carboxylate;
4-Methyl-1-{5-[2-methyl-3-(3-methyl-1,3-dihydroisobenzofuran-1-yl)imidazo[1,2-a]pyridin-6-yl]pyrimidin-2-yl}piperidine-4-carboxylic acid;
3-{6-[2-(1-Hydroxy-1-methylethyl)pyrimidin-5-yl]-2-methylimidazo[1,2-a]pyridin-3-yl}-2-methylisoindolin-1-one;
2-(5-{2-Methyl-3-[(1R,3R)-3-methylisoindolin-1-yl]imidazo[1,2-a]pyridin-6-yl}-pyrimidin-2-yl)propan-2-ol2-(5-{2-Methyl-3-[(1S,3S)-3-methylisoindolin-1-yl]-imidazo[1,2-a]pyridin-6-yl}pyrimidin-2-yl)propan-2-ol;
2-(5-{2-Methyl-3-[(1R,3S)-3-methylisoindolin-1-yl]imidazo[1,2-a]pyridin-6-yl}-pyrimidin-2-yl)propan-2-ol2-(5-{2-Methyl-3-[(1S,3R)-3-methylisoindolin-1-yl]-imidazo[1,2-a]pyridin-6-yl}pyrimidin-2-yl)propan-2-ol;
trans-4-(5-{2-Methyl-3-[(1S,3S)-3-methyl-1,3-dihydro-2-benzofuran-1-yl]imidazo[1,2-a]pyridin-6-yl}pyrimidin-2-yl)cyclohexanecarboxylic acid;
Methyl (1R,5S)-3-(5-{2-(hydroxymethyl)-3-[(1R,3S)-3-methyl-1,3-dihydroisobenzofuran-1-yl]imidazo[1,2-a]pyridin-6-yl}pyrimidin-2-yl)-3-azabicyclo[3.2.1]octane-8-carboxylate;
Methyl (1R,5S)-3-(5-{2-(hydroxymethyl)-3-[(1S,3R)-3-methyl-1,3-dihydro-isobenzofuran-1-yl]imidazo[1,2-a]pyridin-6-yl}pyrimidin-2-yl)-3-azabicyclo[3.2.1]-octane-8-carboxylate;
(1R,5S)-3-(5-{2-(Hydroxymethyl)-3-[(1R,3S)-3-methyl-1,3-dihydroisobenzofuran-1-yl]-imidazo[1,2-a]pyridin-6-yl}pyrimidin-2-yl)-3-azabicyclo[3.2.1]octane-8-carboxylic acid;
(1R,5S)-3-(5-{2-(Hydroxymethyl)-3-[(1S,3R)-3-methyl-1,3-dihydroisobenzofuran-1-yl]imidazo[1,2-a]pyridin-6-yl}pyrimidin-2-yl)-3-azabicyclo[3.2.1]octane-8-carboxylic acid;
2-(5-{2-(Hydroxymethyl)-3-[(1R,3S)-3-methyl-1,3-dihydroisobenzofuran-1-yl]imidazo-[1,2-a]pyridin-6-yl}pyrimidin-2-yl)propan-2-ol;
2-(5-{2-(Hydroxymethyl)-3-[(1S,3S)-3-methyl-1,3-dihydroisobenzofuran-1-yl]imidazo[1,2-a]pyridin-6-yl}pyrimidin-2-yl)-propan-2-ol;
{3-[(1R,3S)-3-Methyl-1,3-dihydroisobenzofuran-1-yl]-6-[2-(morpholin-4-yl)pyrimidin-5-yl]imidazo[1,2-a]pyridin-2-yl}methanol;
{3-[(1S,3R)-3-Methyl-1,3-dihydro-isobenzofuran-1-yl]-6-[2-(morpholin-4-yl)pyrimidin-5-yl]imidazo[1,2-a]pyridin-2-yl}-methanol;
4-(5-{2-Methyl-3-[(1S,3S)-3-methyl-1,3-dihydroisobenzofuran-1-yl]imidazo[1,2-a]-pyridin-6-yl}pyrimidin-2-yl)piperazin-2-one; or
2-(5-{2-Methyl-3-[(3S)-3-methyl-1,3-dihydroisobenzofuran-1-yl]imidazo[1,2-a]pyrazin-6-yl}pyrimidin-2-yl)propan-2-ol.

6. A pharmaceutical composition comprising a compound of formula (IIB-A), (IIB-B) or (IIB-C) as defined in claim 1 or an N-oxide thereof, or a pharmaceutically acceptable salt or solvate thereof, or a co-crystal thereof, in association with a pharmaceutically acceptable carrier.

7. A method for the treatment of disorders for which the administration of a modulator of TNFα function is indicated which comprises administering to a patient in need of such treatment an effective amount of a compound of formula (IIB-A), (IIB-B) or (IIB-C) as defined in claim 1 or an N-oxide thereof, or a pharmaceutically acceptable salt or solvate thereof, or a co-crystal thereof.

8. A method for the treatment of an inflammatory or autoimmune disorder, a neurological or neurodegenerative disorder, pain or a nociceptive disorder, a cardiovascular disorder, a metabolic disorder, an ocular disorder, or an ontological disorder, which comprises administering to a patient in need of such treatment an effective amount of a compound of (IIB-A), (IIB-B) or (IIB-C) as defined in claim 1 or an N-oxide thereof, or a pharmaceutically acceptable salt or solvate thereof, or a co-crystal thereof.

* * * * *